(12) United States Patent
Ashizawa

(10) Patent No.: US 10,927,379 B2
(45) Date of Patent: Feb. 23, 2021

(54) COMBINATION THERAPY WITH LIPOSOMAL ANTISENSE OLIGONUCLEOTIDES

(71) Applicant: Bio-Path Holdings, Inc., Bellaire, TX (US)

(72) Inventor: Ana Tari Ashizawa, Bellaire, TX (US)

(73) Assignee: BIO-PATH HOLDINGS, INC., Bellaire, TX (US)

(*) Notice: Subject to any disclaimer, the term of this patent is extended or adjusted under 35 U.S.C. 154(b) by 4 days.

(21) Appl. No.: 16/333,221

(22) PCT Filed: Sep. 15, 2017

(86) PCT No.: PCT/US2017/051723
§ 371 (c)(1),
(2) Date: Mar. 13, 2019

(87) PCT Pub. No.: WO2018/053232
PCT Pub. Date: Mar. 22, 2018

(65) Prior Publication Data
US 2020/0032271 A1 Jan. 30, 2020

Related U.S. Application Data

(60) Provisional application No. 62/395,680, filed on Sep. 16, 2016, provisional application No. 62/487,277, filed on Apr. 19, 2017.

(51) Int. Cl.
| | |
|---|---|
| *C12N 15/113* | (2010.01) |
| *A61P 35/02* | (2006.01) |
| *A61K 9/00* | (2006.01) |
| *A61K 9/127* | (2006.01) |
| *A61K 31/506* | (2006.01) |
| *A61K 31/706* | (2006.01) |
| *A61K 31/7068* | (2006.01) |
| *A61K 31/7088* | (2006.01) |

(52) U.S. Cl.
CPC ........ *C12N 15/1138* (2013.01); *A61K 9/0019* (2013.01); *A61K 9/127* (2013.01); *A61K 31/506* (2013.01); *A61K 31/706* (2013.01); *A61K 31/7068* (2013.01); *A61K 31/7088* (2013.01); *A61P 35/02* (2018.01); *C12N 2310/11* (2013.01); *C12N 2310/31* (2013.01); *C12N 2320/31* (2013.01); *C12N 2320/32* (2013.01); *C12N 2320/35* (2013.01)

(58) Field of Classification Search
None
See application file for complete search history.

(56) References Cited

U.S. PATENT DOCUMENTS

| | | | |
|---|---|---|---|
| 5,087,617 A | 2/1992 | Smith | |
| 5,248,671 A | 9/1993 | Smith | |
| 5,567,433 A | 10/1996 | Collins | |
| 5,855,911 A | 1/1999 | Lopez-Berestein | |
| 6,015,886 A * | 1/2000 | Dale | C07H 21/00 435/6.16 |
| 6,042,846 A | 3/2000 | Lopez-Berestein | |
| 6,111,094 A | 8/2000 | Bennett et al. | |
| 6,977,244 B2 | 12/2005 | Tormo et al. | |
| 7,176,302 B2 | 2/2007 | Lopez-Berestein | |
| 7,220,853 B2 | 5/2007 | Lopez-Berestein et al. | |
| 7,285,288 B1 | 10/2007 | Tormo et al. | |
| 7,309,692 B1 | 12/2007 | Lopez-Berestein et al. | |
| 7,425,545 B2 | 9/2008 | Crooke | |
| 7,704,962 B1 | 4/2010 | Tari et al. | |
| 7,754,872 B2 | 7/2010 | Lopez-Berestein | |
| 7,923,548 B2 | 4/2011 | Lopez-Berestein et al. | |
| 9,744,187 B2 | 8/2017 | Nielsen | |
| 10,335,428 B2 | 7/2019 | Nielsen | |
| 2003/0147813 A1 | 8/2003 | Lyons | |
| 2003/0176376 A1 | 9/2003 | Klem | |
| 2005/0186264 A1 | 8/2005 | Kiani | |
| 2007/0049547 A1 | 3/2007 | Esau | |
| 2007/0238686 A1 * | 10/2007 | Lopez-Berestein | A61P 35/02 514/44 A |
| 2008/0171718 A1 | 7/2008 | Brown | |
| 2011/0190382 A1 | 8/2011 | Gleave | |
| 2011/0250209 A1 * | 10/2011 | Carmeliet | A61P 35/02 424/158.1 |

(Continued)

FOREIGN PATENT DOCUMENTS

| | | |
|---|---|---|
| WO | WO 1997/007784 | 3/1997 |
| WO | WO 1998/001547 | 1/1998 |
| WO | WO 2001/060998 | 8/2001 |

OTHER PUBLICATIONS

Anonymous, "History of Changes for Study: NCT02781883", retrieved from URL:https://clinicaltrials.gov/ct2/history/NCT02781883?V4=View#StudyPageTop, Aug. 10, 2016.
Anonymous, "History of Changes for Study: NCT02923986", retrieved from URL:https://clinicaltrials.gov/ct2/history/NCT02923986?V1=View#StudyPageTop, Oct. 3, 2016.
Ashizawa et al., "BP1001, a Novel Therapeutic for Chronic Myelogenous Leukemia", *Blood*, 128(22):4239, 2016.
Ashizawa et al., "Liposomal delivery of nucleic acid-based anticancer therapeutics: BP-100-1.01", *Exp. Opin. Drug Deliv.*, 12(7):1107-1120, 2015.

(Continued)

*Primary Examiner* — Tracy Vivlemore
(74) *Attorney, Agent, or Firm* — Parker Highlander PLLC

(57) ABSTRACT

Provided herein are methods of treating a cancer in a patient comprising administration of an effective amount of a nuclease-resistant polynucleotide that hybridizes to the translation initiation site of a Grb2 nucleic acid in the patient and either a Bcr-Abl tyrosine kinase inhibitor (e.g., dasatinib) or a cytidine analogue (e.g., decitabine or cytarabine). The cancer may be Ph+ and/or Bcr-Abl positive chronic myelogenous leukemia or acute myeloid leukemia or myelodysplastic syndrome.

56 Claims, 9 Drawing Sheets
Specification includes a Sequence Listing.

(56) References Cited

U.S. PATENT DOCUMENTS

| | | | |
|---|---|---|---|
| 2011/0263609 A1* | 10/2011 | Lee | A61K 31/4184 |
| | | | 514/252.19 |
| 2012/0196823 A1* | 8/2012 | Tutino | A61K 31/706 |
| | | | 514/43 |
| 2014/0121262 A1 | 5/2014 | Feinberg | |
| 2015/0005253 A1* | 1/2015 | Bourrie | A61P 35/02 |
| | | | 514/49 |
| 2020/0113928 A1 | 4/2020 | Nielsen | |

OTHER PUBLICATIONS

Cortes et al, "11 Safety, Pharmacokinetics, and Efficacy of BP-100.1.01 (L-Grb-2 Antisense Oligonucleotide) in Patients with Refractory or Relapsed Acute Myeloid Leukemia (AML), Philadelphia Chromosome Positive Chronic Myelogenous Leukemia (CML), Acute Lymphoblastic Leukemia (ALL), and Myelodysplastic Syndrome (MDS)", Blood, 118(21):3639, 2011.

Extended European Search Report issued in corresponding European Application No. 17851584, dated Mar. 17, 2020.

Gutierrez-Puente et al., "Cellular pharmacology of p-ethoxy antisense oligonucleotides targeted to Bcl-2 in a follicular lymphoma cell line", Leukemia & Lymphoma, 44(11): 1979-1985, 2003.

Gutierrez-Puente et al., "Safety, pharmacokinetics, and tissue distribution of liposomal P-ethoxy antisense oligonucleotides targeted to Bcl-2", J. Pharmacol. Exp. Ther., 291:865-869, 1999.

International Preliminary Report on Patentability issued in corresponding PCT Application No. PCT/US2017/051723, dated Mar. 28, 2019.

International Search Report and Written Opinion issued in corresponding PCT Application No. PCT/US2017/051723, dated Jan. 23, 2018.

Invitation to Pay Additional Fees issued in corresponding PCT Application No. PCT/US2017/051723, dated Nov. 14, 2017.

Lim et al., "Grb2 downregulation leads to Akt inactivation in heregulin-stimulated and ErbB2-overexpressing breast cancer cells", Oncogene, 19:6271-6276, 2000.

McMurty et al., "Liposome-incorporated Grb2 antisense oligonucleotides as a novel therapy against drug resistant chronic myelogenous leukemia" Cancer Res., 68(9_Suppl), 2008.

Ohanian et al., "Safety, Pharmacokinetics, and Efficacy of BP-100-1.01 (Liposomal Grb-2 in Patients with Refractory or Relapsed Acute Myeloid Leukemia (AML), Philadelphia Chromosome Positive Chronic Myelogenous Leukemia (CML), Acute Lymphoblastic Leukemia (ALL), and Myedysplastic Syndrome", Blood, 126(23):3801, 2015.

Tari and Lopez-Berestein, "Cellular uptake of antisense oligonucleotides", Curr. Opin. Invest. Drugs, 2:1450-1453, 2001.

Tari and Lopez-Berestein, "GRB2: a pivotal protein in signal transduction", Semin. Oncol., 28:142-147, 2001.

Tari et al., "Growth inhibition of breast cancer cells by Grb2 downregulation is correlated with inactivation of mitogem-activated protein kinase in EGFR, but not in ErbB2, cells", Oncogene, 18:1325-1332, 1999.

Tari et al., "Inhibition of Grb2 and Crkl proteins results in growth inhibition of Philadelphia chromosome positive leukemia cells", Biochem. Biophys. Res. Commun., 235:383-388, 1997.

Tari et al., "Liposome-incorporated Grb2 antisense oligodeoxynucleotide increases the survival of mice bearing bcr-abl-positive leukemia xenografts", Int. J. Oncol., 31:1243-1250, 2007.

Tari et al., "Pharmacokinetics, tissue distribution, and safety of P-ethoxy oligonucleotides incorporated in liposomes", J. Liposome Res., 8:251-264, 1998.

* cited by examiner

```
                         SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
atatttggcg atggcttc                                                    18

<210> SEQ ID NO 2
<211> LENGTH: 1109
<212> TYPE: DNA
<213> ORGANISM: Homo sapiens
<220> FEATURE:
<221> NAME/KEY: CDS
<222> LOCATION: (79)..(729)

<400> SEQUENCE: 2
gccagtgaat tcggggctc agccctcctc cctcccttcc ccctgcttca ggctgctgag      60
cactgagcag cgctcaga atg gaa gcc atc gcc aaa tat gac ttc aaa gct      111
                    Met Glu Ala Ile Ala Lys Tyr Asp Phe Lys Ala
                     1               5                  10 act gca gac gac gag ctg agc ttc aaa agg ggg gac atc ctc aag gtt      159
Thr Ala Asp Asp Glu Leu Ser Phe Lys Arg Gly Asp Ile Leu Lys Val
             15                  20                  25 ttg aac gaa gaa tgt gat cag aac tgg tac aag gca gag ctt aat gga      207
Leu Asn Glu Glu Cys Asp Gln Asn Trp Tyr Lys Ala Glu Leu Asn Gly
         30                  35                  40 aaa gac ggc ttc att ccc aag aac tac ata gaa atg aaa cca cat ccg      255
Lys Asp Gly Phe Ile Pro Lys Asn Tyr Ile Glu Met Lys Pro His Pro
     45                  50                  55 tgg ttt ttt ggc aaa atc ccc aga gcc aag gca gaa gaa atg ctt agc      303
Trp Phe Phe Gly Lys Ile Pro Arg Ala Lys Ala Glu Glu Met Leu Ser
 60                  65                  70                  75 aaa cag cgg cac gat ggg gcc ttt ctt atc cga gag agt gag agc gct      351
Lys Gln Arg His Asp Gly Ala Phe Leu Ile Arg Glu Ser Glu Ser Ala
                 80                  85                  90 cct ggg gac ttc tcc ctc tct gtc aag ttt gga aac gat gtg cag cac      399
Pro Gly Asp Phe Ser Leu Ser Val Lys Phe Gly Asn Asp Val Gln His
             95                 100                 105 ttc aag gtg ctc cga gat gga gcc ggg aag tac ttc ctc tgg gtg gtg      447
Phe Lys Val Leu Arg Asp Gly Ala Gly Lys Tyr Phe Leu Trp Val Val
         110                 115                 120 aag ttc aat tct ttg aat gag ctg gtg gat tat cac aga tct aca tct      495
Lys Phe Asn Ser Leu Asn Glu Leu Val Asp Tyr His Arg Ser Thr Ser
     125                 130                 135 gtc tcc aga aac cag cag ata ttc ctg cgg gac ata gaa cag gtg cca      543
Val Ser Arg Asn Gln Gln Ile Phe Leu Arg Asp Ile Glu Gln Val Pro
140                 145                 150                 155 cag cag ccg aca tac gtc cag gcc ctc ttt gac ttt gat ccc cag gag      591
Gln Gln Pro Thr Tyr Val Gln Ala Leu Phe Asp Phe Asp Pro Gln Glu
                 160                 165                 170 gat gga gag ctg ggc ttc cgc cgg gga gat ttt atc cat gtc atg gat      639
Asp Gly Glu Leu Gly Phe Arg Arg Gly Asp Phe Ile His Val Met Asp
```

```
              175                 180                 185
aac tca gac ccc aac tgg tgg aaa gga gct tgc cac ggg cag acc ggc        687
Asn Ser Asp Pro Asn Trp Trp Lys Gly Ala Cys His Gly Gln Thr Gly
        190                 195                 200 atg ttt ccc cgc aat tat gtc acc ccc gtg aac cgg aac gtc                729
Met Phe Pro Arg Asn Tyr Val Thr Pro Val Asn Arg Asn Val
    205                 210                 215 taagagtcaa gaagcaatta tttaaagaaa gtgaaaaatg taaaacacat acaaaagaat      789
taaacccaca agctgcctct gacagcagcc tgtgagggag tgcagaacac ctggccgggt      849
caccctgtga ccctctcact ttggttggaa ctttagggg tggagggg cgttggattt        909 aaaaatgcca aaacttacct ataaattaag aagagttttt attacaaatt ttcactgctg     969
ctcctctttc ccctcctttg tctttttttt catccttttt tctcttctgt ccatcagtgc     1029
atgacgttta aggccacgta tagtcctagc tgacgccaat aataaaaaac aagaaaccaa     1089
aaaaaaaaaa cccgaattca                                                  1109
```

<210> SEQ ID NO 3
<211> LENGTH: 217
<212> TYPE: PRT
<213> ORGANISM: Homo sapiens

<400> SEQUENCE: 3

```
Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
            20                  25                  30

Asp Gln Asn Trp Tyr Lys Ala Glu Leu Asn Gly Lys Asp Gly Phe Ile
        35                  40                  45

Pro Lys Asn Tyr Ile Glu Met Lys Pro His Pro Trp Phe Phe Gly Lys
    50                  55                  60

Ile Pro Arg Ala Lys Ala Glu Glu Met Leu Ser Lys Gln Arg His Asp
65                  70                  75                  80

Gly Ala Phe Leu Ile Arg Glu Ser Glu Ser Ala Pro Gly Asp Phe Ser
                85                  90                  95

Leu Ser Val Lys Phe Gly Asn Asp Val Gln His Phe Lys Val Leu Arg
            100                 105                 110

Asp Gly Ala Gly Lys Tyr Phe Leu Trp Val Val Lys Phe Asn Ser Leu
        115                 120                 125

Asn Glu Leu Val Asp Tyr His Arg Ser Thr Ser Val Ser Arg Asn Gln
    130                 135                 140

Gln Ile Phe Leu Arg Asp Ile Glu Gln Val Pro Gln Gln Pro Thr Tyr
145                 150                 155                 160

Val Gln Ala Leu Phe Asp Phe Asp Pro Gln Glu Asp Gly Glu Leu Gly
                165                 170                 175

Phe Arg Arg Gly Asp Phe Ile His Val Met Asp Asn Ser Asp Pro Asn
            180                 185                 190

Trp Trp Lys Gly Ala Cys His Gly Gln Thr Gly Met Phe Pro Arg Asn
        195                 200                 205

Tyr Val Thr Pro Val Asn Arg Asn Val
    210                 215
```

COMBINATION THERAPY WITH LIPOSOMAL ANTISENSE OLIGONUCLEOTIDES

The present application is a national phase application under 35 U.S.C. § 371 of International Application No. PCT/US2017/051723, filed Sep. 15, 2017, which claims the priority benefit of U.S. provisional application No. 62/487,277, filed Apr. 19, 2017, and 62/395,680, filed Sep. 16, 2016, the entire contents of each of which is incorporated herein by reference.

BACKGROUND OF THE INVENTION

1. Field of the Invention

The present invention relates generally to the field of medicine. More particularly, it concerns the treatment of cancer with combination therapy comprising antisense oligonucleotides directed to Grb2.

2. Description of Related Art

The American Cancer Society estimates that in 2015 there were about 6,600 patients with a new diagnosis of chronic myelogenous leukemia (CML) in the United States and about 1,140 deaths from CML. The average age at diagnosis of CML is around 64 years. Almost half of the cases are diagnosed in people 65 and older. This type of leukemia mainly affects adults, and is rarely seen in children. CML is differentiated into chronic, accelerated, and blast phase. Most CML patients are diagnosed in the chronic phase of the disease. If CML patients in chronic phase are not treated, they may rapidly progress to the accelerated and blast phases of the disease.

The Philadelphia chromosome (Ph) is present in 90%-95% of patients with CML. It results from the translocation of chromosomes 9 and 22, which places the abl gene on the 3' end of the bcr gene. This genetic rearrangement is present in all patients, even those where a standard karyotype does not detect the Ph chromosome. This chromosomal translocation produces a chimeric gene, which is expressed as the p210Bcr-Abl fusion protein in Ph+ CML cells. The Bcr-Abl fusion protein has deregulated tyrosine kinase activities, resulting in the activation of the RAS and phosphatidylinositol-3 kinase (PI3K) signal transduction pathways, which leads to malignant transformation of Ph+ cells, proliferation, and survival.

Drugs known as tyrosine kinase inhibitors that target the Bcr-Abl fusion protein are the standard treatment for CML patients. This is because suppressing Bcr-Abl's tyrosine kinase activity decreases Ph+ cell proliferation and survival. Imatinib (Gleevec®), the first generation tyrosine kinase inhibitor, is the standard treatment for CML patients in chronic and accelerated phases. However, CML patients in blast phase do not respond to imatinib. Also, imatinib resistance has been observed in some CML chronic or accelerated phase patients. A second generation tyrosine kinase inhibitor (e.g., dasatinib (Das)) is usually given to CML patients who cannot tolerate imatinib or who are resistant to imatinib. But CML patients will not respond to imatinib or second generation tyrosine kinase inhibitors if the Bcr-Abl fusion protein adopts the T315I gene mutation. There is a need to develop more effective therapies for CML patients, who are in accelerated or blast phase, or who are resistant to tyrosine kinase inhibitors.

SUMMARY OF THE INVENTION

In one embodiment, provided herein are methods of treating a cancer in a patient in need thereof comprising administering to the patient an effective amount of a first pharmaceutical therapy comprising a nuclease-resistant polynucleotide that hybridizes to a Grb2 nucleic acid in the patient and a second pharmaceutical therapy comprising a Bcr-Abl tyrosine kinase inhibitor. In some aspects, provided herein are compositions for use in treating a cancer in a patient in need thereof, said compositions comprising a first pharmaceutical therapy comprising a nuclease-resistant polynucleotide that hybridizes to a Grb2 nucleic acid in the patient and a second pharmaceutical therapy comprising a Bcr-Abl tyrosine kinase inhibitor.

In some aspects, the polynucleotide hybridizes to the translation initiation site of a Grb2 nucleic acid. In some aspects, the polynucleotide is an oligonucleotide having a length of 8-50 bases. In some aspects, the polynucleotide has a sequence according to SEQ ID NO: 1. In some aspects, the polynucleotide comprises P-ethoxy backbone linkages.

In some aspects, the polynucleotide is encapsulated in a liposome. In some aspects, the first pharmaceutical therapy further comprises a neutral lipid. In some aspects, the first pharmaceutical therapy is BP1001. In some aspects, the first pharmaceutical therapy is administered systemically. In some aspects, the first pharmaceutical therapy is formulated for intraarterial or intravenous administration. In some aspects, the first pharmaceutical therapy is administered at a dosage of from about 60 mg/m$^2$ and to about 90 mg/m$^2$. In some aspects, the first pharmaceutical therapy is administered two to four times per week.

In some aspects, the Bcr-Abl tyrosine kinase inhibitor is dasatinib, imatinib, nilotinib, bosutinib, ponatinib, or bafetinib. In one aspect, the Bcr-Abl tyrosine kinase inhibitor is dasatinib. In some aspects, the dasatinib is administered at a dosage of about 140 mg. In some aspects, the dasatinib is administered once daily.

In some aspects, the second pharmaceutical therapy is administered systemically. In some aspects, the second pharmaceutical therapy is administered orally, intraarterially, or intravenously. In some aspects, the first pharmaceutical therapy is administered prior to the administration of the second pharmaceutical therapy.

In some aspects, the first pharmaceutical therapy and the second pharmaceutical therapy are administered concurrently. In some aspects, the first pharmaceutical therapy and the second pharmaceutical therapy are administered by distinct routes.

In some aspects, the patient is a human. In some aspects, the patient has previously failed treatment with imatinib.

In some aspects, the cancer is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma. In some aspects, the cancer is a blood cancer. In some aspects, the blood cancer is a chronic myelogenous leukemia (CML), an acute myeloid leukemia (AML), or a myelodysplastic syndrome (MDS). In some aspects, the CML is an accelerated CML or a blast-phase CML. In some aspects, the CML or AML is Bcr-Abl positive CML or Bcr-Abl positive AML. In some aspects, the Bcr-Abl positive CML or Bcr-Abl positive AML is positive for a T315I Bcr-Abl mutation. In some aspects, the CML or AML is a Philadelphia chromosome-positive CML or Philadelphia chromosome-positive AML.

In one embodiment, provided herein are methods of treating a cancer or myelodysplastic syndrome (MDS) in a patient in need thereof comprising administering to the patient an effective amount of a first pharmaceutical therapy comprising a nuclease-resistant polynucleotide that hybridizes to a Grb2 nucleic acid and a second pharmaceutical therapy comprising a cytidine analogue. In some aspects, compositions are provided herein for use in treating a cancer or myelodysplastic syndrome (MDS) in a patient in need thereof, said compositions comprising an effective amount of a first pharmaceutical therapy comprising a nuclease-resistant polynucleotide that hybridizes to a Grb2 nucleic acid and a second pharmaceutical therapy comprising a cytidine analogue.

In some aspects, the polynucleotide hybridizes to the translation initiation site of a Grb2 nucleic acid. In some aspects, the polynucleotide is an oligonucleotide having a length of 8-50 bases. In some aspects, the polynucleotide has a sequence according to SEQ ID NO: 1. In some aspects, the polynucleotide comprises P-ethoxy backbone linkages.

In some aspects, the polynucleotide is encapsulated in a liposome. In some aspects, the first pharmaceutical therapy further comprises a neutral lipid. In some aspects, the first pharmaceutical therapy is BP1001. In some aspects, the first pharmaceutical therapy is administered systemically. In some aspects, the first pharmaceutical therapy is formulated for intraarterial or intravenous administration. In some aspects, the first pharmaceutical therapy is administered at a dosage of from about 60 mg/m$^2$ and to about 90 mg/m$^2$. In some aspects, the first pharmaceutical therapy is administered two to four times per week.

In some aspects, the cytidine analogue is decitabine, cytarabine, or azacitidine. In one aspect, the cytidine analogue is decitabine. In one aspects, the cytidine analogue is cytarabine In some aspects, the cytarabine is administered at a dosage of about 20 mg. In some aspects, the cytarabine is administered twice daily. In some aspects, the cytarabine is administered subcutaneously.

In some aspects, the first pharmaceutical therapy is administered prior to the administration of the second pharmaceutical therapy. In some aspects, the first pharmaceutical therapy and the second pharmaceutical therapy are administered concurrently. In some aspects, the second pharmaceutical therapy is administered prior to the administration of the first pharmaceutical therapy. In some aspects, the first pharmaceutical therapy and the second pharmaceutical therapy are administered by distinct routes.

In some aspects, the patient is a human.

In some aspects, the cancer is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma. In some aspects, the cancer is a blood cancer. In some aspects, the blood cancer is a chronic myelogenous leukemia (CML), an acute myeloid leukemia (AML), or a myelodysplastic syndrome (MDS). In some aspects, the CML is an accelerated CML or a blast-phase CML. In some aspects, the CML or AML is Bcr-Abl positive CML or Bcr-Abl positive AML. In some aspects, the Bcr-Abl positive CML or Bcr-Abl positive AML is positive for a T315I Bcr-Abl mutation. In some aspects, the CML or AML is a Philadelphia chromosome-positive CML or Philadelphia chromosome-positive AML.

In one embodiment, compositions are provided comprising a population of oligonucleotides that hybridize to a GRB2 polynucleotide gene product. In some aspects, the oligonucleotides of the population are composed of nucleoside molecules linked together through phosphate backbone linkages, wherein at least one of the phosphate backbone linkages in each oligonucleotide is a P-ethoxy backbone linkage, and wherein no more than 80% of the phosphate backbone linkages in each oligonucleotide are P-ethoxy backbone linkages. In some aspects, at least one of the phosphate backbone linkages in each oligonucleotide is a phosphodiester backbone linkage. In some aspects, the oligonucleotides of the population comprise a sequence according to SEQ ID NO: 1. In various aspects, the oligonucleotides of the population inhibit the expression of Grb2 protein. In some aspects, the composition is lyophilized.

In some aspects, 10% to 80% of the phosphate backbone linkages are P-ethoxy backbone linkages; 20% to 80% of the phosphate backbone linkages are P-ethoxy backbone linkages; 30% to 80% of the phosphate backbone linkages are P-ethoxy backbone linkages; 40% to 80% of the phosphate backbone linkages are P-ethoxy backbone linkages; 50% to 80% of the phosphate backbone linkages are P-ethoxy backbone linkages; or 60% to 70% of the phosphate backbone linkages are P-ethoxy backbone linkages, or any range derivable therein. In some aspects, 20% to 90% of the phosphate backbone linkages are phosphodiester backbone linkages; 20% to 80% of the phosphate backbone linkages are phosphodiester backbone linkages; 20% to 70% of the phosphate backbone linkages are phosphodiester backbone linkages; 20% to 60% of the phosphate backbone linkages are phosphodiester backbone linkages; 20% to 50% of the phosphate backbone linkages are phosphodiester backbone linkages; or 30% to 40% of the phosphate backbone linkages are phosphodiester backbone linkages, or any range derivable therein. In various aspects, at least 5%, 10%, 15%, 20%, 25%, 30%, 35%, 40%, 45%, 50%, 55%, 60%, 65%, 60%, 65%, 70%, 75%, 80%, 85%, 90%, or 95%, or any value therein, of the phosphate backbone linkages are P-ethoxy backbone linkages. In various aspects, at most 5%, 10%, 15%, 20%, 25%, 30%, 35%, 40%, 45%, 50%, 55%, 60%, 65%, 70%, 75%, 80%, 85%, 90%, or 95%, or any value therein, of the phosphate backbone linkages are phosphodiester backbone linkages. In certain aspects, the phosphodiester backbone linkages are distributed throughout the oligonucleotides. As such, the oligonucleotides are not chimeric molecules. In some aspects, the oligonucleotides do not comprise a phosphorothioate backbone linkage.

In some aspects, the oligonucleotides of the population have a size ranging from 7 to 30 nucleotides. In certain aspects, the oligonucleotides of the population have a size ranging from 12 to 25 nucleotides. In various aspects, the oligonucleotides of the population have a size of at least 5, 6, 7, 8, 9, 10, 11, 12, 13, 14, 15, 16, 17, 18, 19, 20, 21, 22, 23, 24, 25, 26, 27, 28, 29, or 30 nucleotides. The size range may be an average size of the oligonucleotides in the population.

In some aspects, the oligonucleotides of the population have an average size of 7, 8, 9, 10, 11, 12, 13, 14, 15, 16, 17, 18, 19, 20, 21, 22, 23, 24, 25, 26, 27, 28, 29, or 30 nucleotides, wherein no more than 5, 6, 7, 8, 8, 9, 10, 11, 11, 12, 13, 14, 15, 15, 16, 17, 18, 19, 20, 20, 21, 22, 23, or 24, respectively, of the phosphate backbone linkages in each oligonucleotide is a P-ethoxy backbone linkage. In some aspects, the oligonucleotides of the population have an average size of 7, 8, 9, 10, 11, 12, 13, 14, 15, 16, 17, 18, 19, 20, 21, 22, 23, 24, 25, 26, 27, 28, 29, or 30 nucleotides and at least 2, 2, 2, 2, 3, 3, 3, 3, 4, 4, 4, 4, 4, 5, 5, 5, 5, 5, 6, 6, 6, 6, or 6, respectively, of the phosphate backbone linkages in each oligonucleotide is a phosphodiester backbone linkage.

In some aspects, the population of oligonucleotides comprises a single species of oligonucleotides. In other aspects, the population of oligonucleotides comprises at least two species of oligonucleotides. A single species of oligonucleotide may have the same nucleotide sequence but either have or lack P-ethoxy linkages in different positions within the molecule. As such, the population may be homogeneous as to the nucleotide sequence and heterogeneous as to the distribution of phosphodiester backbone linkages among the oligonucleotides of the population. In addition, the population may be heterogeneous as to the number of P-ethoxy backbone linkages and phosphodiester backbone linkages among the oligonucleotides of the population. As a non-limiting example, a first portion of the oligonucleotides of the population may have 70% P-ethoxy linkages and 30% phosphodiester linkages while a second portion of the oligonucleotides of the population may have 60% P-ethoxy linkages and 40% phosphodiester linkages. In some aspects, the population of oligonucleotides comprises antisense oligonucleotides, short interfering RNAs (siRNAs), microRNAs (miRNAs), or piwiRNAs (piRNAs).

In various aspects, the composition further comprises phospholipids. In some aspects, the phospholipids and oligonucleotides are present at a molar ratio of from about 5:1 to about 100:1. In some aspects, the oligonucleotides and phospholipids form an oligonucleotide-lipid complex, such as, for example, a liposome complex. In some aspects, at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the liposomes are less than 5 microns in diameter. In some aspects, the population of oligonucleotides are incorporated in the population of liposomes.

In some aspects, the phospholipids are uncharged or have a neutral charge at physiologic pH. In some aspects, the phospholipids are neutral phospholipids. In certain aspects, the neutral phospholipids are phosphatidylcholines. In certain aspects, the neutral phospholipids are dioleoylphosphatidyl choline. In some aspects, the phospholipids are essentially free of cholesterol.

In one embodiment, pharmaceutical compositions are provided comprising a composition of oligonucleotides and phospholipids of the present embodiments and a pharmaceutically acceptable carrier. In some aspects, the composition further comprises a chemotherapeutic agent.

In one embodiment, methods are provided for reducing the expression level of Grb2 protein in a cell comprising contacting the cell with an oligonucleotide composition of the present embodiments. In some aspects, the cell is a mammalian cell. In some aspects, the cell is a cancer cell.

In one embodiment, methods are provided for delivering a therapeutically effective amount of an oligonucleotide to a cell comprising contacting the cell with a pharmaceutical composition of the present embodiments. In some aspects, the method is a method of treating hyperplasia, cancer, an autoimmune disease, or an infectious disease.

In one embodiment, methods are provided for treating a subject with cancer, an autoimmune disease, or an infectious disease comprising administering to the subject a therapeutically effective amount of a pharmaceutical composition of the present embodiments. In some aspects, the subject is a human. In some aspects, the cancer is a bladder, blood, lymphoma, pancreas, bone, bone marrow, brain, breast, colon, esophagus, stomach, head and neck, kidney, liver, lung, prostate, skin, testis, tongue, ovary, or uterine cancer. Tumors treatable with the methods of the present invention include, but are not limited to, melanoma, prostate cancer, ovarian cancer, breast cancer, mammary cancer, head and neck squamous cell cancer, papillary renal cell carcinoma, gall bladder cancer, rectal cancer, pancreatic cancer, lung cancer, colon cancer, glioma, astrocytoma, classical Hodgkin's lymphoma, and smooth muscle tumors, as well as cells from glioblastoma, bone marrow stem cells, hematopoietic cells, osteoblasts, epithelial cells, fibroblasts, as well as any other tumor cells which undergo apoptosis and induce resistance to or regression of tumor cells. In some aspects, the autoimmune disease is Lupus erythematosis, Spondyloarthropathy, Sjogren's disease, Crohn's disease, diabetes mellitus, multiple sclerosis, or rheumatoid arthritis. In some aspects, the infectious disease is a bacterial infection, fungal infection, viral infection, or parasitic infection. In some aspects, the composition is administering subcutaneously, intravenously, or intraperitoneally. In some aspects, the method further comprises administering at least a second anticancer therapy to the subject. In some aspects, the second anticancer therapy is a surgical therapy, chemotherapy, radiation therapy, cryotherapy, hormone therapy, immunotherapy, or cytokine therapy. In some aspects, administration of the composition reduces expression of Grb2 protein in the patient.

"Entrap," "encapsulate," and "incorporate" refer to the lipid or liposome forming an impediment to free diffusion into solution by an association with or around an agent of interest, e.g., a liposome may encapsulate an agent within a lipid layer or within an aqueous compartment inside or between lipid layers. In certain embodiments, the composition is comprised in a pharmaceutically acceptable carrier. The pharmaceutically acceptable carrier may be formulated for administration to a human subject or patient.

In certain embodiments, the lipid component has an essentially neutral charge because it comprises a neutral phospholipid or a net neutral charge. In certain aspects a neutral phospholipid may be a phosphatidylcholine, such as DOPC, egg phosphatidylcholine ("EPC"), dilauroylphosphatidylcholine ("DLPC"), dimyristoylphosphatidylcholine ("DMPC"), dipalmitoylphosphatidylcholine ("DPPC"), distearoylphosphatidylcholine ("DSPC"), dilinoleoylphosphatidylcholine, 1,2-diarachidoyl-sn-glycero-3-phosphocholine ("DAPC"), 1,2-dieicosenoyl-sn-glycero-3-phosphocholine ("DEPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), 1-palmitoyl-2-oleoyl phosphatidylcholine ("POPC"), 1-oleoyl-2-palmitoyl phosphatidylcholine ("OPPC"), or lysophosphatidylcholine. In other aspects the neutral phospholipid can be a phosphatidylethanolamine, such as dioleoylphosphatidylethanolamine ("DOPE"), distearoylphophatidylethanolamine ("DSPE"), dimyristoyl phosphatidylethanolamine ("DMPE"), dipalmitoyl phosphatidylethanolamine ("DPPE"), palmitoyloleoyl phosphatidylethanolamine ("POPE"), or lysophosphatidylethanolamine. In certain embodiments, the phospholipid component can comprise 1, 2, 3, 4, 5, 6, 7, 8, or more kinds or types of neutral phospholipid. In other embodiments, a phospholipid component can comprise 2, 3, 4, 5, 6 or more kinds or type of neutral phospholipids.

In certain embodiments, a lipid component can have an essentially neutral charge because it comprises a positively charged lipid and a negatively charged lipid. The lipid component may further comprise a neutrally charged lipid(s)

or phospholipid(s). The positively charged lipid may be a positively charged phospholipid. The negatively charged lipid may be a negatively charged phospholipid. The negatively charged phospholipid may be a phosphatidylserine, such as dimyristoyl phosphatidylserine ("DMPS"), dipalmitoyl phosphatidylserine ("DPPS"), or brain phosphatidylserine ("BPS"). The negatively charged phospholipid may be a phosphatidylglycerol, such as dilauroylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), or dioleoylphosphatidylglycerol ("DOPG"). In certain embodiments, the composition further comprises cholesterol or polyethyleneglycol (PEG). In other embodiments, the composition is essentially free of cholesterol. In certain embodiments, a phospholipid is a naturally-occurring phospholipid. In other embodiments, a phospholipid is a synthetic phospholipid.

Liposomes can be made of one or more phospholipids, as long as the lipid material is substantially uncharged. It is important that the composition be substantially free of anionic and cationic phospholipids and cholesterol. Suitable phospholipids include phosphatidylcholines and others that are well known to persons that are skilled in this field.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6A shows treatment of mice harboring 32Dp210 BCR-ABL positive leukemia xenografts with 15 mg/kg/dose of BP1001. FIG. 6B shows treatment of mice harboring 32Dp210 BCR-ABL positive leukemia cells with 5, 10, or 15 mg/kg/dose BP1001.

FIG. 7A shows 1 h pretreatment with BP1001 prior to dosing with dasatinib. FIG. 7B shows 1 day pretreatment with dasatinib prior to dosing with BP1001. FIG. 7C shows 1 day pretreatment with BP1001 prior to dosing with dasatinib.

FIG. 8A shows the percentage of cells in the sub-G1 phase. FIG. 8B shows the percentage of cells in the G1 phase. FIG. 8C shows the percentage of cells in the S phase. FIG. 8D shows the percentage of cells in the G2/M phase.

FIG. 9A shows the percentages of cells in the sub-G1 phase following pretreatment with BP1001. FIG. 9B shows the percentages of cells in the sub-G1 phase following pretreatment with a tyrosine kinase inhibitor.

DESCRIPTION OF ILLUSTRATIVE EMBODIMENTS

I. Growth Factor Receptor-Bound Protein 2 (Grb2)

The grb2 gene has been mapped to the human chromosome region 17q22-qter, a region that is duplicated in leukemias, which may result in an increased copy number of the grb2 gene product. As Grb2 is important for the transformation of murine hematopoietic cells, and the proliferation of human leukemia cells that express high levels of oncogenic tyrosine kinases, inhibition of Grb2 may have a significant impact on the natural history of leukemias.

Grb2 links oncogenic tyrosine kinases with their downstream signaling molecules, such as ERK and AKT, which are critical regulators of cell proliferation and survival. The Grb2 adaptor protein contains one Src homology 2 (SH2) domain, flanked by two Src homology 3 (SH3) domains. Grb2 uses its SH2 domain to bind to phosphotyrosine residues found in activated tyrosine kinases, such as Bcr-Abl, c-Cbl, and epidermal growth factor receptor (EGFR), while it uses its SH3 domains to bind to proline-rich motifs, such as those found in the guanine nucleotide exchange factor, Son of Sevenless (SOS). RAS, a GTPase protein, is active when bound to GTP, and inactive when bound to GDP. Guanine nucleotide exchange factors, such as SOS, increase the exchange of GDP for GTP on RAS. Upon growth factor stimulation, the Grb2-SOS complex is recruited to the plasma membrane, where it uses its SH2 domain to bind to growth factor-stimulated tyrosine kinase receptors. This binding allows SOS to be in close proximity to RAS, which is localized to the plasma membrane. It is thus able to stimulate RAS activity. RAS activation will then in turn activate multiple downstream signaling pathways important for the regulation of diverse cellular processes (Tani, 2001a).

Figure 4:
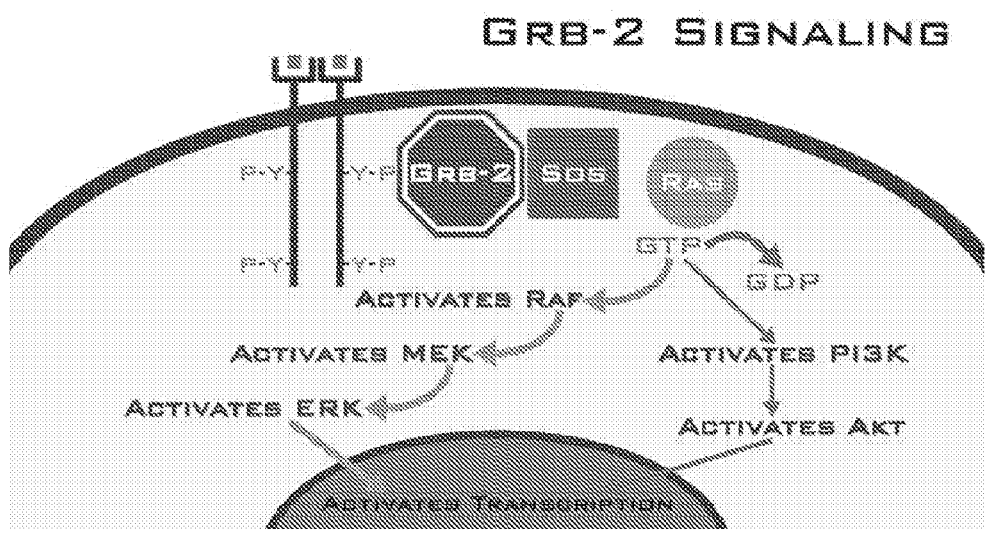
FIG. 4. Diagram illustrating the critical role of GRB2 in relaying tyrosine kinase signals.

The most well-known RAS signaling pathway is the mitogen activated protein (MAP) kinase cascade. In this cascade, RAS binds to RAF in a GTP-dependent manner. This binding leads to RAF activation. Activated RAF phosphorylates (mitogen activated protein kinase kinase) MEK, which in turn phosphorylates and activates (extracellular regulated kinases 1,2) ERK1,2. Activated ERK1,2 then translocates to the nucleus, and activates transcription by phosphorylating transcription factors (e.g., ELK-1 and MYC). FIG. 4 illustrates the Grb2 signaling pathway. Like the Bcr-Abl oncogene, the c-Cbl proto-oncogene is constitutively tyrosine phosphorylated in CML cells. Grb2 may mediate c-CBL-driven pathways in CML cells because Grb2 has been shown to form stable complexes with c-Cbl. This interaction may result in malignant transformation of myeloid progenitor cells.

By inhibiting Grb2, the Grb2-SOS complex is no longer capable of exchanging GDP for GTP on RAS. Therefore down-regulation of the MAP kinase cascade and its resultant transcription occurs (Tani 2001a).

II. Inhibition of Grb2 Gene Expression

Multiple strategies for inhibiting the function of Grb2 have been investigated. One strategy involves cloning an alternatively spliced form of Grb2, which has a deleted non-functional SH2 domain (Fath, 1994). The encoded Grb3-3 protein will not bind to phosphorylated EGFR because the deleted residues are integral to the binding of Grb2 to phosphotyrosine residues; Grb3-3 does, however, retain functional SH3 domains. Hence, Grb3-3 can compete with Grb2 in the binding of guanine nucleotide exchange factors. In a study by Fath et al. (1994), microinjection of Grb3-3 into Swiss 3T3 fibroblasts induced them to undergo apoptosis. These clones are designed to compete with Grb2 in the binding of guanine nucleotide exchange factors.

A second strategy uses small molecule inhibitors to prevent the binding of growth factor receptors to the Grb2 SH2 domain (Gay, 1999). These small molecule Grb2 SH2 inhibitors are designed using molecular models, based on X-ray structures of Grb2, complexed with phosphopeptide ligands containing the Tyr-X-Asn-X motif. These inhibitors contain elements able to recognize and selectively bind the Grb2 SH2 domain. The goal of these inhibitors is to reverse oncogenic transformation, and prevent growth factor-induced cell motility (Gay, 1999).

A third strategy involves the use of Grb2-binding phosphopeptides (Williams, 1997). Treating cells with cell-permeable Grb2 binding phosphopeptides results in their association with the Grb2, and its inhibition of the growth factor receptor binding to Grb2 (Williams, 1997). This may halt growth factor-stimulated mitogenesis.

Fourth, inhibition of Grb2 expression may be achieved with the use of antisense oligonucleotides complementary to specific regions of the Grb2 mRNA. When the antisense oligonucleotides bind to the target mRNA, a DNA-RNA hybrid is formed. The hybrid formation inhibits the translation of the mRNA, and thus, the expression of the encoded protein. If the Grb2 protein is essential for the proliferation of the cell, its inhibition may lead to growth suppression. Inhibition of Grb2 expression may also overcome drug resistance and promote chemotherapy-induced apoptosis in cancer cells.

III. P-Ethoxy Oligonucleotide Antisense Therapy Against Grb2 and its Inhibitory Activity Against CML and AML The growth factor receptor bound protein-2 (Grb2) is utilized by oncogenic tyrosine kinases, such as Bcr-Abl, to activate the Ras pathway. Grb2 is required by Bcr-Abl to transform fibroblasts and induce leukemia-like diseases in mice. BP1001, a liposome-incorporated antisense oligodeoxynucleotide (oligo) specific to the grb2 mRNA, was developed to block Grb2 expression. The contiguous cDNA sequence of Grb2 is provided in SEQ ID NO: 2 and the protein sequence of Grb2 is provided in SEQ ID NO: 3.

The strategy employed in this trial to inhibit Grb2 utilizes liposome-incorporated, nuclease-resistant antisense oligonucleotide specific for Grb2 mRNA. The antisense oligonucleotide drug substance in BP1001 is a nuclease-resistant phosphodiester analog that contains a P-ethoxy backbone. This structure was chosen over one with a phosphorothioate backbone, because it lacks a sulfur moiety. The sulfur moiety of the phosphorothioate backbone has been associated with a bleeding diathesis.

Figure 5A:
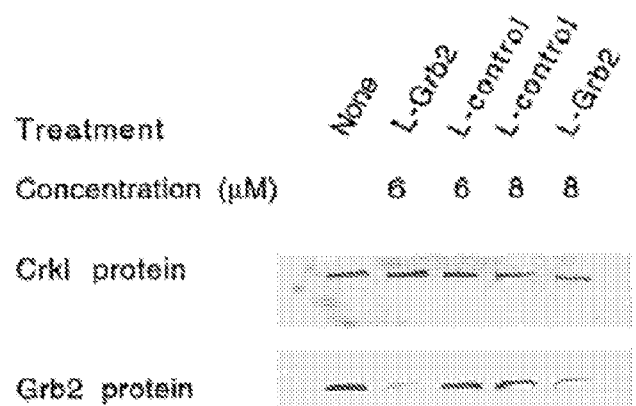
FIGS. 5A-B. Selective inhibition of the production of Grb2 proteins. BV173 (FIG. 5A) and ALL-1 (FIG. 5B) cells were incubated with 4 to 8 µM of L-Grb2 antisense oligos and L-control oligos. After three days of culture, protein-containing layers were prepared and subjected to SDS-PAGE and transferred to nitrocellulose membranes. Blots were cut into sections and incubated with antibodies specific for Grb2 (target) or Crk1 (control) protein.
Figure 5B:
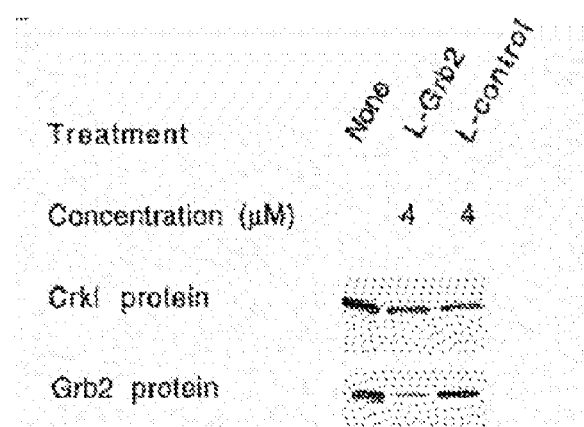

The oligonucleotide sequence being used is: 5'-ATAT-TTGGCGATGGCTTC-3' (SEQ ID NO: 1), and is specific for the translation initiation site of human Grb2 mRNA, thereby impairing Grb2 protein production. This antisense has been shown to inhibit Grb2 expression and cell growth in Bcr-Abl-positive leukemic cells, as well as in breast cancer cells that express high levels of HER2/neu or EGFR (FIGS. 5A-B).

BP1001 is a neutral liposome incorporated with the nuclease-resistant, hydrophobic P-ethoxy antisense oligos targeted to Grb2 mRNA. In preclinical studies, BP1001 was effective in inducing growth inhibition and decreasing ERK1,2 and Akt phosphorylation in imatinib-sensitive and imatinib-resistant CML cell lines. In addition, BP1001 was shown to selectively inhibit Grb2 protein production in Ph+ leukemic cell lines BV173 and ALL-1, and was also found to inhibit the proliferation of Bcr-Abl+ leukemic cell lines (ALL-1, BV173, and K562 cells) (Table 16).

TABLE 16

Inhibition of proliferation of leukemic cell lines by BP1001

| Cell Line | [BP1001] µM | Incubation Time (days) | Decrease in viability (%) | IC$_{50}$ (µM) |
|---|---|---|---|---|
| ALL-1 | 0-6 | 5 | 100 | 4 |
| BV173 | 0-10 | 5 | 70 | 8 |
| K562 | 0-12 | 4 | 80 | 8 |
| HL60* | 0-12 | 5 | 0 | — |

*Ph-negative leukemia cell line (Bcr-Abl negative)

Inhibition of Grb2 protein expression led to cell growth inhibition in Bcr-Abl+ cell lines derived from Ph+ leukemic patients, demonstrating that Grb2 plays a functional role in Bcr-Abl induced cell proliferation, and hence, a vital role in the maintenance of the tumorigenic potential of Ph+ leukemias. These results show that down-regulation of the Grb2 protein can lead to inhibition of cell growth as regulated by the Bcr-Abl tyrosine kinase.

BP1001 was effective in increasing the survival of NOD/SCID mice bearing Bcr-Abl-positive leukemia xenografts (Tari, 2007). Studies have shown an antitumor response to this agent in mice injected with 32Dp210 Bcr-Abl positive leukemia cells that were subsequently treated with BP1001.

Figure 6A:
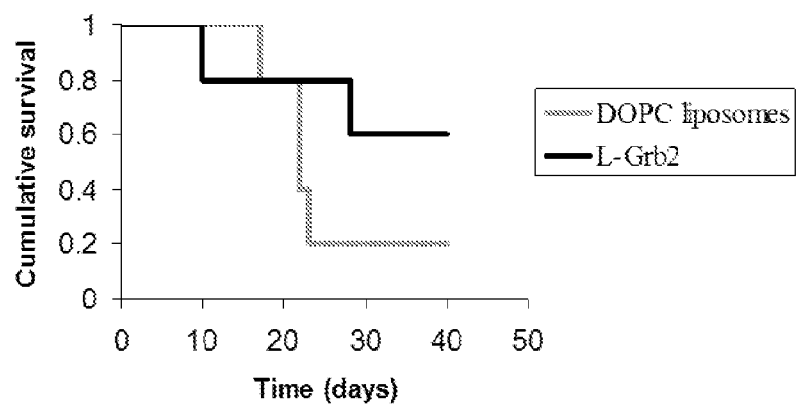
FIGS. 6A-B. Activity of BP1001 in mouse models of leukemia.

In one study, mice injected with 32Dp210 Bcr-Abl positive leukemia cells were treated with BP1001 (15 mg/kg/dose) or control (empty DOPC liposomes) intravenously beginning one day after injection of tumor cells, twice weekly for up to 6 weeks Mice were observed daily for moribundity/morbidity. All surviving mice were euthanized on Day 40. In mice injected with 32Dp210 Bcr-Abl positive leukemia cells, 60% treated with BP1001 survived to 40 days (end of study) compared to 17% of mice receiving empty liposomes. Mean survival duration in these treated animals was 31.6±13.1 days compared to 23.7±8.3 days in the empty liposome group (FIG. 6A).

Figure 6B:
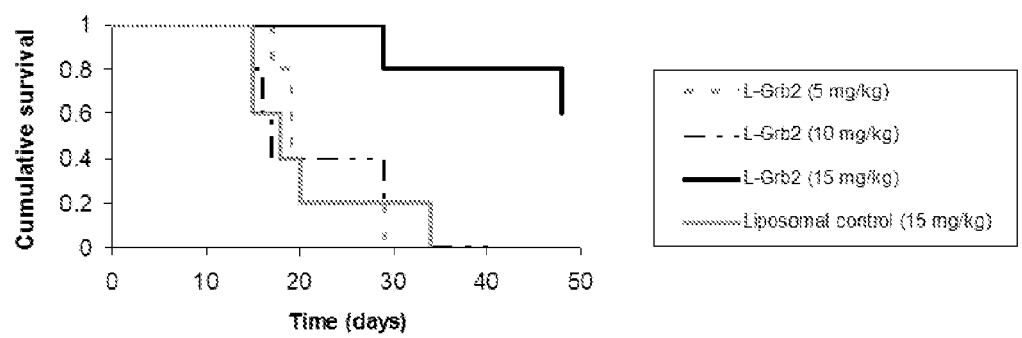

In a second study in mice injected with 32Dp210 Bcr-Abl positive leukemia cells, treatment groups received BP1001 at 5, 10, or 15 mg/kg/dose administered intravenously beginning one day after injection of tumor cells, twice weekly for up to 7 weeks. Control groups received DOPC liposomes containing an oligonucleotide of random sequence (15 mg/kg/dose) on the same schedule. Mice were observed daily for moribundity/morbidity. Surviving mice in the control groups were euthanized on Day 41, and in the treatment groups on Day 48. At a dose level of 15 mg/kg/dose, 80% of mice treated with BP1001 survived to 48 days (end of study), compared to 0% of mice receiving 15 mg/kg/dose of liposomal control oligonucleotide (FIG. 6B). Mean survival duration was 44.2±8.5 versus 20.4±7.9 days in these groups, respectively. Mean survival duration in mice treated with 5 or 10 mg/kg/dose BP1001 was 20.8±4.7 and 22.2±8.7 days, respectively. Results indicated twice weekly BP1001 treatment at a dose level of 15 mg/kg/dose increased survival in mice induced with 32Dp210 Bcr-Abl positive CML compared to control oligonucleotide treatment.

In addition, a significant reduction in peripheral blasts was observed in a CML patient in a Phase I trial (from 81% to 5%) after receiving four BP1001 infusions. The patient had CML blast crisis, characterized by the T315I mutation. These data suggest that Grb2 plays a critical role in CML progression. Furthermore, preclinical studies indicate that BP1001 pretreatment enhances cytarabine cytotoxicity in acute myeloid leukemia (AML) cells.

IV. BP1001 Pharmacology and Toxicology

A. Pharmacokinetic Studies in Rats

Pharmacokinetic studies of BP1001 were conducted in rats after intravenous (i.v.) administration (Tani, 2007). Lewis rats (n=5, 400 gm) underwent cannulation of the right femoral artery and left femoral vein and were injected i.v. with radio-labeled ($^{32}$P) BP1001 at a dose of 10 mg of oligonucleotide per kg of body weight. Blood (0.3 mL) was collected through the right femoral artery at 5, 10, 20, 30, 60, 90, 120, 180, and 240 minutes following injection. After each withdrawal, the catheter was flushed with sodium heparin 1:1000 (Units/mL). Whole blood samples were extracted and assayed for $^{32}$P radioactivity by liquid scintillation as previously described (Tani, 1998; Gutierrez-Puente, 1999). Pharmacokinetic parameters were determined by nonlinear regression analysis (Rstrip; Micro Math, Inc., Salt Lake City, Utah). Whole blood drug concentration data were best fit to a two-compartment model. The clearance of BP1001 from blood was found to closely fit a two-compartment mathematical model (correlation $r^2 > 0.98$). The initial distribution phase occurred over the first 6 min after injection ($t_{1/2\alpha} = 5.16 \pm 0.3$ min). The terminal phase half-life ($t_{1/2\beta}$) was 225.6±13.2 min. The immediate apparent volume of distribution (36.42±1.88 mL) was higher than the total blood volume for rats of this size. Area under the concentration curve (AUC) was 5.4±0.9 mg/mL×min, while residence time was 309.6±21.5 minutes. The pharmacokinetic distribution of BP1001 and high volume of distribution observed in this study were similar to that reported for other liposome-incorporated P-ethoxy oligonucleotides previously investigated (Tani, 1998; Gutierrez-Puente, 1999).

B. BP1001 Tissue Distribution Studies in Mice

Tissue distribution studies of BP1001 were conducted in mice following i.v. administration. Twenty mice (5/group) were divided into three test article groups and one control group. Test article groups were injected i.v. via the tail vein with radio-labeled ($^{32}$P) BP1001 at a dose of 20 mg of oligonucleotide per kg of body weight. Injected mice were euthanized by $CO_2$ inhalation at 4, 24, and 48 hours following injection for organ harvest. Control animals were non-injected animals. Spleen, liver, kidney, heart, stomach, lung, and bone marrow tissue were collected from all animals, and tissue samples (50-100 mg) from each organ were weighed and processed. $^{32}$P radioactivity was counted in a scintillation counter. Results were expressed as mean μg BP1001/g tissue. As expected, no radioactivity was detected in control animals. The tissue distribution of BP1001 was similar to that reported for other liposome-incorporated P-ethoxy oligonucleotides previously investigated. BP1001 accumulated in all tissues examined, with the highest accumulation in spleen, liver, and kidney tissue. At 4 h following injection, mean BP1001 tissue concentrations per g of tissue were: 64 μg (spleen), 50 μg (liver), 34 μg (kidney), and ranged from 12-34 μg in other tissues. The tissue half-life was approximately 24 h in spleen, liver, kidney, heart, and stomach and 48 h in lungs. A minimal amount of BP1001 (~0.4 μg in two femurs) was detected in the bone marrow, where the concentration remained relatively constant for 72 h.

C. BP1001 Toxicology

1. Single-Dose Toxicity Study in Mice

In a single dose toxicity study of BP1001, 15 male ICR mice (5/group) were assigned to a non-injected control group (Group I) and two treatment groups (Groups II and III) to receive 15 and 30 mg oligo/kg intravenously via the tail vein as a single injection. Fifteen female ICR mice (5/group) were assigned to a non-injected control group (Group IV) and two treatment groups (Groups V and VI) to receive 20 and 40 mg oligo/kg, respectively, intravenously via the tail vein as a single injection. Animals were observed daily and blood was collected for hematology and clinical chemistry evaluations at two and six weeks post injection. Animals were sacrificed following blood collection at six weeks post-injection and tissues collected for gross and microscopic evaluations of organ toxicity. No signs of morbidity or mortality were observed. Single intravenous injections of 15-40 mg/kg BP1001 produced no drug-related lesions in examined organs. Reduction in the WBC count was observed at two weeks post-injection of 30 and 40 mg oligo/kg. Recovery of WBC counts was observed at six weeks post-injection at 30 mg oligo/kg. Group average WBC count was not fully recovered at six weeks in animals receiving 40 mg oligo/kg, but was not statistically different than control (Tani, 2007).

2. Multiple-dose Toxicity Study in Mice

In a multiple dose toxicity study of BP1001 in mice, 24 ICR mice (an outbred strain of mice from the Institute for Cancer Research; 5 female/group, 3 male/group) were assigned a non-injected control group (Group I) and two treatment groups (Groups to receive 15 and 25 mg oligo/kg intravenously via the tail vein daily for five consecutive days. Animals were observed daily and blood was collected for hematology and clinical chemistry evaluations at two and six weeks post-injection. Animals were sacrificed following blood collection at six weeks post-injection and tissues collected for gross and microscopic evaluations of organ toxicity. No signs of morbidity or mortality were observed. Multiple intravenous injections of 15-25 mg/kg BP1001 produced no drug-related lesions in examined organs. Reduction in WBC counts was observed at two weeks post-injection in treated groups, which persisted at six weeks post-injection. Differential WBC counts showed specific populations of WBCs in treated animals were not different from control (Tani, 2007).

3. Multiple-Dose Toxicity Studies in Rabbits

The potential toxicity of a twice weekly intravenously (slow bolus) administered BP1001 in Dutch Belted rabbits was conducted. BP1001 was administered over a 28-day period followed by a 2-week recovery phase. The study design was as shown in Table 2.

TABLE 2

Rabbit toxicity study design

| Group Number | Group Designation | Dosage Level (mg/kg) | Dosage Concentration (mg/ml) | Dosage Volume (mL/kg) | Number of Animals* Males | Number of Animals* Females |
|---|---|---|---|---|---|---|
| 1 | Low-dose | 3.75 | 2.5 | 1.5 | 9 | 9 |
| 2 | Mid-dose | 5.00 | 2.5 | 2.0 | 9 | 9 |
| 3 | High-dose | 7.50 | 2.5 | 3.0 | 9 | 9 |

*From each group, 3 male and 3 female rabbits were euthanized on Study Days 4, 29, and 42.

Doses were administered on Study Days 1, 3, 8, 10, 15, 17, 22, and 24. The first day of dosing on the study was designated as Study Day 1. The doses were given at approximately the same time each day. Individual dose volumes were calculated based on the most recently recorded body weight for each animal. Study Day 1 dose levels were calculated on a pretest body weight. Based on this study design, there were no apparent toxicological changes in clinical observations, body weights, bone marrow cytology, clinical pathology, organ weights, or microscopic findings. There were three gross observations recorded at necropsy. A Group 1, Study Day 4 male (#8939) and a Group 2, Study Day 42 female (#8968) had a gross observation of a small gall bladder. A Group 1, Study Day 29 female (#8944) had a gross observation of dark foci involving all lobes of the lung. These non-dose-dependent findings were apparently not related to the administration of BP1001. Based on this study design, there was no apparent toxicity of a twice weekly intravenously (slow bolus) administration of 3.75, 5.00, or 7.50 mg/kg BP1001 in clinical observations, body weights, bone marrow cytology, clinical pathology, organ weights, or microscopic findings. In addition, results showed that when BP1001 was administered to rabbits, there were no observed effects on coagulation parameters.

D. Ames Mutagenicity Study

BP1001 was tested in an Ames mutagenicity study. Sodium chloride (0.9%) was added to vials of BP1001 containing 5 mg of Grb2 oligonucleotide. The sample was tested against five strains of *Salmonella* in various concentrations in the presence and absence of the S-9 enzyme activation system. The sample was not mutagenic to the strains tested.

E. In vitro Mammalian Chromosome Aberration Test (CHO cells)

BP1001 was tested in the chromosome aberration assay using CHO cells in both the absence and presence of an Aroclor-induced S9 activation system. A preliminary toxicity test was performed to establish the dose range for the chromosome aberration assay. The chromosome aberration assay was used to evaluate the clastogenic potential of the BP1001. Based on the findings of this study, BP1001 was concluded to be negative for the induction of structural and numerical chromosome aberrations in CHO cells in both the non-activated and the S9-activated test systems.

V. Clinical Trials of BP1001 in Humans

A BP1001 phase I study was conducted in two parts: (A) BP1001 dose escalation and (B) BP1001 with concurrent low-dose cytarabine (LDAC) dose expansion. For dose escalation (Part A), a standard "3+3" design was used in which successive cohorts of 3 or more patients with hematologic malignancies were treated at escalating doses from 5 to 135 mg/m$^2$ of BP1001 until a maximum tolerated dose (MTD) was identified. For the dose expansion portion of the study (Part B), two successive subsets of patients with AML were treated with BP1001 at the MTD (or highest tested dose [HTD]) and one level below the MTD (or HTD) in combination with a fixed dose of LDAC to further characterize safety and biological effect, as well as identify the recommended phase 2 dose. Both parts of the study employed an open-label, sequential, dose-escalation design to assess safety, tolerability and toxicity, pharmacokinetics (PK), tumor response, and anti-leukemic activity. A total of 39 patients were treated in the study: AML (n=30), CML-BP (n=5), and MDS (n=4). Of 39 patients, 27 were evaluable; 12 failed completion of a full cycle due to disease progression and were replaced per protocol. Only one patient on 5 mg/m$^2$ experienced a dose-limiting toxicity (DLT), grade 3 mucositis and hand-foot syndrome, while on high-dose hydroxyurea for proliferative CML-BP. The study medication could not be ruled out as a contributing factor, so this event was reported as a DLT. Upon expansion to six patients, no other patient developed a DLT. No other drug related toxicity has been observed in any of the patients treated. A MTD was not identified. The HTD for BP1001 is 90 mg/m$^2$.

Among the 27 evaluable patients, a median of one cycle was administered (1-5): four received two cycles, three received three cycles, four received five cycles, and all others received one cycle. Among the 21 evaluable patients on single agent cohorts (Part A), 10 experienced ≥50% reduction in peripheral or bone marrow blasts; two had improvement of leukemia cutis; six had transient decline in blasts. Among the six evaluable patients on BP1001+LDAC combination therapy (Part B), three achieved complete remission (CR) and two achieved partial remission (PR).

A. Grb2 Biomarker Studies

Flow cytometry was used to determine the levels of Grb2 and pErk proteins in the circulating leukemia cells of patients who were on BP1001 single agent therapy, and were reported as median fluorescent intensity (MFI). MFI of Grb2 and pErk during treatment were compared to those at baseline. On the last measured sample (end of treatment or cycle 1 day 22), BP1001 decreased ≥25% Grb2 levels in 10 out of 12 samples, and ≥25% pErk levels in 7 out of 12 samples. The average decrease in Grb2 levels was 49% (range: 28% to 91%) and in pErk levels was 52% (range: 27% to 91%).

B. Pharmacokinetics Studies

Pharmacokinetic (PK) analysis was performed on plasma samples collected from refractory/relapsed patients diagnosed with AML receiving BP1001 (60 mg/m$^2$)+LDAC or receiving BP1001 (90 mg/m$^2$)+LDAC. In both cohorts, $T_{max}$ was 1 h post administration. $C_{max}$ of both doses was 82 ng/mL. However, the plasma half-life of BP1001 was longer for the 60 mg/m$^2$ dose than the 90 mg/m$^2$ dose (29.6±8.1 h versus 11.8±5.4 h). The clearance rate of BP1001 was lower for the 60 mg/m$^2$ dose than the 90 mg/m$^2$ dose (133±24 L/h versus 205±70 L/h). These results suggest that the 60 mg/m$^2$ BP1001 dose may be more favorable than the 90 mg/m$^2$ dose.

VI. Lipids and Liposomes

"Liposomes" is used herein to mean lipid-containing vesicles having a lipid bilayer, as well as other lipid carrier particles that can entrap or incorporate antisense oligonucleotides. As such, liposome is a generic term encompassing a variety of unilamellar, multilamellar, and multivesicular lipid vehicles formed by the generation of enclosed lipid bilayers or aggregates. In addition, liposomes may have an undefined lamellar structure. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as non-uniform aggregates of lipid molecules.

Liposomes are a form of nanoparticles that are carriers for delivering a variety of drugs into a diseased tissue. Optimal liposome size depends on the target tissue. In tumor tissue, the vasculature is discontinuous, and pore sizes vary from 100 to 780 nm (Siwak et al., 2002). By comparison, pore size in normal vascular endothelium is <2 nm in most tissues, and 6 nm in post-capillary venules. Negatively charged liposomes are thought to be more rapidly removed from circulation than neutral or positively charged liposomes; however, recent studies have indicated that the type of negatively charged lipid affects the rate of liposome uptake by the reticulo-endothelial system (RES). For example, liposomes containing negatively charged lipids that are not sterically shielded (phosphatidylserine, phosphatidic acid, and phosphatidylglycerol) are cleared more rapidly than neutral liposomes. Interestingly, cationic liposomes (1,2-dioleoyl-3-trimethylammonium-propane [DOTAP]) and cationic-liposome-DNA complexes are more avidly bound and internalized by endothelial cells of angiogenic blood vessels via endocytosis than anionic, neutral, or sterically stabilized neutral liposomes (Thurston et al., 1998; Krasnici et al., 2003). Cationic liposomes may not be ideal delivery vehicles for tumor cells because surface interactions with the tumor cells create an electrostatically derived binding-site barrier effect, inhibiting further association of the delivery systems with tumor spheroids (Kostarelos et al., 2004). However, neutral liposomes appear to have better intratumoral penetration. Toxicity with specific liposomal preparations has also been a concern. Cationic liposomes elicit dose-dependent toxicity and pulmonary inflammation by promoting release of reactive oxygen intermediates, and this effect is more pronounced with multivalent cationic liposomes than monovalent cationic liposomes, such as DOTAP (Dokka et al., 2000). Neutral and negative liposomes do not appear to exhibit lung toxicity (Guitierrez-Puente et al., 1999). Cationic liposomes, while efficiently taking up nucleic acids, have had limited success for in vivo gene down-regulation, perhaps because of their stable intracellular nature and resultant failure to release nucleic acid contents. Lipids with neutral charge or lipid compositions with a neutralized charge, e.g., 1,2-dioleoyl-sn-glycero-3-phosphocholine (DOPC), are used herein because of the neutral properties and success in delivering antisense oligonucleotides in vivo.

The present invention provides methods and compositions for associating an oligonucleotide, such as an antisense oligonucleotide, with a lipid and/or liposome. The oligonucleotide may be incorporated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The liposome or liposome/oligonucleotide-associated compositions provided herein are not limited to any particular structure in solution. For example, they may be present in a bilayer structure, as micelles, or with a "collapsed" structure. They may also simply be interspersed in a solution, possibly forming aggregates that are not uniform in either size or shape.

A. Lipids

Lipids are fatty substances that may be naturally occurring or synthetic. For example, lipids include the fatty droplets that naturally occur in the cytoplasm as well as the class of compounds that are well known to those of skill in the art that contain long-chain aliphatic hydrocarbons and their derivatives, such as fatty acids, alcohols, amines, amino alcohols, and aldehydes. An example is the lipid 1,2-dioleoyl-sn-glycero-3-phosphocholine (DOPC).

Lipid compositions of the present invention may comprise phospholipids. In certain embodiments, a single kind or type of phospholipid may be used in the creation of lipid compositions, such as liposomes. In other embodiments, more than one kind or type of phospholipid may be used.

Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), dilinoleoylphosphatidylcholine, 1,2-diarachidoyl-sn-glycero-3-phosphocholine ("DAPC"), 1,2-dieicosenoyl-sn-glycero-3-phosphocholine ("DEPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), palmitoyloeoyl phosphatidylcholine ("POPC"), 1-oleoyl-2-palmitoyl phosphatidylcholine ("OPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), dioleoylphosphatidylglycerol ("DOPG"), dimyristoyl phosphatidic acid ("DMPA"), dipalmitoyl phosphatidic acid ("DPPA"), distearoyl phosphatidic acid ("DSPA"), dioleoyl phosphatidic acid ("DOPA"), dimyristoyl phosphatidylethanolamine ("DMPE"), dipalmitoyl phosphatidylethanolamine ("DPPE"), distearoylphophatidylethanolamine ("DSPE"), dioleoylphosphatidylethanolamine ("DOPE"), palmitoyloeoyl phosphatidyletlianolamine ("POPE"), dimyristoyl phosphatidylserine ("DMPS"), dipalmitoyl phosphatidylserine ("DPPS"), brain phosphatidylserine ("BPS"), distearoyl sphingomyelin ("DSSP"), brain sphingomyelin ("BSP"), dipalmitoyl sphingomyelin ("DPSP"), lysophosphatidylcholine, and lysophosphatidylethanolamine.

Phospholipids include, for example, phosphatidylcholines, phosphatidylglycerols, and phosphatidylethanolamines; because phosphatidylethanolamines and phosphatidylcholines are non-charged under physiological conditions (i.e., at about pH 7), these compounds may be particularly useful for generating neutral liposomes. In certain embodiments, the phospholipid DOPC is used to produce non-charged liposomes or lipid compositions. In certain embodiments, a lipid that is not a phospholipid (e.g., a cholesterol) can also be used Phospholipids may be from natural or synthetic sources. However, phospholipids from natural sources, such as egg or soybean phosphatidylcholine, brain phosphatidic acid, brain or plant phosphatidylinositol, heart cardiolipin, and plant or bacterial phosphatidylethanolamine, are not used in certain embodiments as the primary phosphatide (i.e., constituting 50% or more of the total phosphatide composition) because this may result in instability and leakiness of the resulting liposomes.

B. Neutral Liposomes

"Neutral liposomes or lipid composition" or "non-charged liposomes or lipid composition," as used herein, are defined as liposomes or lipid compositions having one or more lipids that yield an essentially-neutral net charge (substantially non-charged). In certain embodiments, neutral liposomes or lipid compositions may include mostly lipids and/or phospholipids that are themselves neutral. In certain embodiments, amphipathic lipids may be incorporated into or used to generate neutral liposomes or lipid compositions. For example, a neutral liposome may be generated by combining positively and negatively charged lipids so that those charges substantially cancel one another, thereby yielding an essentially-neutral net charge. By "essentially neutral" or "essentially non-charged," it is meant that few, if any, lipids within a given population (e.g., a population of liposomes) include a charge that is not canceled by an opposite charge of another component (e.g., fewer than 10% of components include a non-canceled charge, more preferably fewer than 5%, and most preferably fewer than 1%). In certain embodiments of the present invention, a composition may be prepared wherein the lipid component of the composition is essentially neutral but is not in the form of liposomes.

The size of the liposomes varies depending on the method of synthesis. A liposome suspended in an aqueous solution is generally in the shape of a spherical vesicle, and may have one or more concentric layers of lipid bilayer molecules. Each layer consists of a parallel array of molecules represented by the formula XY, wherein X is a hydrophilic moiety and Y is a hydrophobic moiety. In aqueous suspension, the concentric layers are arranged such that the hydrophilic moieties tend to remain in contact with an aqueous phase and the hydrophobic regions tend to self-associate. For example, when aqueous phases are present within the liposome, the lipid molecules may form a bilayer, known as a lamella, of the arrangement XY-YX. Aggregates of lipids may form when the hydrophilic and hydrophobic parts of more than one lipid molecule become associated with each other. The size and shape of these aggregates will depend upon many different variables, such as the nature of the solvent and the presence of other compounds in the solution.

Liposomes within the scope of the present invention can be prepared in accordance with known laboratory techniques, such as, for example, the method of Bangham et al. (1965), the contents of which are incorporated herein by reference; the method of Gregoriadis (1979), the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

In certain embodiments, a neutral liposome may be used to deliver an oligonucleotide, such as an antisense oligonucleotide. The neutral liposome may contain a single species of oligonucleotide directed to the suppression of translation of a single gene, or the neutral liposome may contain multiple species of oligonucleotides that are directed to the suppression of translation of multiple genes. Further, the neutral liposome may also contain a chemotherapeutic in addition to the oligonucleotide; thus, in certain embodiments, a chemotherapeutic and an oligonucleotide may be delivered to a cell (e.g., a cancerous cell in a human subject) in the same or separate compositions.

Dried lipids or lyophilized liposomes may be dehydrated and reconstituted at an appropriate concentration with a suitable solvent (e.g., DPBS or Hepes buffer). The mixture may then be vigorously shaken in a vortex mixer. The liposomes may be resuspended at an appropriate total phospholipid concentration (e.g., about 10-200 mM). Unencapsulated oligonucleotide may be removed by centrifugation at 29,000 g and the liposomal pellets washed. Alternatively, the unencapsulated oligonucleotides may be removed by dialyzing against an excess of solvent. The amount of oligonucleotide encapsulated can be determined in accordance with standard methods.

VII. Inhibition of Gene Expression

An inhibitory oligonucleotide can inhibit the transcription or translation of a gene in a cell. An oligonucleotide may be from 5 to 50 or more nucleotides long, and in certain embodiments from 7 to 30 nucleotides long. In certain embodiments, the oligonucleotide may be 7, 8, 9, 10, 11, 12, 13, 14, 15, 16, 17, 18, 19, 20, 21, 22, 23, 24, 25, 26, 27, 28, 29, or 30 nucleotides long. The oligonucleotide may comprise a nucleic acid and/or a nucleic acid analog. Typically, an inhibitory oligonucleotide will inhibit the translation of a single gene within a cell; however, in certain embodiments, an inhibitory oligonucleotide may inhibit the translation of more than one gene within a cell.

Within an oligonucleotide, the components of the oligonucleotide need not be of the same type or homogenous throughout (e.g., an oligonucleotide may comprise a nucleotide and a nucleic acid or nucleotide analog). In certain embodiments of the present invention, the oligonucleotide may comprise only a single nucleic acid or nucleic acid analog. The inhibitory oligonucleotide may comprise 5, 6, 7, 8, 9, 10, 11, 12, 13, 14, 15, 16, 17, 18, 19, 20, 25, 30 or more contiguous nucleobases, including all ranges therebetween, that hybridize with a complementary nucleic acid to form a double-stranded structure.

VIII. Nucleic Acids

The present invention provides methods and compositions for the delivery of an oligonucleotide via neutral liposomes. Because an oligonucleotide is composed of a nucleic acid, methods relating to nucleic acids (e.g., production of a nucleic acid, modification of a nucleic acid, etc.) may also be used with regard to an oligonucleotide.

The term "nucleic acid" is well known in the art. A "nucleic acid" as used herein generally refers to a molecule (i.e., a strand) of DNA, RNA, or a derivative or analog thereof, comprising a nucleobase. These definitions refer to a single-stranded or double-stranded nucleic acid. Double-stranded nucleic acids may be formed by fully complementary binding; however, in some embodiments, a double-stranded nucleic acid may be formed by partial or substantial complementary binding. As used herein, a single-stranded nucleic acid may be denoted by the prefix "ss" and a double-stranded nucleic acid by the prefix "ds."

A. Nucleobases

As used herein a "nucleobase" refers to a heterocyclic base, such as, for example, a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds (i.e., "anneal" or "hybridize") with at least one naturally occurring nucleobase in a manner that may substitute for naturally occurring nucleobase pairing (e.g., the hydrogen bonding between A and T, G and C, and A and U). A nucleobase may be comprised in a nucleoside or nucleotide, using any chemical or natural synthesis method described herein or known to one of ordinary skill in the art.

"Purine" and/or "pyrimidine" nucleobase(s) encompass naturally occurring purine and/or pyrimidine nucleobases and also derivative(s) and analog(s) thereof, including but not limited to, a purine or pyrimidine substituted by one or more of an alkyl, carboxyalkyl, amino, hydroxyl, halogen (i.e., fluoro, chloro, bromo, or iodo), thiol, or alkylthiol moiety. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothyline, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Purine and pyrimidine derivatives or analogs include, but are not limited to (abbreviation/modified base description): ac4c/4-acetylcytidine, Mam5s2u/5-methoxyaminomethyl-2-thiouridine, Chm5u/5-(carboxyhydroxylmethyl) uridine, Man q/Beta, D-mannosylqueosine, Cm/2'-O-methylcytidine, Mcm5 s2u/5-methoxycarbonylmethyl-2-thiouridine, Cmnm5s2u/5-carboxymethylamino-methyl-2-thioridine, Mcm5u/5-methoxycarbonylmethyluridine, Cmnm5u/5-carboxymethylaminomethyluridine, Mo5u/5-methoxyuridine, D/Dihydrouridine, Ms2i6a, 2-methylthio-N6-isopentenyladenosine, Fm/2'-O-methylpseudouridine, Ms2t6a/N-49-beta-D-ribofuranosyl-2-methylthiopurine-6-yl)carbamoyl) threonine, Gal q/Beta,D-galactosylqueosine, Mt6a/N-49-beta-D-ribofuranosylpurine-6-yl)N-methyl-carbamoyl) threonine, Gm/2'-O-methylguanosine, Mv/Uridine-5-oxyacetic acid methylester, I/Inosine, o5u/Uridine-5-oxyacetic acid (v), I6a/N6-isopentenyladenosine, Osyw/Wybutoxosine, m1a/1-methyladenosine, P/Pseudouridine, m1f/1-methylpseudouridine, Q/Queosine, m1g/1-methylguanosine, s2c/2-thiocytidine, m1I/1-methylinosine, s2t/5-methyl-2-thiouridine, m22g/2,2-dimethylguanosine, s2u/2-thiouridine, m2a/2-methyladenosine, s4u/4-thiouridine, m2g/2-methylguanosine, T/5-methyluridine, m3c/3-methylcytidine, t6a/N-((9-beta-D-ribofuranosylpurine-6-yl)carbamoyl)threonine, m5c/5-methylcytidine, Tm/2'-O-methyl-5-methyluridine, m6a/N6-methyladenosine, Um/2'-O-methyluridine, m7g/7-methylguanosine, Yw/Wybutosine, Mam5u/5-methylaminomethyluridine, or X/3-(3-amino-3-carboxypropyl)uridine, (acp3)u.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom, in the sugar ring. As used herein, a "moiety" generally refers to a smaller chemical or molecular component of a larger chemical or molecular structure.

Different types of covalent attachment(s) of a nucleobase to a nucleobase linker moiety are known in the art. By way of non-limiting example, a nucleoside comprising a purine (i.e., A or G) or a 7-deazapurine nucleobase typically comprises a covalent attachment of the 9 position of the purine or 7-deazapurine to a 1'-position of a 5-carbon sugar. In another non-limiting example, a nucleoside comprising a pyrimidine nucleobase (i.e., C, T, or U) typically comprises a covalent attachment of the 1 position of the pyrimidine to a 1'-position of a 5-carbon sugar (Kornberg and Baker, 1992).

C. Nucleotides

As used herein, a "nucleotide" refers to a nucleoside further comprising a "backbone linkage." A backbone linkage generally covalently attaches a nucleotide to another molecule comprising a nucleotide, or to another nucleotide to form a nucleic acid. The "backbone linkage" in naturally occurring nucleotides typically comprises a phosphate moiety (e.g., a phosphodiester backbone linkage), which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphate moiety.

D. Nucleic Acid Analogs

A nucleic acid may comprise, or be composed entirely of, a derivative or analog of a nucleobase, a nucleobase linker moiety, and/or backbone linkage that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. Nucleobase, nucleoside, and nucleotide analogs or derivatives are well known in the art.

Non-limiting examples of nucleosides, nucleotides, or nucleic acids comprising 5-carbon sugar and/or backbone linkage derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' backbone linkages and ribonucleotides with 2'-5' backbone linkages; U.S. Pat. No. 5,714,606 which describes a modified backbone linkage wherein a 3'-position oxygen of the backbone linkage is replaced by a carbon to enhance the nuclease resistance of nucleic acids; U.S. Pat. No. 5,672,697 which describes oligonucleotides containing one or more 5' methylene phosphonate backbone linkages that enhance nuclease resistance; U.S. Pat. Nos. 5,466,786 and 5,792,847 which describe the linkage of a substituent moiety that may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases, and hybridization to target RNA; U.S. Pat. No. 5,470,967 which describes oligonucleotides comprising at least one sulfamate or sulfamide backbone linkage that are useful as nucleic acid hybridization probes; U.S. Pat. Nos. 5,378,825, 5,777,092, 5,623,070, 5,610,289 and 5,602,240 which describe oligonucleotides with a three or four atom backbone linkage moiety replacing the phosphodiester backbone linkage used for improved nuclease resistance, cellular uptake, and regulating RNA expression; U.S. Pat. No. 5,858,988 which describes hydrophobic carrier agent attached to the 2'-O position of oligonucleotides to enhance their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofaranosyl nucleotides for enhanced nuclease resistance, binding affinity, and ability to activate RNase H; U.S. Pat. No. 5,708,154 which describes RNA linked to a DNA to form a DNA-RNA hybrid; U.S. Pat. No. 5,908,845 which describes polyether nucleic acids wherein one or more nucleobases are linked to chiral carbon atoms in a polyether backbone; U.S. Pat. Nos. 5,786,461, 5,891,625, 5,786,461, 5,773,571, 5,766,855, 5,736,336, 5,719,262, 5,714,331, 5,539,082, and WO 92/20702 which describe peptide nucleic acids (PNA or peptide-based nucleic acid analog; or PENAM) that generally comprise one or more nucleotides or nucleosides that comprise a nucleobase moiety, a nucleobase linker moiety that is not a 5-carbon sugar (e.g., aza nitrogen atoms, amido and/or ureido tethers), and/or a backbone linkage that is not a phosphate backbone linkage (e.g., aminoethylglycine, polyamide, polyethyl, polythioamide, polysulfinamide, or polysulfonamide backbone linkage); and U.S. Pat. No. 5,855,911 which describes the hydrophobic, nuclease resistant P-ethoxy backbone linkage.

Other modifications and uses of nucleic acid analogs are known in the art, and it is anticipated that these techniques and types of nucleic acid analogs may be used with the present invention.

E. Preparation of Nucleic Acids

A nucleic acid may be made by any technique known to one of ordinary skill in the art, such as chemical synthesis, enzymatic production or biological production. Non-limiting examples of a synthetic nucleic acid (e.g., a synthetic oligonucleotide) include a nucleic acid made by in vitro chemical synthesis using phosphotriester, phosphite, or phosphoramidite chemistry and solid phase techniques, such as described in EP 266,032, incorporated herein by reference, or by deoxynucleoside H-phosphonate intermediates as described by Froehler et al. (1986) and U.S. Pat. No. 5,705,629, each incorporated herein by reference. In the methods of the present invention, one or more species of oligonucleotide may be used. Various mechanisms of oligonucleotide synthesis have been disclosed in, for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

F. Purification of Nucleic Acids

A nucleic acid may be purified on polyacrylamide gels, cesium chloride centrifugation gradients, or by any other means known to one of ordinary skill in the art (see for example, Sambrook et al. (2001), incorporated herein by reference).

In certain embodiments, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, the bulk of cellular components or in vitro reaction components, such as, for example, macromolecules, such as lipids or proteins, small biological molecules, and the like.

G. Hybridization

As used herein, "hybridization," "hybridize(s)," or "capable of hybridizing" is understood to mean the forming of a double or triple stranded molecule or a molecule with partial double or triple stranded nature. The term "anneal" as used herein is synonymous with "hybridize."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride, or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suit a particular application.

IX. Method of Manufacturing Liposomal P-Ethoxy Antisense Drug Product

Antisense oligonucleotides (oligos) complementary to specific regions of a target mRNA have been used to inhibit the expression of endogenous genes. When the antisense oligonucleotides bind to a target mRNA, a DNA-RNA hybrid is formed. This hybrid formation inhibits the translation of the mRNA and, thus, the expression of the encoded protein. If the protein is essential for the survival of the cell, the inhibition of its expression may lead to cell death. Therefore, antisense oligonucleotides can be useful tools in anticancer and antiviral therapies.

The main obstacles in using antisense oligonucleotides to inhibit gene expression are cellular instability, low cellular uptake, and poor intercellular delivery. Natural phosphodiesters are not resistant to nuclease hydrolysis; thus high concentrations of antisense oligonucleotides are needed before any inhibitory effect is observed. Modified phosphodiester analogs, such as P-ethoxy, have been made to overcome this nuclease hydrolysis problem, but they have not provided a satisfactory solution to the problem.

The cellular uptake of antisense oligonucleotides is low. To solve this problem, physical techniques, such as calcium-phosphate precipitation, DEAE-dextran mediation, or electroporation, have been used to increase the cellular uptake of oligonucleotides. These techniques are difficult to reproduce and are inapplicable in vivo. Cationic lipids, such as Lipofectin, have also been used to deliver oligonucleotides. An electrostatic interaction is formed between the cationic lipids and the negatively charged oligonucleotides, which results in a complex that is then taken up by the target cells. Since these cationic lipids do not protect the oligonucleotides from nuclease digestion and are harmful to the cell membrane, they are only useful in delivering the nuclease-resistant phosphorothioates, but not the nuclease-cleavable phosphodiesters.

Another modified phosphodiester analog that has been prepared is P-ethoxy. The P-ethoxy antisense backbone does not have an adverse effect on bleeding and complement activation, which are some of the toxicities that have been reported for other antisense analogs. The modifications of P-ethoxy oligonucleotides are made in the phosphate backbone so that the modification will not interfere with the binding of these oligonucleotides to a target mRNA. P-ethoxy oligonucleotides are made by adding an ethyl group to the non-bridging oxygen atom of the phosphate backbone, thus rendering these oligonucleotides uncharged compounds. In spite of their resistance to nucleases, the cellular uptake and intracellular delivery of P-ethoxy oligonucleotides is poor because upon internalization, these oligonucleotides remain sequestered inside the endosomal/lysosomal vacuoles, impeding their access to target mRNA.

A. P-Ethoxy Antisense Drug Product

The liposomal P-ethoxy antisense drug product is composed of two cGMP products, both of which have a FDA-required Certificate of Analysis with FDA-approved release criteria. The raw materials, solvents, and final drug product are described herein. When manufactured, the drug product is a lyophilized crystal or powder of amber or white color that comprises the following materials: oligonucleotide (e.g., P-ethoxy antisense drug substance), neutral lipids (e.g., DOPC), and surfactant (e.g., polysorbate 20). In preparation for administration to a patient, normal saline is added to the vial, at which time liposomes are formed with the P-ethoxy antisense incorporated into the interior.

B. P-Ethoxy Antisense Drug Substance

Specific physical properties (e.g., solubility and hydrophobicity, which then affect drug product solubility in saline, incorporation of oligo into liposomes, and liposome particle size) of the finished product can be defined using a pre-determined P-ethoxy and phosphodiester amidite raw material mix during production of the P-ethoxy antisense drug substance. While loss of the P-ethoxy backbone group randomly occurs during oligonucleotide manufacturing resulting in phosphodiester bonds at those linkages, that loss may not generate the preferred ratio of P-ethoxy:phosphodiester backbone linkage within the oligonucleotide. In this case, the mix of P-ethoxy and phosphodiester amidite raw material supplements the expected value of P-ethoxy backbone deletions, thus generating an oligonucleotide with the desired ratio. Increasing the number of P-ethoxy molecules in the backbone of the oligonucleotide causes the molecule to be more hydrophobic (which results in larger liposome particles; Table 1), less polar, and less soluble (Table 2). Methods of testing the charge-neutral, hydrophobic P-ethoxy drug substance include mass spectrometry to determine the distribution of oligonucleotide lengths and assays to determine the solubility of drug substance, which for practical purposes for solubility is a visual inspection of the drug product reconstituted in saline. As the oligonucleotide becomes less soluble due to a greater number of P-ethoxy backbone linkages the reconstituted solution becomes whiter until particulates form as hydrophobicity becomes too high.

TABLE 1

Liposome Particle Size Variability with Antisense Backbone Composition

| | | Post-Manufacturing Backbone Ethyl Deletion | | Particle Size Characteristics: Cumulative Distribution Function | | |
|---|---|---|---|---|---|---|
| | Engineered | | | 90% | 50% | 300 nm |
| Experiment | Antisense Backbone | Principal Peak | Composite Deletion | Value (nm)** | Value (nm) | Value (%) |
| 1 | 3 amidite substitution | −6 | −5.67 | 2130 | 911 | 15.30 |
| 2 | 3 amidite substitution | −6 | −5.67 | 2420 | 1004 | 15.50 |
| 3 | 3 amidite substitution | −6 | −6.12 | 3682 | 943 | 15.50 |
| 4 | 3 amidite substitution | −7 | −6.66 | 3805 | 978 | 14.60 |
| 5 | 100% P-ethoxy | −5 | −5.66 | 3924 | 976 | 16.00 |
| 6 | 2 amidite substitution | −5 | −5.32 | 4387 | 1888 | 11.60 |
| 7[a] | 100% P-ethoxy | −4 | −4.22 | 5057 | 1131 | 17.70 |
| 8 | 100% P-ethoxy | −4 | −4.52 | 5659 | 1359 | 10.00 |
| 9[b] | 100% P-ethoxy | −4 | −4.38 | 7571 | 1909 | 2.60 |
| 10[c] | 100% P-ethoxy | −4 | −4.38 | 7994 | 1653 | 14.40 |

**Drug product release criteria is for 90% of the liposome particles to be less than or equal to 5000 nm.
[a]This lot was discarded due to poor solubility; specifically, antisense particles in the reconstituted solution.
[b]This lot had lower DMSO and tBA volume with 2 mg antisense in a 20 mL vial, which added an additional component to liposome enlargement.
[c]This lot was not released because it failed the particle size release spec.

TABLE 2

Liposome Particle Solubility with Antisense Backbone Composition

| | | Post-Manufacturing Backbone Ethyl Deletion | | Drug Solubility | |
|---|---|---|---|---|---|
| Experiment | Engineered Antisense Backbone | Principal Peak | Composite Deletion | Visual Observation ** | Solubility Assessment |
| 1 | 3 amidite substitution | −6 | −5.67 | skim milk solution | good |
| 2 | 3 amidite substitution | −6 | −5.67 | skim milk solution | good |
| 3 | 3 amidite substitution | −6 | −6.12 | skim milk solution | good |
| 4 | 3 amidite substitution | −7 | −6.66 | skim milk solution | good |
| 5 | 100% P-ethoxy | −5 | −5.66 | skim milk solution | good |
| 6 | 2 amidite substitution | −5 | −5.32 | skim milk solution | good |
| 7 | 100% P-ethoxy | −4 | −4.52 | white solution | pass |
| 8[b] | 100% P-ethoxy | −4 | −4.38 | white solution | pass |
| 9[c] | 100% P-ethoxy | −4 | −4.38 | white solution | pass |
| 10[a] | 100% P-ethoxy | −4 | −4.22 | white solution particles | fail |

** If the drug product sample has particles the lot will be rejected
[a]This lot was discarded due to poor solubility; specifically, antisense particles in the reconstituted solution.
[b]This lot had lower DMSO and tBA volume with 2 mg antisense in a 20 mL vial, which added an additional component to liposome enlargement.
[c]This lot was not released because it failed the particle size release spec.

C. Formulation, Filtration, and Lyophilization of Liposomal P-Ethoxy Antisense Drug Product One gram (1 g) of pE oligos is dissolved in DMSO at a ratio of 10 mg oligonucleotide per 1 mL DMSO. Next, DOPC is added to tert-butyl alcohol at a ratio of 1 g DOPC per 1719 mL of tert-butyl alcohol. The oligo and DOPC are combined and mixed at a ratio of 1 g oligonucleotide per 2.67 g DOPC. Then, 20 mL of a 0.835% (v/v) solution of polysorbate 20 is added to the mixture resulting in a final concentration of 0.039 mg/mL. The solution is passed through a sterile filter prior to dispensing into glass vials for lyophilization.

The effect of the surfactant on liposome particle size was determined by titrating the amount of surfactant (Table 3). In the absence of polysorbate 20, only 2.8% of the particles had a diameter of 300 nm or less. In the presence of 1× polysorbate 20, 12.5% of the particles had a diameter of 300 nm or less. With the addition of 3×-10× polysorbate 20, around 20% of the particles had a diameter of 300 nm or less. Thus an increase in surfactant from 1× to 3× results in a decrease in particle size.

TABLE 3

Liposome Particle Size Variability with Surfactant

| | | Particle Size Characteristics: Cumulative Distribution Function | | |
|---|---|---|---|---|
| Experiment | Amount of Surfactant | 50% Value | 90% Value ** | 300 nm Value |
| 1 | 0× | 5301 nm | 10719 nm | 2.8% |
| 2 | 1× | 1053 nm | 4054 nm | 12.5% |
| 3 | 3× | 785 nm | 2926 nm | 19.1% |
| 4 | 5× | 721 nm | 2691 nm | 21.9% |
| 5 | 10× | 734 nm | 2937 nm | 21.4% |

** Drug product release criteria is for 90% of the liposome particles to be less than or equal to 5000 nm.

D. Preparation of Liposomal P-Ethoxy Antisense Drug Product for Administration

The lyophilized preparation was hydrated with normal saline (0.9%/10 mM NaCl) at a final oligo concentration of 10-5000 μM. The liposomal-P-ethoxy oligos were mixed by hand shaking.

E. Methods of Testing Liposomal P-Ethoxy Antisense Drug Product

Visual Inspection of Manufactured Drug Product:

After manufacturing, a sample vial containing drug product is selected and visually inspected. The absence of liquid is mandatory, and then amber crystals at the bottom of the vial are acceptable, and increasing in acceptance to a white, flocculated powder or appearance, the best result. The white appearance indicates a better drying process, with a high surface area to mass ratio, which is very conducive to reconstitution for use.

Visual Inspection of Reconstituted Drug Ready for Patient IV:

Normal saline is added to a vial containing the manufactured Liposomal P-ethoxy Antisense Drug Product and shaken to reconstitute into a solution with the drug crystal or powder completely dissolved. Three main observations are made: 1) that the crystal or powder is completely dissolved, 2) there are no white clumps of undissolved material, and 3) the appearance is a milky white or skim milk appearance. The bluer the appearance of the reconstituted liquid, the better, as this signals a smaller liposome particle size that reflects light in the blue spectrum.

Mass Spectrometry:

Mass spectrometry (mass spec) is used to display the profile of the various masses in a sample. When P-ethoxy antisense material is produced, a mass spec is run on the sample. The result shows peaks of material present on a grid that has increasing mass on the "x" axis to the right, and relative mass abundance on the "y" axis increasing upward. The profile from a sample is analyzed to determine the relative quantity of P-ethoxy backbones in the P-ethoxy sample, recognizing that the profile of peaks represents (starting farthest to the right), full length material with all backbones comprised of the P-ethoxy linkage, the next peak moving left a full length with one backbone with a P-ethoxy deletion (and therefore, the ethyl being knocked off and the result being a normal phosphodiester backbone linkage), and continuing. The mass spec pattern shifted to the right represents a P-ethoxy sample having more P-ethoxy backbones, and therefore having the properties of being more hydrophobic and less soluble; and likewise, shifted to the left having the opposite effects. Inspection of the mass spec chart of a sample also can be used to determine if filtration during manufacturing produces any adverse effects on oligonucleotide composition present in the filtered drug product.

UV Testing:

Ultraviolent light testing is used to determine the mass of oligonucleotide present in a sample. Oligonucleotides absorb light in the 260 nanometer range. As a result, UV testing of the finished reconstituted drug product has come to be used as a method in determining the quantity of oligonucleotide drug substance in a vial of drug product. In terms of manufacturing development and innovations, UV testing was used to determine if there were problems experienced during filtration in manufacturing or poor solubility of the P-ethoxy antisense drug substance, resulting in less oligonucleotide in solution and therefore a lower UV reading. The method will be validated and likely become part of the final product release testing.

Liposome Particle Size:

A vial of finished drug product is reconstituted and tested for liposome particle size. The result is often a roughly normal distribution, having a central point, tails and average values or a roughly normal distribution of the majority of the particles and smaller, secondary peaks of the smaller liposomes particles resulting from second-order particle formation effects. It is important that liposome particles not be too large, as they may create adverse effects in patients (for example, create blood flow problems in smaller blood vessels in the lungs). As a result, the drug product release criteria include that particle size testing show that 90% of liposomes be 5 microns or less in size. In addition, smaller liposomes are preferred because they will have better uptake into cells, and secondly, smaller liposomes can penetrate vascular pores, thereby allowing the liposomes to penetrate inside tumors, increasing treatment effectiveness of a Liposomal P-ethoxy Antisense Drug Product.

X. Methods of Treatment

Certain aspects of the present invention provide methods of treating a cancer patient with an oligonucleotide-lipid complex (e.g., an oligonucleotide incorporated into a neutral liposome) that contains a nuclease-resistant inhibitory oligo that targets Grb2. Particularly, the oligonucleotide may have a sequence that allows for base pairing with a human nucleotide sequence at the translation initiation site of Grb2 and thus may inhibit the expression of Grb2. In some aspects, the methods further comprise administering a front line therapeutic to the patient, such as, for example, a tyrosine kinase inhibitor (e.g., imanitib, dasanitib, nilotinib, bosutinib, ponatinib, or bafetinib) or a cytidine analogue (e.g., decitabine, azacitidine, or cytarabine).

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of an oligonucleotide-lipid complex.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

Tumors for which the present treatment methods are useful include any malignant cell type, such as those found in a solid tumor, a hematological tumor, metastatic cancer, or non-metastatic cancer. Exemplary solid tumors can include, but are not limited to, a tumor of an organ selected from the group consisting of pancreas, colon, cecum, esophagus, gastrointestine, gum, liver, skin, stomach, testis, tongue, uterus, stomach, brain, head, neck, ovary, kidney, larynx, sarcoma, bone, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In a particular embodiment, the invention contemplates methods of using an oligonucleotide-lipid complex comprises contacting a population of diseased cells in vivo with a therapeutically effective amount of an oligonucleotide-lipid complex for a time period sufficient to inhibit or reverse disease. In one embodiment, the contacting in vivo is accomplished by administering, by intravenous, intraperitoneal, subcutaneous, or intratumoral injection, a therapeutically effective amount of a physiologically tolerable composition comprising an oligonucleotide-lipid complex of this invention to a patient. The oligonucleotide-lipid complex can be administered parenterally by injection or by gradual infusion over time.

Therapeutic compositions comprising oligonucleotide-lipid complex are conventionally administered intravenously or subcutaneously, such as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial and booster administration are also contemplated and are typified by an initial administration followed by repeated doses at one or more hour intervals by a subsequent injection or other administration. Exemplary multiple administrations are described herein and are particularly preferred to maintain continuously high serum and tissue levels of polypeptide. Alternatively, continuous intravenous infusion sufficient to maintain concentrations in the blood in the ranges specified for in vivo therapies are contemplated.

It is contemplated that a method the invention may call for administration of an oligonucleotide composition systemically or locally to treat disease, such as to inhibit tumor cell growth or to kill cancer cells in cancer patients with locally advanced or metastatic cancers. They can be administered intravenously, intrathecally, subcutaneously, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

A therapeutically effective amount of an oligonucleotide is a predetermined amount calculated to achieve the desired effect, i.e., to inhibit the proliferation of cancer cells. Thus, the dosage ranges for the administration of oligonucleotides of the invention are those large enough to produce the desired effect. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

A composition of the present invention is preferably administered to a patient parenterally, for example by intravenous, intraarterial, intramuscular, intralymphatic, intraperitoneal, subcutaneous, intrapleural, or intrathecal injection, or may be used ex vivo. Preferred dosages are between 5-90 mg/m$^2$. The administration is preferably repeated on a timed schedule until the cancer disappears or regresses, and may be in conjunction with other forms of therapy.

XI. Pharmaceutical Preparations

A pharmaceutical composition comprising the liposomes will usually include a sterile, pharmaceutically acceptable carrier or diluent, such as water or saline solution.

Where clinical application of a neutral lipid component (e.g., in the form of a liposome) containing an oligonucleotide is undertaken, it will generally be beneficial to prepare the lipid complex as a pharmaceutical composition appropriate for the intended application. This will typically entail preparing a pharmaceutical composition that is essentially free of pyrogens, as well as any other impurities that could be harmful to humans or animals. One may also employ appropriate buffers to render the complex stable and allow for uptake by target cells.

The phrases "pharmaceutical or pharmacologically acceptable" refers to molecular entities and compositions that do not produce an adverse, allergic or other untoward reaction when administered to an animal, such as a human, as appropriate. The preparation of a pharmaceutical composition that contains at least one non-charged lipid component comprising an oligonucleotide or additional active ingredient will be known to those of skill in the art in light of the present disclosure, as exemplified by Remington: The Science and Practice of Pharmacy, 21st, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is preferably formulated for administration to a human, although in certain embodiments it may be desirable to use a pharmaceutically acceptable carrier that is formulated for administration to a non-human animal but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise from about 1 microgram/kg/body weight, about microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 µg/kg/body weight to about 100 mg/kg/body weight, about 5 microgram/kg/body weight to about 500 milligram/kg/body weight, etc., can be administered.

An oligonucleotide of the present embodiments may be administered in a dose of 1, 2, 3, 4, 5, 6, 7, 8, 9, 10, 15, 20, 25, 30, 40, 50, 60, 70, 80, 90, 100 or more µg of nucleic acid per dose. Each dose may be in a volume of 1, 10, 50, 100, 200, 500, 1000 or more µl or ml.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention may be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses discussed above in association with its administration, i.e., the appropriate route and treatment regimen. The quantity to be administered, both according to number of treatments and unit dose, depends on the protection or effect desired.

Precise amounts of the therapeutic composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

XII. Combination Treatments

In certain embodiments, the methods of the present invention involve administration of an inhibitory oligonucleotide, or oligonucleotide capable of expressing an inhibitor of gene expression, in combination with a second or additional therapy. The methods and compositions including combination therapies enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve contacting the cells with both an inhibitor of gene expression and a second therapy, such as a tyrosine kinase inhibitor (e.g., imatinib, nilotinib, dasatinib, bosutinib, ponatinib, or bafetinib) or a cytidine analogue (e.g., decitabine, cytarabine, or azacitidine). A tissue, tumor, or cell can be contacted with one or more compositions or pharmacological formulation(s) including one or more of the agents (i.e., inhibitor of gene expression or an anti-cancer agent), or by contacting the tissue, tumor, and/or cell with two or more distinct compositions or formulations, wherein one composition provides 1) an inhibitory oligonucleotide; 2) an anti-cancer agent, or 3) both an inhibitory oligonucleotide and an anti-cancer agent. Also, it is contemplated that such a combination therapy can be used in conjunction with a chemotherapy, radiotherapy, surgical therapy, or immunotherapy.

An inhibitory oligonucleotide may be administered before, during, after or in various combinations relative to an anti-cancer treatment. The administrations may be in intervals ranging from concurrently to minutes to days to weeks. In embodiments where the inhibitory oligonucleotide is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the inhibitory oligonucleotide therapy and the anti-cancer therapy within about 12 to 24 or 72 h of each other and, more preferably, within about 6-12 h of each other. In some situations it may be desirable to extend the time period for treatment significantly where several days (2, 3, 4, 5, 6 or 7) to several weeks (1, 2, 3, 4, 5, 6, 7 or 8) lapse between respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed. For the example below an inhibitory oligonucleotide therapy is "A" and an anti-cancer therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/A/A | B/B/A/A | B/A/B/A | B/A/A/B | A/A/A/B | B/A/A/A |
| A/B/A/A | A/A/B/A | | | | |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy.

In specific aspects, it is contemplated that a standard therapy will include chemotherapy, radiotherapy, immunotherapy, surgical therapy or gene therapy and may be employed in combination with the inhibitor of gene expression therapy, anticancer therapy, or both the inhibitor of gene expression therapy and the anti-cancer therapy, as described herein.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (such as bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, decitabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylomithine (DMFO); tyrosine kinase inhibitors, such as imatinib, nilotinib, dasatinib, bosutinib, ponatinib, and bafetinib; retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

C. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

Another immunotherapy could also be used as part of a combined therapy with gene silencing therapy discussed above. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects. Moreover, antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy, e.g., TNF, IL-1, IL-2, p53 (Qin et al., 1998; Austin-Ward and Villaseca, 1998; U.S. Pat. Nos. 5,830,880 and 5,846,945) and monoclonal antibodies, e.g., anti-ganglioside GM2, anti-HER-2, anti-p185 (Pietras et al., 1998; Hanibuchi et al., 1998; U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989).

D. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

XIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Phase I Study of BP1001 (Liposomal Grb2 Antisense) in Patients with Hematologic Malignancies Essential to cancer cell signaling, the growth factor receptor bound protein-2 (Grb2) is utilized by oncogenic tyrosine kinases to activate Ras and ERK. BP1001 is a liposome-incorporated antisense that inhibits Grb2 expression. The study aimed to define safety, maximum tolerated dose (MTD), pharmacokinetics, and anti-leukemic activity of BP1001 in patients with hematologic malignancies.

BP1001 Drug Substance and Administration.

The sequence of Grb2 antisense oligo is: 5'-ATA TTT GGC GAT GGC TTC-3' (SEQ ID NO: 1), which targets codons 2-7 of the human grb2 mRNA. Grb2 antisense oligo, composed of P-ethoxy oligo modification, was manufactured by Nitto Denko Avecia, Inc. (8560 Reading Road, Cincinnati, Ohio 45215, USA). Grb2 antisense oligo was incorporated into 1,2-dioleoyl-3-phosphatidylcholine lipid (Avanti Polar Lipids, Alabaster, Ala., USA), via a lyophilization protocol. BP1001 was prepared as 5-mg drug powder and stored at 4° C. On the day of drug infusion, two mL of 0.9% normal saline were added to achieve a final BP1001 concentration of 2.5 mg/mL. Participants were administered 2 to 3-h intravenous (IV) infusions of BP1001 twice weekly (every 3 or 4 days) for 28 days. Participants could be given up to 6 cycles of treatment, if they continued to benefit from treatment.

Patient and Study Design.

The study was designed as a standard 3+3 dose escalation trial for the assessment of safety, pharmacokinetics and efficacy of BP1001 in adult patients diagnosed with refractory/relapsed Philadelphia chromosome positive CML or ALL, AML, or MDS. Cohorts of three patients were enrolled at each dose level. The initial dose of BP1001 was 5 mg/m$^2$ (Cohort 1). If one patient developed a grade 3 or higher toxicity, three more patients were accrued at that dose level. If two or more patients developed a grade 3 or higher toxicity, that dose level was deemed toxic. The maximum tolerated dose (MTD) was defined as the dose lower than the one producing dose-limiting toxicity in two or more patients. The toxicities were graded using the National Cancer Institute Common Terminology Criteria for Adverse Events (NCI CTCAE, version 3.0). If dose-limiting toxicity (DLT) was not observed, patients would be sequentially enrolled into Cohort 2 (10 mg/m$^2$), Cohort 3 (20 mg/m$^2$), Cohort 4 (40 mg/m$^2$), Cohort 5 (60 mg/m$^2$), or Cohort 6 (90 mg/m$^2$).

Upon completion of BP1001 single agent phase I cohorts 1-6, the safety and efficacy of the combination of BP1001 and low dose cytarabine (phase Ib) was studied. BP1001 was administered IV as 60 mg/m$^2$ (cohort 7) or 90 mg/m$^2$ (cohort 8). Patients were given three injections of BP1001 before being administered with 20 mg of low dose cytarabine (LDAC) subcutaneously, twice daily for 10 continuous days. This study was registered with ClinicalTrials.gov, number NCT01159028.

Peripheral Blood and Bone Marrow Assessments.

Peripheral blood assessments were done at baseline (within 14 days of study start), and on days 1, 8, 15, 22, at completion of cycle one, and as clinically indicated. Bone marrow assessments were done at baseline (within 14 days of study start), at completion of cycle one, cycle 2, and as clinically indicated. Baseline cytogenetics data were obtained before treatment. Molecular analysis was conducted to detect somatic mutations on the baseline bone marrow.

Flow Cytometry.

Peripheral blood was collected from patients in cohorts 3, 4, 5, and 6, before being dosed on Cycle 1 days 1, 8, 15 and 22, and Cycle 2 day 1. White blood cells were isolated from peripheral blood using BD Vacutainer CPT cell preparation tubes with sodium heparin (BD Dickinson), fixed and stored in −80° C. freezer. Flow cytometry was utilized to determine Grb2 and phosphorylated Erk1,2 (pErk) levels in CD33-expressing cells using a validated method (Flow Contract Site Laboratory, Bothell, Wash., USA).

Pharmacokinetic Sample Collection and Analysis.

Blood samples for measurement of Grb2 antisense oligo concentrations were collected from patients in cohorts 7 and 8, at predose, 1, 2, 4, 6, 8, 24, 72 h post start-of-infusion (SOI). Urine samples for measurement of BP1001 concentrations were also collected from patients in cohorts 7 and 8, at start of dose-4 h, 4-8 h postdose, and 8-24 h postdose. PK blood samples were processed to plasma and analyzed using a validated method (Charles River Laboratories, Montreal, Canada) with a lower limit of quantitation (LLOQ; 0.5 ng/mL). Urine samples were analyzed using a validated method (Charles River Laboratories, Montreal, Canada) with a LLOQ of 1.00 ng/mL.

PK parameters were estimated using Phoenix pharmacokinetic software (Certara). A non-compartmental approach consistent with the IV infusion route of administration was used for parameter estimation, using an estimated infusion time of 2.5 h. All parameters were generated from Grb2 antisense oligo individual concentrations in plasma from Day 1 of Cycle 1, whenever practical. The Cycle 1, Day 1 predose concentration values were <LLOQ and therefore the time zero value was assumed to be zero. Parameters were estimated using nominal sampling times relative to the start of infusion. The area under the concentration vs. time curve (AUC) was calculated using the linear trapezoidal method with linear interpolation. The slope of the terminal elimination phase was determined using log linear regression on the unweighted concentration data. Parameters relying on the determination of the terminal elimination phase were not reported if the coefficient of determination ($R^2$) was less than 0.800, or if the extrapolation of the AUC to infinity (% AUCextrap) represented more than 20% of the total area.

Parameters estimated from plasma were: $T_{max}$, the time after dosing at which the maximum observed concentration was observed; $C_{max}$, the maximum observed concentration measured after dosing; $T_{1/2}$, apparent terminal elimination half-life; $AUC_{(0-24)}$, AUC from the dosing to 24 h post administration; $AUC_{(0-t)}$, AUC from dosing to the time after dosing at which the last quantifiable concentration was observed; $AUC_{(0-inf)}$, estimated AUC from dosing to infinity; CL, apparent clearance rate of Grb2 antisense oligo; Vz, apparent volume of distribution of Grb2 antisense oligo.

Urine parameter estimation was done using Microsoft Excel. All parameters were generated from Grb2 antisense oligo individual concentrations in urine from Day 1 of Cycle 1. Reported parameters were: Total U, cumulative amount of Grb2 antisense oligo excreted in urine over the entire sampling period; CLr, renal clearance relative to plasma; percent recovered, relative amount of Grb2 antisense oligo excreted in the urine compared to the total drug administered.

Statistical Analysis.

PK analysis as well as table and graph generation were generated by Phoenix version 1.4. Descriptive statistics (N, arithmetic mean, standard deviation) for appropriate grouping and sorting variables were generated using Phoenix version 1.4, and Microsoft Excel 2007.

Study Objectives.

The primary objectives of the BP1001 phase I study were to determine the toxicity and tolerance of escalating doses of BP1001 as a single agent therapy; determine the maximum tolerated dose (MTD) of BP1001; and determine the toxicity and tolerance of BP101 in combination with low-dose cytarabine (Ara-C; Phase Ib). The secondary objectives of the BP1001 phase I study were to determine the optimal biologically active dose (OBAD; defined as 50% reduction in Grb2 expression in circulating leukemia cells); determine in vivo pharmacokinetics of BP1001; and evaluate tumor response.

Inclusion and Exclusion Criteria.

Both parts of the study employed an open-label, sequential, dose-escalation design to assess safety, tolerability and toxicity, PK, tumor response, and anti-leukemic activity. Inclusion criteria were being at least 18 years old; having refractory or replaced AML, Ph+ CML, ALL, or MDS; being off anti-cancer therapy for at least two weeks prior to study entry (with the exception of hydroxyurea or anagrelide (24 h), TKI 95 d), and interferon (2 wks)); having adequate hepatic and renal functions (ALT<2×ULN, serum creatinine <2×ULN, serum bilirub <2×ULN); and having an ECOG performance of 0-2. Exclusion criteria were having serious intercurrent medical illnesses that would interfere with the ability of the patient to carry out the treatment program; and receiving another investigations product within the longer of 14 days or 5 half-lives of the previous product.

Patient Characteristics.

A total of 39 patients was enrolled in the study: 13 patients (cohort 1), 6 patients (cohort 2), 3 patients (cohort 3), 3 patients (cohort 4), 3 patients (cohort 5), 4 patients (cohort 6), 4 patients (cohort 7) and 3 patients (cohort 8). Five patients were diagnosed with CML blast phase, 30 patients with AML, and 4 patients with MDS (Table 3). Patients' median age was 66, ranging between 32 to 89 years of age. Twenty-seven were male patients and twelve were female patients. Prior to enrollment, patients had received a median of four regimens. Their median performance status was 1. The median peripheral blood blasts count was 15%, ranging between 0 to 96%. As expected, these patients had diverse cytogenetics, which included: t(9; 22) (n=7), diploid (n=12), complex (n=10), miscellaneous (n=13). Two patients had t(9; 22)-positive CML and complex cytogenetics, while one patient had t(9; 22)-positive AML.

Adverse Events in Evaluable Patients.

Of the 39 patients, 27 patients were evaluable. Twelve patients failed completion of a full cycle due to disease progression and were replaced per protocol (Table 4). Among the 27 evaluable patients, 21 patients were on BP1001 single agent therapy while 6 patients were on BP1001+LDAC combination therapy. As shown in Table 8, the evaluable patients had diverse molecular abnormalities in their leukemias, which included ASXL1 (n=1), BCR-ABL (n=2; including T315I in 1), CEBPA (n=4), DNMT3A (n=1), FLT-ITD (n=2), IDH1/2 (n=3), JAK2 (n=2), NOTCH1 (n=1), NPM1 (n=2), NRAS (n=2), TET2 (n=2), TP53 (n=2). Characteristics of the enrolled patients is provided in Table 3.

Only one patient on 5 mg/m² experienced a dose-limiting toxicity (DLT), grade 3 mucositis and hand-foot syndrome, while on high-dose hydroxyurea for proliferative CML-BP. The study medication could not be ruled out as a contributing factor, so this event was reported as a DLT. Upon expansion to 6 patients, no other patient developed a DLT. No other drug related toxicity has been observed in any of the patients treated. A MTD was not identified. The HTD for BP1001 is 90 mg/m².

TABLE 3

| Enrolled patient characteristics | | | |
|---|---|---|---|
| Characteristics | All patients (n = 39)[a] | Phase I (n = 32)[a] | Phase 1b (n = 7)[a] |
| Median age (years) | 66 (32-89) | 63 (32-89) | 72 (69-85) |
| Gender | | | |
| Male | 27 | 22 | 5 |
| Female | 12 | 10 | 2 |
| Number of prior regimens | 4 (1-8) | 4 (1-8) | 1 (1-4) |

TABLE 3-continued

| Enrolled patient characteristics | | | |
|---|---|---|---|
| Characteristics | All patients (n = 39)[a] | Phase I (n = 32)[a] | Phase 1b (n = 7)[a] |
| Diagnosis at study entry | | | |
| AML | 30 | 24 | 6 |
| CML (blast phase) | 5 | 4 | 1 |
| MDS | 4 | 4 | 0 |
| Performance status | 1 (0-2) | | |
| Median WBC (×10⁶ mL) | 3 (0.2-40) | | |
| Median peripheral blasts (%) | 15 (0-96) | | |
| Median hemoglobin (g/mL) | 9 (8-11) | | |
| Median platelets (×10⁶ mL) | 21 (4-155) | | |
| Cytogenetics | | | |
| t(9; 22) | 7[b] | 6[b] | 1 |
| Diploid | 12 | 8 | 4 |
| Miscellaneous | 13 | 12 | 1 |
| Complex | 10 | 9 | 1 |

[a]Data are n (range) or % (range) unless otherwise stated.
[b]Two patients had t(9; 22)-positive CML and complex cytogenetics, while one patient had t(9; 22)-positive AML.

TABLE 4

| Patients and dose per cohort | | | | |
|---|---|---|---|---|
| Cohort | BP1001 (mg/m²) | Ara-C | Number Treated | Number Evaluable |
| 1 | 5 | No | 13 | 6 |
| 2 | 10 | No | 6 | 3 |
| 3 | 20 | No | 3 | 3 |
| 4 | 40 | No | 3 | 3 |
| 5 | 60 | No | 3 | 3 |
| 6 | 90 | No | 4 | 3 |
| 7 | 60 | Yes | 4 | 3 |
| 8 | 90 | Yes | 3 | 3 |

Pharmacokinetics of Grb2 Antisense Oligo.

Figure 1:
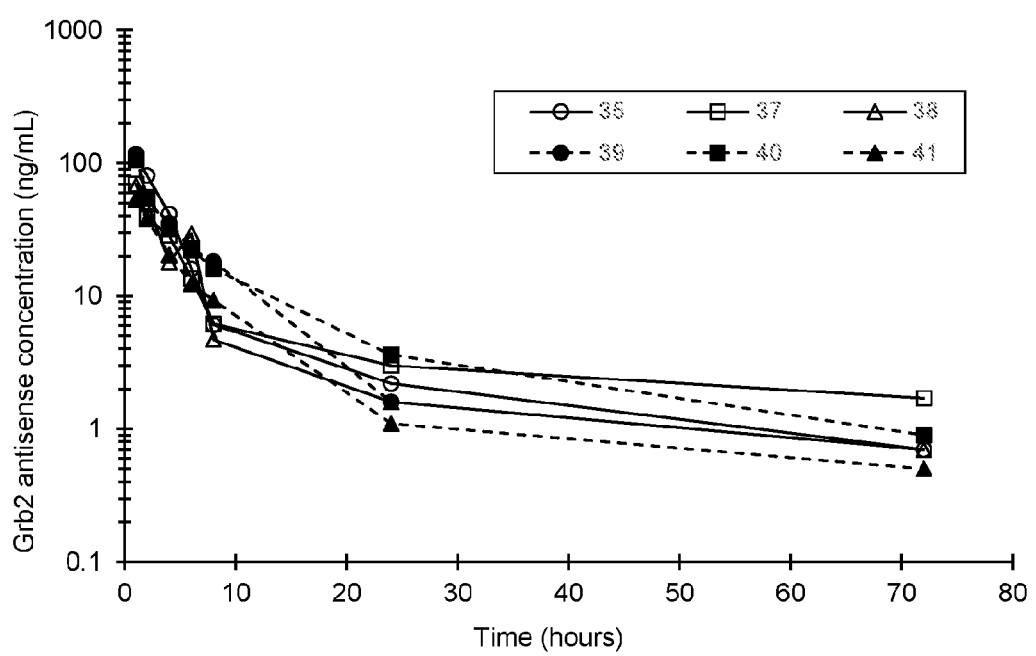
FIG. 1. Concentration of Grb2 antisense oligo in patients' plasma. BP1001 levels in plasma declined bi-exponentially. Solid lines were dosed at 60 mg/m$^2$; dashed lines were dosed at 90 mg/m$^2$.

The lower limit of quantitation (LLOQ) of Grb2 antisense oligo concentration in plasma is 0.50 ng/mL. There was no quantifiable Grb2 antisense oligo concentration at the pre-study time point. The levels of Grb2 antisense oligo in plasma declined bi-exponentially (FIG. 1). Maximal concentration of Grb2 antisense oligo in plasma was observed 1 h post infusion (FIG. 1). At 72 h post infusion, the levels of Grb2 antisense oligo in plasma were below the LLOQ or slightly above it (FIG. 1). The plasma t112 of Grb2 antisense oligo in plasma ranged from 22.2 to 37.7 h for the 60 mg/m² dose, and from 4.64 to 14.2 h for the 90 mg/m² dose (Table 5). The $C_{max}$, $AUC_{(0-24)}$, $AUC_{(0-t)}$ and $AUC_{(0-inf)}$ were similar for both dose levels, despite there was a 1.5-fold increase in dose from 60 to 90 mg/m² (Table 5). The Vz decreased by approximately 1.5-fold and the CL increased by approximately 1.5-fold for the dose increase from 60 to 90 mg/m² (Table 5).

TABLE 5

| BP 1001 plasma concentration following a single IV infusion of BP 1001 | | | | | | | | |
|---|---|---|---|---|---|---|---|---|
| Subject (cohort) | BP1001 (mg/m²) | $t_{1/2}$ (h) | $C_{max}$ (ng/mL) | $AUC_{0-24}$ (h · ng/mL) | $AUC_{0-t}$ (h · ng/mL) | $AUC_{0-inf}$ (h · ng/mL) | Vz (L) | CL (L/h) |
| 35 (7) | 60 | 22.2 | 110 | 419 | 490 | 513 | 3750 | 117 |
| 37 (7) | | 37.7 | 69 | 291 | 404 | 496 | 6570 | 121 |
| 38 (7) | | 25.9 | 68 | 294 | 349 | 375 | 5980 | 160 |
| Mean | | 29.6 | 82 | 335 | 414 | 461 | 5433 | 133 |
| SD | | 8.1 | 24 | 73 | 71 | 75 | 1487 | 24 |

TABLE 5-continued

BP 1001 plasma concentration following a single IV infusion of BP 1001

| Subject (cohort) | BP1001 (mg/m$^2$) | $t_{1/2}$ (h) | $C_{max}$ (ng/mL) | AUC$_{0-24}$ (h · ng/mL) | AUC$_{0-t}$ (h · ng/mL) | AUC$_{0-inf}$ (h · ng/mL) | Vz (L) | CL (L/h) |
|---|---|---|---|---|---|---|---|---|
| 39 (8) | 90 | 4.6 | 118 | 491 | 490 | 501 | 1200 | 180 |
| 40 (8) |  | 14.2 | 106 | 471 | 580 | 599 | 3070 | 150 |
| 41 (8) |  | 13.7 | 53 | 269 | 307 | 317 | 5600 | 284 |
| Mean |  | 11.8 | 82 | 410 | 459 | 472 | 3290 | 205 |
| SD |  | 5.4 | 24 | 122 | 139 | 14 | 2208 | 70 |

The amount of Grb2 antisense oligo recovered in the urine compared to the total dose administered ranged from 0.04 to 3.23% for the 60 mg/m$^2$ dose, and from 0.36 to 4.77% for the 90 mg/m$^2$ dose. Mean Grb2 antisense oligo urine concentrations were higher in the 90 mg/m$^2$ cohort than the 60 mg/m$^2$ cohort (Table 6).

TABLE 6

BP1001 urine concentration following a single IV infusion of BP1001

| Subject (cohort) | BP1001 (mg/m$^2$) | Total U (mg) | CLr from plasma (mL/h) | % recovered |
|---|---|---|---|---|
| 35 (7) | 60 | 1.49 | 4220 | 1.44 |
| 37 (7) |  | 0.06 | 195 | 0.04 |
| 38 (7) |  | 4.27 | 14500 | 3.23 |
| Mean |  | 1.94 | 6305 | 1.57 |
| SD |  | 2.14 | 7377 | 1.60 |
| 39 (8) | 90 | 4.27 | 8720 | 2.44 |
| 40 (8) |  | 8.34 | 17700 | 4.77 |
| 41 (8) |  | 0.46 | 8600 | 0.36 |
| Mean |  | 4.36 | 11673 | 2.52 |
| SD |  | 3.94 | 5220 | 2.21 |

BP1001 Decreased Grb2 and Phosphorylated Erk1,2 (pErk) Levels.

Flow cytometry was utilized to determine the levels of Grb2 and pErk proteins in the circulating leukemia cells of patients who were on BP1001 single agent therapy, and were reported as median fluorescent intensity (MFI). MFI of Grb2 and pErk during treatment were compared to those at baseline (Table 7). On the last measured sample (end of treatment or cycle 1 day 22), BP1001 decreased ≥25% Grb2 levels in 10 out of 12 samples, and ≥25% pErk levels in 7 out of 12 samples. The average decrease in Grb2 levels was 49% (range: 28% to 91%) and in pErk levels was 52% (range: 27% to 91%).

TABLE 7

Reduction in Grb2 and pErk levels following BP1001 administration

| Subject (cohort) | BP1001 (mg/m$^2$) | Grb2 decrease (%) (Day 15) | pErk decrease (%) (Day 15) | Grb2 decrease (%) (Day 22 or end-of-treatment) | pErk decrease (%) (Day 22 or end-of-treatment) |
|---|---|---|---|---|---|
| 22 (3) | 20 | 0 | 0 | 57 | 0 |
| 23 (3) | 20 | 0 | 3 | 28 | 45 |
| 24 (3) | 20 | 56 | 28 | 47 | 35 |
| 25 (4) | 40 | 63 | 82 | 54 | 91 |
| 26 (4) | 40 | 47 | 0 | 0 | 0 |
| 27 (4) | 40 | NS | NS | 34 | 27 |
| 28 (5) | 60 | 0 | 0 | 30 | 54 |
| 29 (5) | 60 | 57 | 51 | 65 | 0 |
| 30 (5) | 60 | 54 | 55 | 43 | 47 |
| 31 (6) | 90 | 0 | 0 | 0 | 0 |
| 32 (6) | 90 | 85 | 54 | 91 | 63 |
| 34 (6) | 90 | 63 | 42 | 40 | 0 |

NS = no sample collected

Anti-Leukemia Activity of BP1001.

BP1001, as a single agent therapy, decreased >50% peripheral blood blasts in 9 of 21 patients, and decreased >50% bone marrow blasts in 3 of 21 patients (Table 8). Per protocol, patients may receive BP1001 treatment for up to 6 months if they exhibited stable disease (i.e. less than a 50% increase in their WBC over the first 4 weeks of therapy), or had improvement of their disease. Four patients completed 2 cycles of treatment and three patients completed 5 cycles of treatment (Table 8). These seven patients had diverse cytogenetics and molecular abnormalities such as JAK2 and NRAS mutations (Table 8).

Figure 2:
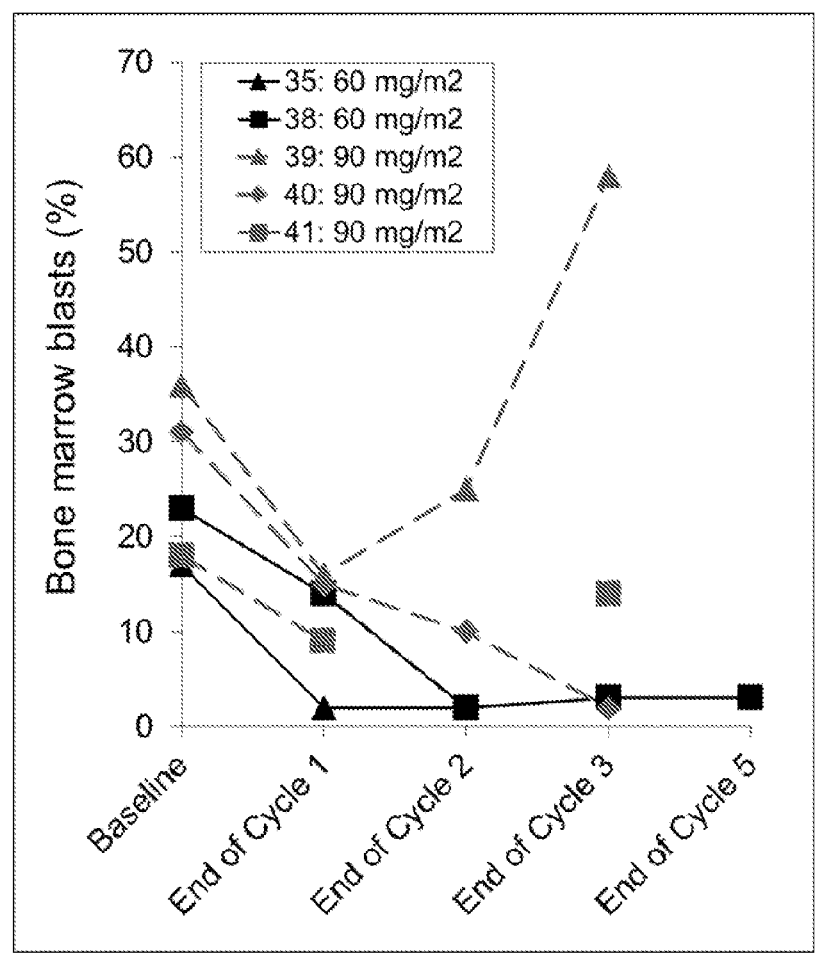
FIG. 2. BP1001+low dose Ara-C decreased bone marrow blasts in refractory/relapsed AML patients.

Among the six evaluable patients who were on BP1001+ LDAC combination therapy, three patients received 3 cycles of treatment and one patient received 5 cycles of treatment (Table 8). More importantly, three patients achieved complete remission (bone marrow blasts ≤5%) and two patients achieved partial remission (≥50% decrease in bone marrow blasts) (Table 8; FIG. 2).

TABLE 8

Hematologic experience of evaluable patients

| Subject | BP1001 (mg/m$^2$) | Ara-C | DX | Cyto-genetics | Molecular abnormalities | Peripheral blood blasts (%) Baseline | Peripheral blood blasts (%) Nadir | Peripheral blood blasts (%) Off-Rx | Bone marrow blasts (%) Baseline | Bone marrow blasts (%) Nadir | Bone marrow blasts (%) Off-Rx | Cycles completed |
|---|---|---|---|---|---|---|---|---|---|---|---|---|
| 1 | 5 | No | CML | 7q– complex | BCR-ABL T315I | 93 | 82 | 97 | 78 | ND | ND | <1 |
| 6* | 5 | No | AML | diploid | JAK2 | 15 | 2 | 5 | NA | ND | ND | 5 |
| 7 | 5 | No | MDS | 20 complex | Negative | 0 | 0 | 0 | 8 | 4 | 6 | 5 |

TABLE 8-continued

Hematologic experience of evaluable patients

| Subject | BP1001 (mg/m²) | Ara-C | DX | Cyto-genetics | Molecular abnormalities | Peripheral blood blasts (%) | | | Bone marrow blasts (%) | | | Cycles completed |
|---|---|---|---|---|---|---|---|---|---|---|---|---|
| | | | | | | Baseline | Nadir | Off-Rx | Baseline | Nadir | Off-Rx | |
| 10 | 5 | No | AML | diploid | Negative | 1 | 0 | 1 | 23 | 10 | 10 | 1 |
| 11 | 5 | No | CML | Ph+ complex | BCR-ABL Y253H, F317V | 24 | 7 | 50 | 11 | ND | ND | 1 |
| 14 | 5 | No | AML | diploid | RAS | 48 | 5 | 21 | 33 | ND | ND | 1 |
| 15 | 10 | No | AML | diploid | FLT-ITD, CEBPA | 54 | 31 | 72 | 85 | 76 | 76 | 1 |
| 20 | 10 | No | AML | diploid | Negative | 76 | 5 | 63 | 50 | None | 80 | 1 |
| 21 | 10 | No | AML | Misc | Negative | 71 | 43 | 74 | 40 | 38 | 38 | 2 |
| 22 | 20 | No | AML | Misc | NRAS | 1 | 0 | 1 | 8 | 3 | ND | 2 |
| 23 | 20 | No | MDS | 5q– | JAK2 V617F | NE | NE | NE | NE | NE | NE | 1** |
| 24 | 20 | No | MDS | –7 | Not Done | 0 | 0 | 0 | NE | NE | NE | 5 |
| 25 | 40 | No | AML | diploid | Negative | 10 | 3 | 19 | 25 | None | 36 | 2 |
| 26 | 40 | No | AML | Ph+ | FLT-ITD, CEBPA | 16 | None | 80 | 25 | None | 80 | 1 |
| 27 | 40 | No | AML | diploid | NPM1 exon 12 IDH1 R132H | 93 | None | 97 | 87 | 54 | ND | 1 |
| 28 | 60 | No | AML | Misc | CEBPA | 96 | 93 | 98 | 89 | 88 | 88 | 1 |
| 29 | 60 | No | AML | 5 and 7 complex | Negative | 35 | 7 | 24 | 28 | ND | ND | 1 |
| 30 | 60 | No | AML | Misc | IDH2 R140Q | 51 | 17 | 82 | 72 | None | 92 | 1 |
| 31 | 90 | No | AML | 8+ | Negative | 0 | 0 | 0 | 17 | None | 17 | 1 |
| 32 | 90 | No | AML | 7q– | NRAS | 2 | None | 42 | 24 | 22 | 22 | 2 |
| 34 | 90 | No | AML | 5q– | Negative | 5 | None | 92 | 66 | ND | ND | 1 |
| 35 | 60 | Yes | AML | diploid | Negative | 0 | 0 | 0 | 18 | 2 | 2 | 1 (CR) |
| 37 | 60 | Yes | AML | 5q– | TP53, NOTCH1 | 80 | 13 | 31 | 25 | 25 | ND | 1 |
| 38 | 60 | Yes | AML | diploid | NPM1, IDH2 | 4 | 0 | ND | 23 | 2 | 3 | 5 (CR) |
| 39 | 90 | Yes | AML | Misc | DNMT3A, TET2, TP53 | 70 | 0 | 52 | 36 | 15 | 58 | 3 (PR) |
| 40 | 90 | Yes | AML | diploid | Negative | 0 | 0 | 0 | 31 | 10 | 2 | 3 (CR) |
| 41 | 90 | Yes | AML | diploid | TET2, CEBPA, ASXL1 | 0 | 0 | 0 | 18 | 9 | 14 | 3 (PR) |

ND = Not done;
NE = BM not evaluable for differential or nadir due to insufficient sample;
None = no nadir or reduction in blasts
*Patient 6 was diagnosed with myelofibrosis with AML
**Patient 23 completed cycle 1 but withdrew from the study due to drug supply issues

Example 2—In Vitro Efficacy of BP1001 in Combination with Das

The clinical activity of BP1001 will be investigated in CML patients who are in accelerated or blast phase. The response of accelerated and blast phase patients to imatinib is poor or short-lived. These patients are often treated with other tyrosine kinase inhibitors, such as dasatinib, nilotinib, bosutinib, and ponatinib. Here, it was determined whether BP1001 could enhance the inhibitory effects of dasatinib, nilotinib, bosutinib, and ponatinib in CML cells.

Cell Culture.

BV173 and K562 cells are Bcr-Abl-positive cell lines derived from CML patients. They were obtained from CLS Cell Lines Service GmbH (Eppelheim, Germany) and cultured in RPMI medium supplemented with 10% heat-inactivated fetal bovine serum.

Chemicals.

The sequence of the Grb2 antisense oligo is: 5'-ATAT-TTGGCGATGGCTTC-3' (SEQ ID NO: 1). Grb2 antisense oligo was manufactured by Avecia (Cincinnati, Ohio, USA). BP1001 was prepared by Avanti Polar Lipids (Alabaster, Ala., USA) as described. In brief, Grb2 antisense oligo was mixed with dioleoylphosphatidylcholine lipids (Avanti Polar Lipids, Alabaster, Ala., USA), frozen and lyophilized. The lyophilizate was stored at 4° C. The day of experiment, BP1001 was hydrated with medium and added to cells at a final concentration of 0 to 120 µg/mL. Tyrosine kinase inhibitors, such as dasatinib, nilotinib, bosutinib and ponatinib, were purchased from Selleck Chemicals (Houston, Tex., USA) as 10 mM DMSO stock solutions.

Cell Viability Assays.

BV173 and K562 cells were seeded at 5 and 15×10³ cells/well, respectively, in 96-well plates in 0.1 mL of medium. Cells were incubated with BP1001 and/or tyrosine kinase inhibitors for 4 days. The viability of untreated and treated leukemia cells was measured by the CellTiter-Glo® Luminescent Cell Viability Assay (Promega, Madison, Wis., USA). The CellTiter-Glo® Luminescent Cell Viability Assay determines the number of viable cells by quantitating the presence of ATP, an indicator of metabolically active cells.

Cell Cycle Analysis.

After incubated with BP1001 and/or tyrosine kinase inhibitors for 4 days, BV173 cells were harvested and washed with phosphate buffered saline (PBS). Cells were then fixed and permeabilized for 1 h at 4° C. with 1×Fixation/Permeabilization buffer (Ebioscience, San Diego, Calif., USA). After permeabilization, cells were washed and incubated with 7-aminoactinomycin D (7-AAD, Biolegend, San Diego, Calif., USA) in the dark at 4° C. for about 30 min. Flow cytometric data acquisition was acquired using BD FACSDiva™ software (BD Biosciences, San Jose, Calif., USA). The flow cytometer was set to collect 20,000 events. Relative percentages in the different cell cycle phases (sub-G1, G1, S, G2/M) were reported.

BP1001 Pretreatment Enhanced Dasatinib Inhibition.

It was first determined whether BP1001 could enhance dasatinib inhibition in CML cell lines. To delineate whether the timing of BP1001 addition could affect dasatinib activity, BP1001 and dasatinib co-incubation was performed in different sequences: (1) BP1001 was added to cells 1 h before adding dasatinib (to mimic same day treatment); (2) BP1001 was added to cells 1 day after cells had been treated with dasatinib; (3) BP1001 was added to cells one day before cells were treated with dasatinib.

Co-Incubation Sequence (1): BP1001 and Dasatinib Added on the Same Day.

Figure 7A:
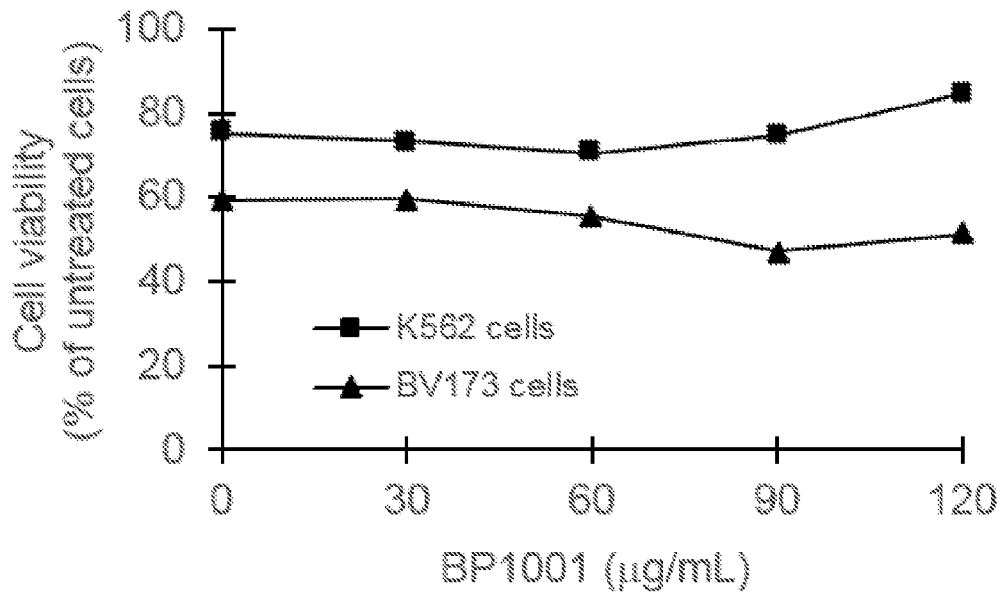
FIGS. 7A-C. Effect of timing and sequencing of BP1001 and dasatinib administration.

K562 and BV173 cells were incubated with BP1001 (0-120 µg/mL) for 1 h before being treated with 1 nM dasatinib. Four days later, growth inhibitory effects were determined. In the absence and presence of 120 µg/mL of BP1001, dasatinib decreased K562 viability by 25% and 15%, respectively (FIG. 7A). In the absence and presence of 120 µg/mL BP1001, dasatinib decreased BV173 viability by 40 and 49%, respectively (FIG. 7A). These data indicate that when CML cells were treated with BP1001 and dasatinib on the same day, BP1001 had minimal effects on dasatinib inhibition.

Co-Incubation Sequence (2): Dasatinib Added Before BP1001.

Figure 7B:
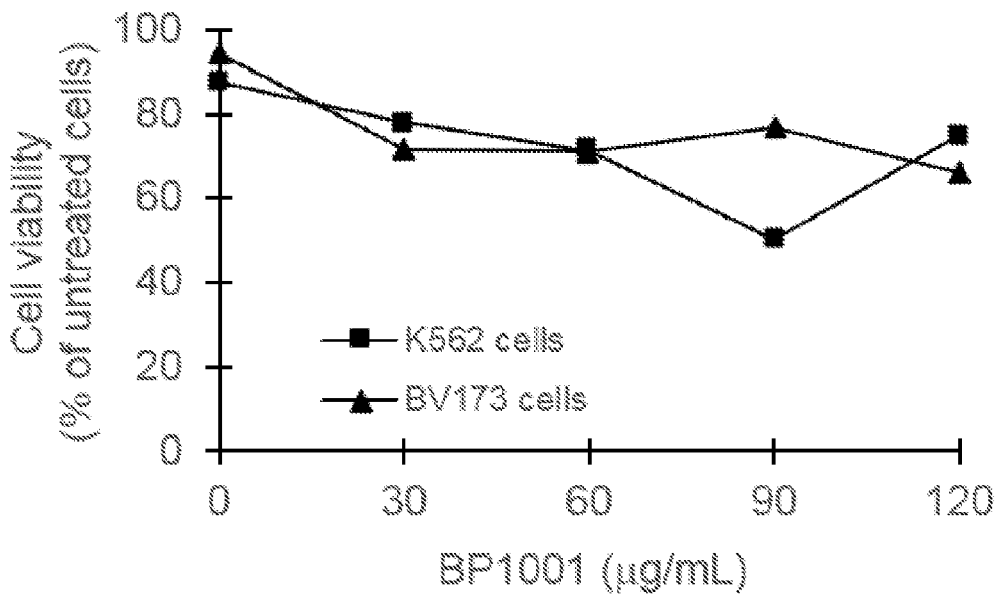

CML cell lines were treated with dasatinib for 1 day, followed by BP1001 treatment. Cell viability was determined 3 days later. Dasatinib decreased K562 viability by 12% (FIG. 7B). The addition of 190 µg/mL concentration of BP1001 decreased K562 viability to 50% (FIG. 7B). However when 120 µg/mL concentration of BP1001 was added to dasatinib, K562 viability decreased by 25% (FIG. 7B). Dasatinib decreased BV173 viability by 6% (FIG. 7B). The addition of 120 µg/mL BP1001 decreased BV173 viability by 34% (FIG. 7B). BP1001 added 1 day after dasatinib treatment further decreased BV173 viability. But it is not clear whether BP1001 added 1 day after dasatinib treatment could further decrease K562 viability.

Co-Incubation Sequence (3): BP1001 Added Before Dasatinib.

Figure 7C:
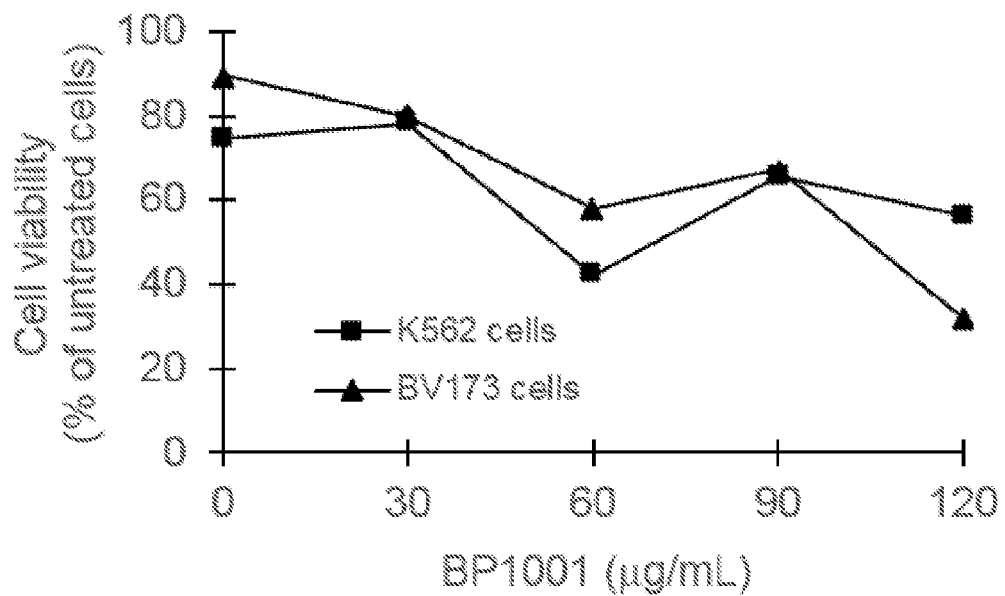
Figure 8A:
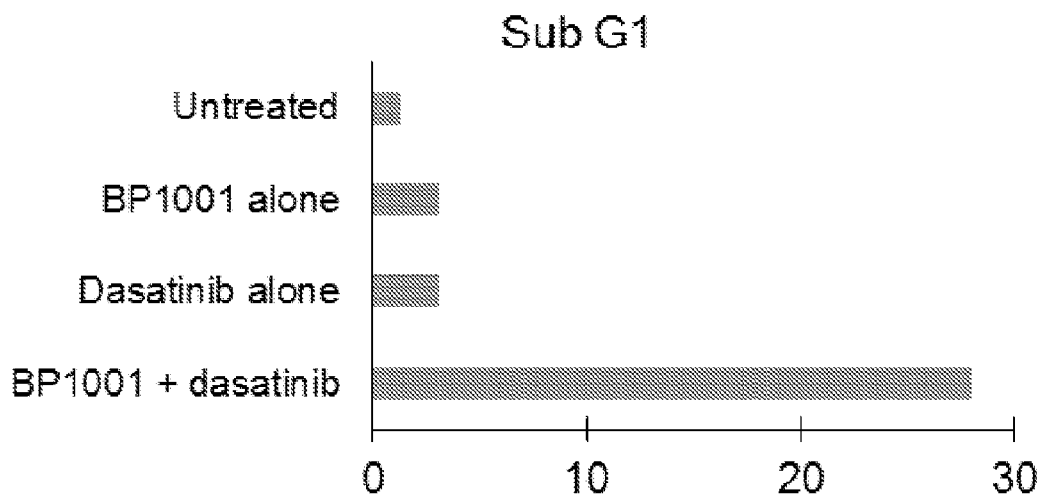
FIGS. 8A-D. BP1001 enhances dasatinib cell death induction.
Figure 8B:
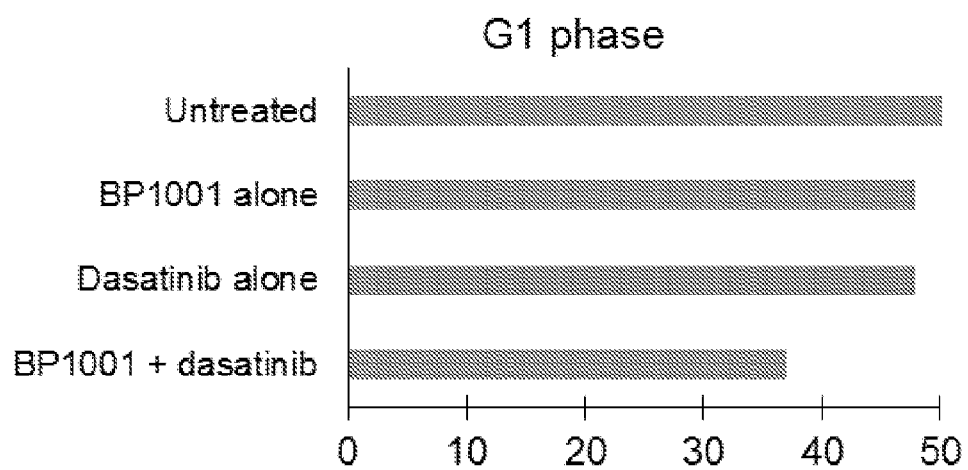
Figure 8C:
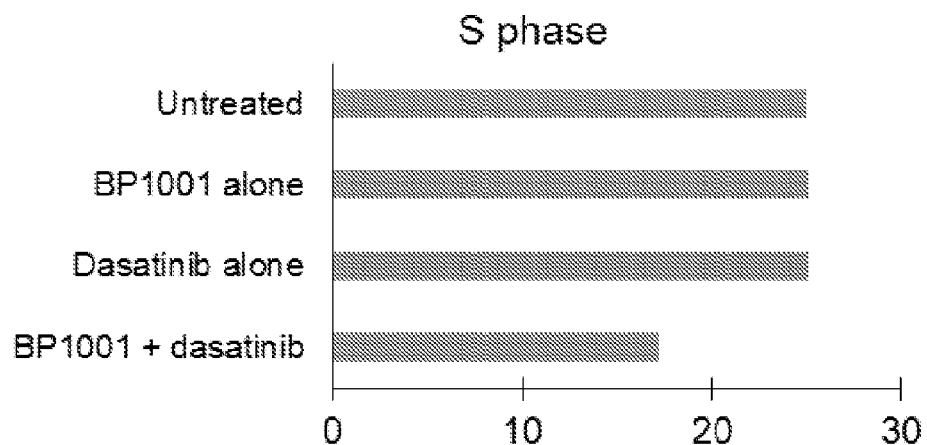
Figure 8D:
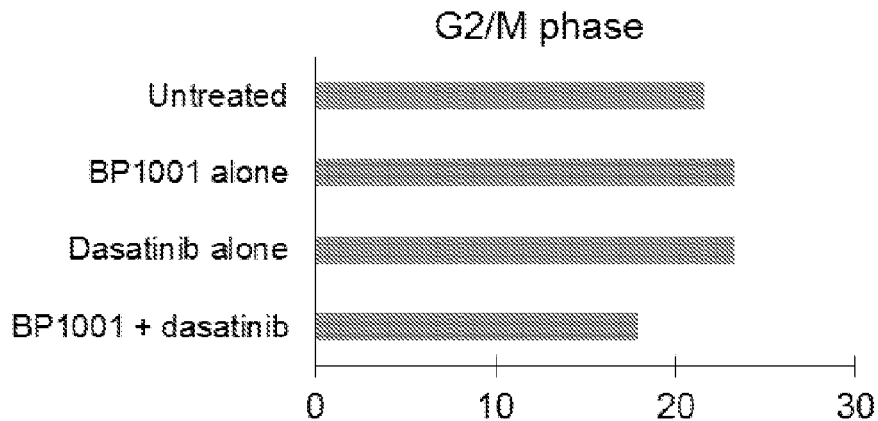

CML cell lines were incubated with BP1001 for 1 day before being treated with dasatinib. Dasatinib alone decreased K562 viability by 25% (FIG. 7C). When 120 µg/mL BP1001 was added to dasatinib, K562 viability was decreased by 44% (FIG. 7C). In the absence and presence of 120 µg/mL BP1001, dasatinib decreased BV173 viability by 10% and 68%, respectively (FIG. 7C). These data indicate that 1-day pretreatment of BP1001 enhanced dasatinib inhibition in both CML cell lines.

BP1001 Enhanced Dasatinib Cell Death Induction.

Next, we determined the mechanism by which BP1001 enhanced dasatinib inhibition. BV173 cells were incubated with BP1001 for 1 day, before being treated with dasatinib. Three days later, cells were harvested and processed for flow cytometry. The major mechanism of inhibition of the BP1001+dasatinib combination was cell death induction, as shown by the increase in percentages of cells in the sub-G1 phase (FIGS. 8A-D). The percentages of cells in sub-G1 phase upon being treated with BP1001, dasatinib and the combination were 3.1, 10.6 and 28.0, respectively (FIGS. 8A-D).

BP1001 Pretreatment Selectively Enhanced Dasatinib and Nilotinib Cell Death Induction.

Figure 3:
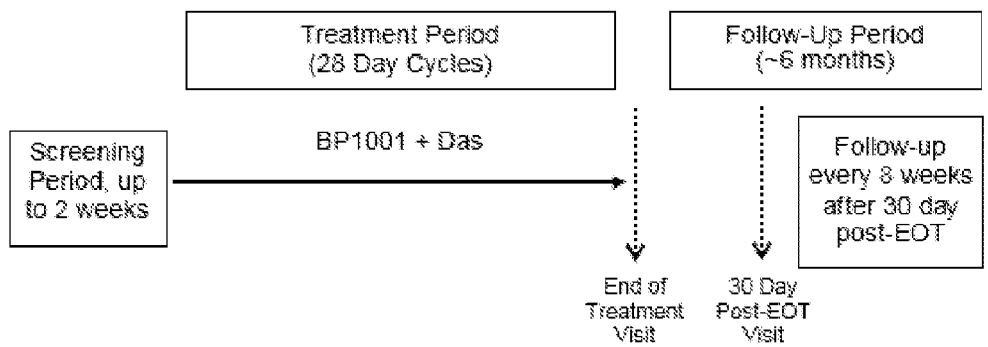
FIG. 3. Schematic of study design.
Figure 9A:
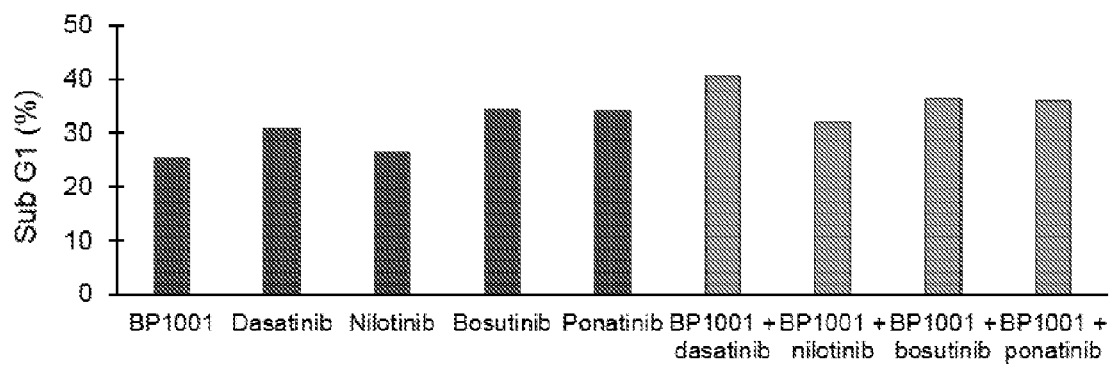
FIGS. 9A-B. BP1001 pretreatment enhances dasatinib and nilotinib cell death induction.

Flow cytometry was utilized to determine the effects of BP1001 pretreatment on nilotinib, bosutinib, and ponatinib. FIG. 3 showed that BP1001 pretreatment enhanced dasatinib and nilotinib inhibition. The percentages of cells in the sub-G1 phase were increased from 30.7 to 40.6 for dasatinib, and from 26.4 to 32 for nilotinib (FIG. 9A). However, BP1001 pretreatment did not affect bosutinib or ponatinib inhibition (FIG. 9A). The percentages of cells treated with bosutinib and the BP1001+bosutinib combination in the sub-G1 phase were 34.3 and 36.4, respectively, while for ponatinib and the BP1001+ponatinib combination were 34.0% and 36.0%, respectively (FIG. 9A). These data indicate that BP1001 pretreatment selectively enhanced dasatinib and nilotinib inhibition.

Figure 9B:
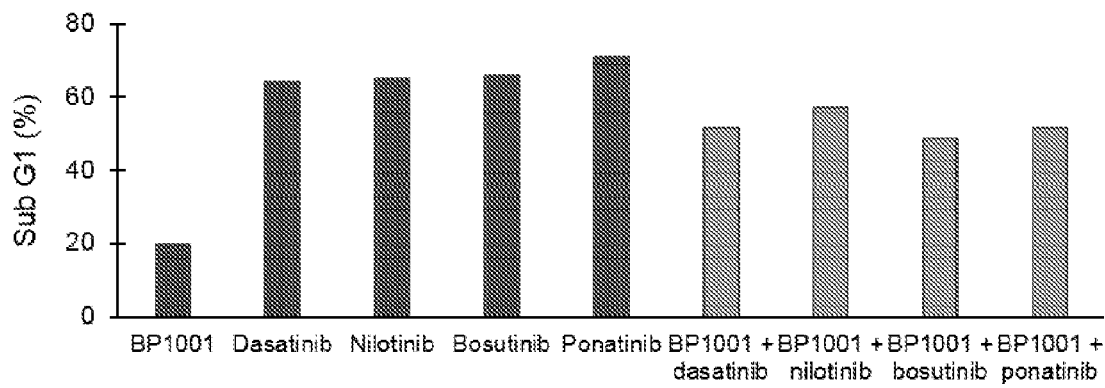

Interestingly, reduced cell death was observed when cells were treated with BP1001 after the tyrosine kinase inhibitors. The percentages of cells in the sub-G1 phase were decreased from 64.1 to 51.8 for dasatinib, from 65.0 to 57.1 for nilotinib, from 66.1 to 48.6 for bosutinib, and from 71.1 to 51.7 for ponatinib (FIG. 9B).

Example 3—a Phase Ib/IIa Clinical Trial to Evaluate the Safety, Pharmacokinetics, and Efficacy of BP1001 in Combination with Dasatinib (Das) in Patients with pH+ CML in Accelerated or Blast Phase Study Rationale.

The Phase Ib study will enroll participants with Ph+ CML in accelerated or blast phase. Participants will receive BP1001 plus Das. This is an open-label, single-arm clinical trial. Participants who are eligible to receive treatment in the Phase Ib study will receive BP1001 (60 mg/m$^2$ for cohort 1 or 90 mg/m$^2$ for cohort 2) and the same dose level of Das (140 mg). Once the dose has been identified for Phase IIa, all participants who are eligible to receive treatment in the Phase IIa will receive the same dose levels for both BP1001 and Das. There will be no randomization for this study.

Each treatment cycle will be 28 days. BP1001 will be administered over approximately 1 to 3 hours every 2 to 4 days (+/−1 day allowable window) beginning on Day 1 of the cycle for a total of eight administrations each treatment cycle. On or about Day 5 of the cycle, and no less than 24 h after completion of the second dose of BP1001, participants will initiate once daily oral dosing of 140 mg Das and will continue every day thereafter without interruption. Repeat cycles following this regimen will be scheduled every 4 weeks until progression, relapse, intolerance, participant has completed 6 cycles of treatment, or participant/Investigator requested discontinuation. When participants have completed the dosing portion of the study, they will be followed for approximately 6 months, or until death or study closure, whichever comes first.

Study Rationale: Dose Selection.

Preliminary data show that Grb2 down-regulation (and potential anti-leukemic benefit) can be attained in participants with BP1001 at HTD (90 mg/m$^2$) and at one level below the HTD (60 mg/m$^2$), and that safety/tolerability is not substantially different between these two doses. Based on this, the safety and tolerability of combining 60 or 90 mg/m$^2$ BP1001 with Das will be studied.

In the Phase Ib study, BP1001 will be administered intravenously (IV) twice weekly (every 2-4 days), with a +/−1 day window allowable, over approximately 1-3 hours for a total of eight doses given over a 28-day cycle. The starting dose will be 60 mg/m$^2$ with the first dose of BP1001 to be given starting on Day 1 of each 28-day cycle. No less than 24 h after completion of the second dose of BP1001, participants will initiate daily dosing of 140 mg Das and will continue every day thereafter without interruption. Dosing of Das may begin as early as Day 5 as long as it is initiated no less than 24 h after completion of the second dose of BP1001. Three patients will receive BP1001 at each dose level for 28 days in the absence of DLT. Dose escalation within this part of the study will proceed until DLT of grade 3 is detected.

The next cohort of patients will be entered on study once three patients on the prior cohort have completed 28 days of treatment, without evidence of DLT. Thereafter, dose escalation will proceed to 90 mg/m². If one patient experiences DLT, this cohort will be expanded with 3 additional patients. Any cohort where ≥2 of 3-6 patients treated experience DLT will be considered to have exceeded MTD and the immediate lower dose cohort will be selected for further study. All patients will be evaluated for toxicity at the end of treatment (28 days) using the NCI CTCAE Criteria. Repeat cycles following this regimen will be scheduled every 4 weeks until progression, relapse, intolerance, participant has completed 6 cycles of treatment, or participant/investigator requested discontinuation.

The Phase IIa treatment schedule will be identical to the Phase Ib study. However, all participants will be given the same doses of BP1001 (identified in the Phase Ib study) and 140 mg of Das.

Study Rationale: Study Design.

Efficacy and safety of BP1001 will be evaluated in conjunction with Das, a therapeutic regimen well established in treatment of Ph+ CML patients who are in accelerated or blast phase. Based on our preclinical studies, BP1001 in combination with Das is predicted to provide a benefit to CML patients in accelerated or blast phase, who typically do not respond to the front-line treatment, imatinib. The study design is presented graphically in FIG. 3.

This trial will utilize a single arm, open label design to assess the safety profile, pharmacokinetics, and efficacy of BP1001 in combination with Das. The Phase Ib study employs an open-label, sequential, dose-escalation design to assess safety, tolerability and toxicity, tumor response and anti-leukemic activity.

A standard "3+3" design will be used in which successive cohorts of patients with CML are treated with BP1001 at the maximally tolerated dose (MTD) or HTD if the MTD is not defined and 1 level below the MTD (or HTD) in combination with a fixed dose of Das to characterize safety and biological effect, as well as identify the recommended Phase IIa dose.

Three patients will receive BP1001 at each dose level for 28 days in the absence of DLT. The next cohort of patients will be entered on study once 3 patients on the prior cohort have completed 28 days of treatment, without evidence of DLT. Thereafter, dose escalation will proceed to 90 mg/m². If one patient experiences DLT, this cohort will be expanded with 3 additional patients. Any cohort where ≥2 of 3-6 patients treated experience DLT will be considered to have exceeded MTD and the immediate lower dose cohort will be selected for further study. All patients will be evaluated for toxicity at the end of treatment (28 days) using the NCI CTCAE Criteria.

Patients may receive extension of treatment. Repeat cycles following this regimen will be scheduled every 4 weeks until progression, relapse, intolerance, participant has completed 6 cycles of treatment, or participant/investigator requested discontinuation.

The Phase IIa study is an open-label, single-dose level study. All participants who are eligible to receive treatment on study will receive the same dose level for both BP1001 (the HTD or 1 level below the HTD) as determined by the Phase Ib study and Das (140 mg). There will be no randomization for this study.

The Phase IIa study will compare the efficacy of the BP1001 in combination with Das to historical response rates documented for Das alone, and will evaluate the pharmacokinetics of BP1001, when given alone or in combination with Das.

Approximately 40 evaluable participants will receive the combination of BP1001 with Das in Phase IIa as follows. Following verification of eligibility during the screening period, participants will receive their initial dose of BP1001. The dose will be identified in Phase Ib based on the safety and tolerability of combining BP1001 with Das. BP1001 will be given on C1D1 and every 2 to 4 days thereafter, for a total of 8 doses given over a 28-day cycle. On or about Day 5 of the cycle, and no less than 24 hours after completion of the second dose of BP1001, participants will initiate once daily oral dose of 140 mg Das and will continue every day thereafter without interruption.

Participants who have completed at least 3 cycles of treatment will be evaluated for their response. The target response rate is 35%. The Bayesian approach of Thall, Simon, Estey will be implemented for the futility monitoring. The following futility stopping rule will be applied in cohort size of 5, starting from the 5-th patient: prob{p(RR) >0.35}<0.03, where p(RR) denotes the response rate. That is, the trial will be stopped early due to futility, if during the study we determine that there is less than 3% chance that the RR is more than 35%.

The Bayesian approach will also be implemented for toxicity monitoring for patients enrolled, where toxicity is defined as any non-hematological toxicity determined to be a DLT which is at least possibly related to the treatment. The toxicity, denoted as TOX will be monitored by the Bayesian stopping boundaries calculated based on beta-binomial distributions. We assume as a priori, p(TOX)~beta (0.6, 1.4). The study will be stopped for toxicity if Pr(p(TOX)>0.30 data)>0.88. That is, we will stop the trial for new patient enrollment if at any time during the study we determine that there is more than 88% chance that the toxicity rate is more than 30%.

Patients may receive extension of treatment. Repeat cycles following this regimen will be scheduled every 4 weeks until progression, relapse, intolerance, participant has completed 6 cycles of treatment, or participant/investigator requested discontinuation.

Study Objectives. The primary objective of the Phase Ib study is to determine the dose-limiting toxicity (DLT) and maximal tolerated dose (MTD) of BP1001 in combination with Das. The primary objectives of the Phase IIa study are to assess the pharmacokinetics (PK) and efficacy of the combination of BP1001 and Das.

The following are secondary objectives of this study: to assess the safety of BP1001 in combination with Das; to determine whether the combination of BP1001 and Das provides greater efficacy (Hematologic Response, Cytogenetic Response or Molecular Response) than Das alone (by historical comparison); to evaluate the pharmacokinetics (PK) of BP1001 when given alone and in combination with Das; to assess overall survival, time to response, and duration of response.

The exploratory objective of this study will evaluate the correlation of treatment response with abl kinase domain mutations.

Study Population: Inclusion Criteria.

At the time of screening, participants must meet all of the following criteria to be considered eligible to participate in the study:

1. Adults ≥18 years of age
2. Females must be of non-childbearing potential, surgically sterile, postmenopausal, or practice adequate methods of contraception during the study and for 30 days after the last dose of study drug or Das
3. Males must agree to use an adequate method of contraception during the study and for at least 30 days after the last dose of study drug or Das
4. Histologically documented diagnosis of Ph+ CML, in accelerated or blast phase. Blast phase is defined as ≥30% blasts in peripheral blood or bone marrow, or presence of extramedullary disease, except for liver or spleen. One of the following parameters is required to meet criteria for accelerated CML:
   a. Blasts in Peripheral Blood or Bone Marrow ≥15%
   b. Promyelocytes and Blasts in Peripheral Blood or Bone Marrow ≥30%
   c. PB or BM basophils ≥20%
   d. Thrombocytopenia <100×10$^3$/ml, not resulting from therapy
   e. Cytogenetic clonal evolution
5. Adequate hepatic and renal functions as defined by:
   a. Aspartate transaminase (AST) and alanine transaminase (ALT) ≤2.5 times the upper limit of normal (ULN); and
   b. Total bilirubin ≤1.5 times ULN; and
   c. Estimated glomerular filtration rate (eGFR) of at least 50 ml/min; the Cockcroft Gault formula will be utilized to determine eGFR when blood urea nitrogen (BUN) and creatinine testing are performed at baseline. The combination of eGFR serum creatinine and BUN will be used to evaluate patient's renal function for safety assurance.
      (i) Cockcroft Gault equation: estimated creatinine clearance=[(140−age)×total body weight]/(serum creatinine×72)
      (ii) Multiply by 0.85 for females
6. Documented Eastern Cooperative Oncology Group (ECOG) performance status of 0, 1, or 2 (Table 9)
7. Recovered from the effects of any prior surgery, radiotherapy, or antineoplastic treatment (with the exception of alopecia)
8. Willing and able to provide written informed consent

TABLE 9

ECOG Performance Status

| Grade | ECOG |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| 2 | Ambulatory and capable of all self-care but unable to carry out any work activities. Up and about more than 50% of waking hours |
| 3 | Capable of only limited self-care, confined to bed or chair more than 50% of waking hours |
| 4 | Completely disabled. Cannot carry on any self-care. Totally confined to bed or chair |
| 5 | Dead |

Study Population: Exclusion Criteria.
At the time of screening, participants who meet any of the following criteria will be excluded from participating in the study:
1. Patients with T315I mutation will not be excluded, but their response will be analyzed separately
2. Another primary malignancy other than CML within the past 2 years except non-melanoma skin cancer, or carcinoma in situ of the cervix.
3. Known, active leptomeningeal leukemia requiring intrathecal therapy. NOTE: Patients with a history of CNS disease may be allowed to participate based on at least two consecutive documented, negative spinal fluid assessment prior to screening
4. Isolated extramedullary leukemia without also meeting bone marrow criteria for leukemia
5. Receipt of any anti-cancer therapy within 14 days of starting BP1001, with the exception of hydroxyurea or anagrelide, or TKI (within 2 days)
6. Uncontrolled active, untreated, or progressive infection
7. Receipt of any investigational agent within 14 days or 5 half-lives of starting BP1001
8. Females who are pregnant, test positive for pregnancy, or are breast-feeding during the screening period, or intend to become pregnant or breast-feed during the course of the study or within 30 days after last dose of study drug
9. Prior exposure to BP1001
10. Patients with a history of intolerance to Das or for whom Das might not be appropriate
11. Serious intercurrent medical or psychiatric illness which would interfere with the ability of the participant to complete the study
12. Active/chronic hepatitis B infection (based on positive surface antigen [HBsAg]), hepatitis C infection (based on positive antibody [HCV Ab]), or human immunodeficiency virus (HIV-1 or HIV-2, based on positive antibody)
13. Presence of concurrent conditions that may compromise the participant's ability to tolerate study treatment or interfere with any aspect of study conduct or interpretation of results. This includes, but is not limited to, unstable or uncontrolled angina, New York Heart Association (NYHA) class III or IV congestive heart failure, uncontrolled and sustained hypertension, clinically significant cardiac dysrhythmia or clinically significant ECG abnormality (e.g., QTcF >470 msec)
14. Within the past 6 months, has had any of the following: pleural effusion, myocardial infarction, unstable angina pectoris, coronary/peripheral artery bypass graft, cerebrovascular accident, or transient ischemic attack
15. Uncontrolled seizure disorder (i.e., seizures within the past 2 months)
16. Unable or unwilling to communicate or cooperate with the Investigator or follow the protocol for any reason Study Treatments: BP1001 Dose and Administration.
BP1001 is supplied as a sterile, preservative-free, white lyophilized powder for reconstitution for IV administration and is supplied in 20 mL vials. Each single use, 20-ml vial of BP1001 contains 5 mg of Grb2 oligonucleotide and 13.35 mg DOPC. Calculations for dosing are based on the Grb2 oligonucleotide. Each vial of BP1001 should be reconstituted with 2 mL of normal saline (0.9% sodium chloride) for injection to yield a concentration of 5.0 mg/2.0 mL (2.5 mg/mL) of BP1001. Reconstituted BP1001 is stable for approximately 6 hours after reconstitution; therefore, the IV infusion should be completed no longer than approximately 6 hours after reconstitution.
In the Phase Ib study, the dose of BP1001 to be used is 60 mg/m$^2$ (cohort 1) or 90 mg/m$^2$ (cohort 2). BP1001 will be administered as an IV infusion on days 1, 4, 8, 11, 15, 18, 22 and 25 (with +/−1 day window allowable) of each 28-Day cycle. For treatment Cycle 1, participants must receive both doses of BP1001 (for Days 1 and 4) in order to proceed to Das dosing and continue in the study. Participants not receiving both doses of BP1001 prior to initiating Das dosing may be discontinued from the dosing portion of the study and enter the follow-up portion of the study.

Dose amounts for BP1001 will be based on baseline (at screening) body surface area (BSA); however, doses will be adjusted for participants who experience a ≥10% change in weight from baseline. Actual weight will be used to calculate BSA except for participants weighing greater than 100 kg; dose will be calculated based on 100 kg for these individuals.

The IV infusion will be administered over approximately 1-3 hours and should not be given as an IV push or IV bolus. The infusion will be given through a dedicated central or peripheral IV line and cannot be given at the same time as other medications.

Study Treatments: Dasatinib Dose and Administration.

Dasatinib (Das) is to be administered orally, once daily beginning on approximately day 5 of each 28-day cycle. Dosing of Das may begin as early as Day 5 of each cycle as long as it is initiated no less than 24 hours after completion of the second dose of BP1001. Once initiated, Das treatment is to continue without interruption. The dose of Das used in this study is 140 mg (each dose).

Concomitant Medications.

During the first 4 weeks of therapy, hydroxyurea will be allowed. Anagrelide will also be allowed at any time to manage thrombocytosis >500K. The following medications are not permitted during the treatment period: any anti-cancer agents (other than Das, hydroxyurea, or anagrelide) for treatment of the disease under study or other malignancies.

Schedule and Description of Procedures.

Participants will undergo screening procedures as shown in Table 10.

TABLE 10

Schedule of Events and Assessments

| | | | | | Treatment Period Day of Cycle | | | | | |
|---|---|---|---|---|---|---|---|---|---|---|
| | −14 to −1 | 1 | 4 | 8 | 11 | 15 | 18 | 22 | 25 | 28/EOT |
| | | | | | Tolerance (in days) | | | | | |
| EVENT/ASSESSMENT | 0 | 0 | +1 | +1 | +1 | +1 | +1 | +1 | +1 | ±1 |
| Informed consent | X | | | | | | | | | |
| Demography | X | | | | | | | | | |
| Medical history | X | $X^a$ | | | | | | | | |
| Physical examination (PE) | $X^b$ | | | | | $X^{c,d}$ | | | | $X^c$ |
| ECOG performance status | X | | | | | | | | | |
| Height, weight, and BSA | X | | | | | | | | | $X^e$ |
| Vital signs | X | X | X | X | X | X | X | X | X | X |
| ECG (at least 12-leads) | X | | | | | | | | | X |
| Chest X-ray | X | | | | | | | | | |
| Serology for HBV, HCV, HIV | X | | | | | | | | | |
| CBC (with diff., incl. blast %) | X | $X^f$ | | $X^d$ | | X | | $X^d$ | | $X^g$ |
| Coagulation Profile | X | | | | | | | | | $X^d$ |
| Serum chemistry | X | $X^f$ | | $X^d$ | | X | | $X^d$ | | X |
| Urinalysis | X | | | | | $X^d$ | | | | X |
| Bone Marrow Assessment | X | | | | | | | | | $X^h$ |
| Pregancy test (serum)$^{f,i}$ | X | | | | | | | | | |
| Pregnancy test (urine)$^{f,i}$ | | X | | | | | | | | |
| Confirm eligibility criteria | X | $X^{d,f}$ | | | | | | | | |
| BP1001 administration$^j$ | | X | X | X | X | X | X | X | X | |
| Das administration$^k$ | | | | | X-------------------------------------------- | | | | | |
| BP1001 plasma PK$^l$ | | $X^{d,f}$ | | | $X^{d,f}$ | | | | | |
| Record concomitant medications | X-------------------------------------------------------------------------------------- | | | | | X | | | | |
| Record adverse events | X-------------------------------------------------------------------------------------- | | | | | | | | | X |

$^a$Updated, based on history given at SCR
$^b$Physical exam should include a complete review of symptoms and full exam
$^c$Symptom oriented brief PE only
$^d$Cycle 1 only; Samples will be collected predose (within 30 minutes prior to dosing) and then at 1, 2, 4, 6, 8, and 24 hours postdose. Postdose samples may be taken +/−15 minutes of their specified time.
$^e$Weight only
$^f$Blood samples must be taken prior to any study drug or Das dosing
$^g$Hematological response assessed at the end of each cycle
$^h$Bone marrow assessment, including cytogenetic and molecular responses, will be performed at end of cycles 1, 2, 4, 6 and even cycles thereafter
$^i$Women of child-bearing potential only
$^j$BP1001 administered as an intravenous (IV) infusion twice weekly (every 2-4 days), with a ±1 day window
$^k$Das administered without interruption; orally 1 daily, no less than 24 hours after completion of the second dose of BP1001
$^l$Multiple PK assessments. Samples should be collected at the following time points: predose, 1, 2, 4, 6, 8 and 24 hours post-dose. Post-dose samples may be ±15 min The initial follow-up visit should occur within 30 days (+/−7 days) after discontinuing treatment cycles. The initial follow-up visit will include: Physical examination; CBC with differential and platelets, including blasts %; Serum chemistry; Record concomitant medications; Record adverse events.

Long-term follow up visits should occur every 8 weeks (+/−1 week) from the 30-day follow up visit, until 12 months from start of therapy or until study closure or start of another therapy or death.

Efficacy Endpoints.

Preliminary efficacy will be assessed by evaluating remission and objective response, using the following Response Criteria and measures. Additional efficacy endpoints will include time to response, duration of response, and overall survival.

The hematologic response (HR) criteria are provided in Table 11. A confirmed HR is obtained when all of the criteria are fulfilled at least 28 days after they are first met.

TABLE 11

Hematologic response criteria

| Response | Criteria |
|---|---|
| Major Response | Peripheral blood WBC ≤ institutional upper limit of normal (ULN)<br>Platelets <450,000 × 10⁹/L<br>No blasts or promyelocytes in peripheral blood<br><5% myelocytes plus metamyelocytes in peripheral blood<br>Peripheral blood basophils <20%<br>No extra-medullary involvement including no splenomegaly or hepatomegaly<br><5% blasts in bone marrow |
| Partial Response | Peripheral blood WBC ≤ institutional ULN<br>Platelets >450,000 × 10⁹/L, but <50% pre-therapeutic level<br>No blasts or promyelocytes in peripheral blood<br>>5% myelocytes and metamyelocytes in peripheral blood<br>Peripheral blood basophils <20%<br>Splenomegaly or hepatomegaly if present, must be <50% pre-therapeutic level |
| Progressive Disease | Advancement of accelerated phase patient to blast phase<br>For blast phase patients, doubling of peripheral white blood count at least twice over 28 days to >20,000/μL<br>For any patient, death due to disease |
| Stable Disease | Patient does not meet the criteria for hematologic response or progressive disease |

A cytogenetic response is classified according to suppression of the Philadelphia chromosome (Ph) by cytogenetics (or FISH if cytogenetic analysis is not informative, e.g., insufficient metaphases) as provided in Table 12. A major cytogenetic response is a combination of a complete and a partial response.

TABLE 12

Cytogenetic response criteria

| Response | Criteria |
|---|---|
| No cytogenetic response | Ph positive >95% |
| Minor cytogenetic response | Ph positive 36-65% |
| Partial cytogenetic response | Ph positive 1-35% |
| Complete cytogenetic response | Ph positive 0% |

A molecular response is classified according to the criteria provided in Table 13.

TABLE 13

Molecular response criteria

| Response | Criteria |
|---|---|
| Major | BCR-ABL/ABL ratio ≤0.1% (International Scale—IS-) |
| MR4 | BCR-ABL/ABL <0.01% IS |
| MR4.5 | BCR-ABL/ABL <0.0032% IS |

Safety Reporting: Adverse Events (AEs).

Each participant who receives study drug will be closely monitored for AEs. An AE is any untoward medical occurrence associated with the use of a drug in humans, whether or not considered drug related. Adverse events include any signs, symptoms, illnesses, or diagnoses that appear or worsen during the course of the study. An AE may be an intercurrent illness, an injury, or any concomitant impairment of the participant's health. All AEs occurring at any time from the time of consent through the end of treatment visit will be reported regardless of the etiology of the event. The NCI's CTCAE v4.03 will be used for grading AEs. The CTCAE can be found on the world wide web at evs.nci.nih.gov/ftp1/CTCAE/CTCAE_4.03_2010-06-14_QuickReference_5×7.pdf Adverse events are classified as "serious" and "non-serious" for regulatory reporting purposes. Note that the definition of "serious" does not necessarily depend on the severity of the event. All AEs that do not meet the criteria of serious are considered non-serious.

Any AE occurring at any dose (including overdose), regardless of relationship to study drug, will be classified as a serious adverse event (SAE) when (1) it results in death (i.e., the AE caused or led to the fatality, the participant was at risk of death at the time of the event; it does not refer to an event, which hypothetically might have caused death if it were more severe); (2) it was life-threatening (i.e., the AE placed the individual at immediate risk of dying, not if the AE may have hypothetically led to death if it were more severe); (3) it required hospitalization or prolonged hospitalization beyond the expected length of stay (i.e., hospitalizations for scheduled treatments and elective medical/surgical procedures are not SAEs by this criterion); (4) it was disabling (i.e., the AE resulted in substantial reduction of the participant's ability to carry out activities of daily living); (5) it resulted in a congenital anomaly or birth defect (i.e., an adverse finding in a child or fetus of a participant exposed to the study drug prior to conception or during pregnancy); or (6) it was a medically important condition (i.e., the AE does not meet any of the above serious criteria but based on appropriate medical judgment, may have jeopardized the participant or required medical or surgical intervention to prevent 1 of the serious outcomes listed in these criteria [i.e., intensive treatment in an emergency room or at home for allergic bronchospasm; blood dyscrasias, or convulsions that do not result in hospitalization]).

The causal relationship to BP1001 IP or Das for all AEs will be assessed as follows: (1) definitely related—AEs clearly attributable to study regimen administration; (2) probably related—AEs for which there is a reasonable possibility of causal association to study regimen; (3) possibly related—AEs for which there is confounding by comorbidities, medications or other considerations but for which it is not unreasonable that the AE may have been caused by study regimen; or (4) not related—AEs that are considered clearly not causally related to study regimen, or for which there is a clear alternative explanation An unexpected AE is any AE that is not identified in nature, severity, or frequency as a known consequence of either BP1001 or Das. "Unexpected" as used in this definition refers to an AE that has not been previously observed rather than from the perspective of such experience not being anticipated from the pharmacological properties of the pharmaceutical product.

Table 14 details the most frequently occurring AEs for monotherapy with BP1001 as well as AEs with intensity of Grade 3 or higher (based on the National Cancer Institute [NCI] Common Terminology Criteria for Adverse Events [CTCAE], Version 4.0) in study 2003-0578, presented by treatment group, disease diagnosis at study enrollment, and system organ class (SOC)/preferred term (PT) as specified in the Medical Dictionary for Regulatory Activities (MedDRA, Version 18.0).

TABLE 14

Most Frequent Adverse Events (≥Grade 3) by Treatment Group, Disease, SOC, and PT
Number of Patients (N = 39)

| System Organ Class (Events/Patients) Preferred Term | Mono Therapy-BP1001 mg/m$^2$ | | | | | | Combination Therapy-BP1001 mg/m$^2$ + LDAC | | Diagnosis at Enrollment | | |
|---|---|---|---|---|---|---|---|---|---|---|---|
| | 5 (n = 13) | 10 (n = 6) | 20 (n = 3) | 40 (n = 3) | 60 (n = 3) | 90 (n = 4) | 60 (n = 4) | 90 (n = 3) | AML (n = 30) | CML (n = 5) | MDS (n = 4) |
| Patients with AEs (91/28) | 10 | 4 | 1 | 3 | 1 | 4 | 3 | 2 | 23 | 4 | 1 |
| Metabolism and nutritional disorders (19/12) | 12 | 3 | 0 | 1 | 0 | 3 | 0 | 0 | 8 | 4 | 0 |
| Hypokalemia | 1 | 1 | 0 | 1 | 0 | 1 | 0 | 0 | 3 | 1 | 0 |
| Tumor lysis syndrome | 3 | 0 | 0 | 0 | 0 | 0 | 0 | 0 | 1 | 2 | 0 |
| Acidosis | 2 | 1 | 0 | 0 | 0 | 0 | 0 | 0 | 3 | 0 | 0 |
| Hypocalcemia | 1 | 0 | 0 | 0 | 0 | 1 | 0 | 0 | 1 | 1 | 0 |
| Respiratory failure | 2 | 1 | 0 | 0 | 0 | 0 | 0 | 0 | 3 | 0 | 0 |
| Hypoglycemia | 2 | 0 | 0 | 0 | 0 | 0 | 0 | 0 | 1 | 1 | 0 |
| Hyponatremia | 1 | 0 | 0 | 0 | 0 | 1 | 0 | 0 | 1 | 1 | 0 |
| Blood and lymphatic system disorders (12/11) | 5 | 2 | 1 | 1 | 0 | 1 | 2 | 0 | 10 | 2 | 0 |
| Leukocytosis | 3 | 2 | 1 | 1 | 0 | 1 | 0 | 0 | 6 | 2 | 0 |
| Hypovolemia | 0 | 0 | 0 | 0 | 0 | 0 | 1 | 0 | 1 | 0 | 0 |
| Febrile neutropenia | 2 | 1[a] | 0 | 0 | 0 | 0 | 1 | 0 | 3 | 0 | 0 |
| Infections and infestations (9/9) | 4 | 3 | 0 | 0 | 0 | 2 | 1 | 0 | 10 | 1 | 0 |
| Pneumonia | 0 | 2 | 0 | 0 | 0 | 2 | 0 | 0 | 4 | 0 | 0 |
| Sepsis | 4 | 1 | 0 | 0 | 0 | 0 | | | 4 | 1 | 0 |
| Bilateral Lung Infection | 0 | 0 | 0 | 0 | 0 | 0 | 1 | 0 | 1 | 0 | 0 |
| Infection | 0 | 0 | 0 | 0 | 0 | 0 | 1 | 0 | 1 | 0 | 0 |
| Respiratory, thoracic, and mediastinal disorders (7/7) | 2 | 3 | 0 | 1 | 0 | 1 | 3 | 1 | 10 | 1 | 0 |
| Dyspnea | 0 | 0 | 0 | 1 | 0 | 1 | 0 | 1 | 3 | 0 | 0 |
| Hypoxia | 1 | 1 | 0 | 0 | 0 | 0 | 2 | 0 | 4 | 0 | 0 |
| Pleural Effusions | | | | | | | 1 | 0 | 1 | 0 | 0 |
| Respiratory distress | 1 | 2 | 0 | 0 | 0 | 0 | 0 | 0 | 2 | 1 | 0 |
| General disorders and administration site conditions (5/5) | 3 | 1 | 0 | 0 | 0 | 1 | 1 | 0 | 4 | 2 | 0 |
| Asthenia | 1 | 0 | 0 | 0 | 0 | 1 | 0 | 0 | 1 | 1 | 0 |
| Multi-organ failure | 2 | 1 | 0 | 0 | 0 | 0 | 0 | 0 | 2 | 1 | 0 |
| Extremity Lower Edema | 0 | 0 | 0 | 0 | 0 | 0 | 1 | 0 | 1 | 0 | 0 |
| Renal and urinary disorders (4/4) | 3 | 0 | 0 | 1 | 0 | 0 | 0 | 0 | 3 | 1 | 0 |
| Acute kidney injury | 3 | 0 | 0 | 1 | 0 | 0 | 0 | 0 | 3 | 1 | 0 |
| Cardiac disorders (3/3) | 3 | 0 | 0 | 0 | 0 | 0 | 0 | 0 | 1 | 1 | 1 |
| Heart failure | 3 | 0 | 0 | 0 | 0 | 0 | 0 | 0 | 1 | 1 | 1 |
| Investigations (3/2) | 1 | 0 | 0 | 0 | 0 | 1 | 0 | 0 | 2 | 0 | 0 |

TABLE 14-continued

Most Frequent Adverse Events (≥Grade 3) by Treatment Group, Disease, SOC, and PT
Number of Patients (N = 39)

| System Organ Class (Events/Patients) Preferred Term | Mono Therapy-BP1001 mg/m² | | | | | | Combination Therapy-BP1001 mg/m² + LDAC | | Diagnosis at Enrollment | | |
|---|---|---|---|---|---|---|---|---|---|---|---|
| | 5 (n = 13) | 10 (n = 6) | 20 (n = 3) | 40 (n = 3) | 60 (n = 3) | 90 (n = 4) | 60 (n = 4) | 90 (n = 3) | AML (n = 30) | CML (n = 5) | MDS (n = 4) |
| Platelet count decreased | 1 | 0 | 0 | 0 | 0 | 1ᵃ | 0 | 0 | 2 | 0 | 0 |
| Vascular disorders (2/2) | 2 | 0 | 0 | 0 | 0 | 0 | 1 | 0 | 3 | 0 | 0 |
| Hypotension | 2 | 0 | 0 | 0 | 0 | 0 | 1 | 0 | 3 | 0 | 0 |
| Hepatobiliary disorders (2/2) | 1 | 1 | 0 | 0 | 0 | 0 | 0 | 0 | 2 | 0 | 0 |
| Hepatic failure | 1 | 1 | 0 | 0 | 0 | 0 | 0 | 0 | 2 | 0 | 0 |
| Neoplasms benign, malignant, and unspecified (incl. cysts and polyps) (2/2) | 0 | 1 | 0 | 0 | 1 | 0 | 0 | 0 | 2 | 0 | 0 |
| Gastrointestinal disorders | 0 | 0 | 0 | 0 | 0 | 0 | 1 | 0 | 1 | 0 | 0 |
| Abdominal Pain | 0 | 0 | 0 | 0 | 0 | 0 | 1 | 0 | 1 | 0 | 0 |
| Psychiatric disorders | 0 | 0 | 0 | 0 | 0 | 0 | 0 | 1 | 1 | 0 | 0 |
| Hallucinations | 0 | 0 | 0 | 0 | 0 | 0 | 0 | 1 | 1 | 0 | 0 |
| Musculoskeletal and connective tissue disorders | 0 | | 0 | 0 | 0 | 0 | 0 | 1 | 1 | 0 | 0 |
| Back Pain | 0 | 0 | 0 | 0 | 0 | 0 | 0 | 1 | 1 | 0 | 0 |
| Reproductive system and breast disorders | 0 | 0 | 0 | 0 | 0 | 0 | 1 | 0 | 1 | 0 | 0 |
| Penile Pain | 0 | 0 | 0 | 0 | 0 | 0 | 1 | 0 | 1 | 0 | 0 |
| Eye disorders | 0 | 0 | 0 | 0 | 0 | 0 | 1 | 0 | 1 | 0 | 0 |
| Cataract | 0 | 0 | 0 | 0 | 0 | 0 | 1 | 0 | 1 | 0 | 0 |
| AML progression | 10 | 4 | 1 | 3 | 3 | 2 | 1 | 1 | 19 | 5 | 2 |

Table 15 details comprehensive listing for the incidence of all treatment for monotherapy with BP1001 adverse events in study 2003-0578 presented by SOC/PT, incidence, and intensity (based on NCI CTCAE).

TABLE 15

Adverse Events Assessed as Related to Study Drug BP1001

| System Organ Class (Events/Patients) Preferred Term | Patient Study ID | Dose - Monotherapy BP1001 mg/m² | Dose - Combination Therapy BP1001 mg/m² + LDAC | Grade | Dose-limiting Toxicity (DLT) |
|---|---|---|---|---|---|
| Blood and lymphatic system disorders (1/1) | | | | | |
| Coagulopathy | 1 | 5 | NA | 1 | No |
| Gastrointestinal disorders (4/1) | | | | | |
| Diarrhea | 1 | 5 | NA | 1 | No |
| Mucositis | 1 | | | 2 | No |
| Mucositis | 1 | | | 4 | Yes ᵃ |
| Nausea | 1 | | | 2 | No |
| General disorders and administration site conditions (4/1) | | | | | |
| Edema (limbs) | 1 | 5 | NA | 2 | No |
| Fever (pyrexia) | 1 | | | 1 | No |
| Multi-organ failure | 1 | | | 5 | No |
| Pain | 1 | | | 2 | No |

TABLE 15-continued

Adverse Events Assessed as Related to Study Drug BP1001

| System Organ Class (Events/Patients) Preferred Term | Patient Study ID | Dose - Monotherapy BP1001 mg/m$^2$ | Dose - Combination Therapy BP1001 mg/m$^2$ + LDAC | Grade | Dose-limiting Toxicity (DLT) |
|---|---|---|---|---|---|
| Infections and infestations (1/1) | | | | | |
| Blood creatinine increased | 10 | 5 | NA | 2 | No |
| Metabolism and nutritional disorders (6/1) | | | | | |
| Hyperkalemia | 1 | 5 | NA | 2 | No |
| Hypocalcemia | 1 | | | 2$^b$ | No |
| Hypocalcemia | 1 | | | 3$^b$ | No |
| Hypokalemia | 1 | 5 | NA | 3 | No |
| Musculoskeletal and connective tissue disorders (1/1) | | | | | |
| Pain in extremity | 1 | 5 | NA | 2 | No |
| Psychiatric disorders (1/1) | | | | | |
| Confusion | 1 | 5 | NA | 1 | No |
| Palmar-plantar erythrodysesthesia (hand and foot) syndrome | 1 | 5 | NA | 3 | Yes $^a$ |
| Pruritus | 1 | | | 1 | No |

$^a$ Since these events were assessed as Possibly Related to study Drug BP1001 and were grade 3, they were assessed as DLTs. Both events occurred in patient 001, at the 5 mg/m$^2$ dose level (Cohort 1). Per protocol, the cohort was expanded to 6 evaluable patients. At this time, all 6 patients have been reviewed, with no recurrences of either of these events in any treated patient.
$^b$Two (2) incidences of this event were reported for this patient, at the same grade level.

Possible Risks and Side Effects.

Dasatinib (Das) and BP1001 each may cause low blood cell counts (red blood cells, platelets, and white blood cells). Known Das side effects include fever, skin rash, headache, tiredness, diarrhea, nausea, shortness of breath, and muscle pain. Based on studies in animals and human, BP1001 may cause hand-foot syndrome, mouth blisters/sores, and low white blood cell counts.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ashizawa A T and Cortes J. Liposomal delivery of nucleic acid-based anticancer therapeutics: BP-100-1.01. *Expert Opinion* in Drug Delivery, 12:1107-1120, 2015.

ACS Website. (2013 Jul. 24). What are the key statistics about acute myeloid leukemia?, Updated Feb. 7, 2014. Retrieved Jan. 6, 2015, from American Cancer Society: http://www.cancer.org/cancer/leukemia-acutemyeloidaml/detailedguide/leukemia-acute-myeloid-myelogenous-key-statistics Appelbaum F R, Gundacker H, Head D R, Slovak M L, Willman C L, Godwin J E, Anderson J E, Petersdorf S H. Age and acute myeloid leukemia. Blood, 2006; 107(9), 3481-3485.

Burnett A K, Milligan D, Prentice A G, Goldstone A H, McMullin M F, Hills F K, Wheatley K. A comparison of low-dose cytarabine and hydroxyurea with or without all-trans retinoic acid for acute myeloid leukemia and high-risk myelodysplastic syndrome in patients not considered fit for intensive treatment. Cancer, 2007; 109, 1114-1124.

Cheson B D, Jasperse D M, Simon R, Friedman M A. A critical appraisal of low-dose cytosine arabinoside in patients with acute non-lymphocytic leukemia and myelodysplastic syndromes. J Clin Oncol, 1986; 4(12), 1857-1864.

Cortes J E, Kantarjian H, Shah N P, Bixby D, Mauro M J, Flinn I, O'Hare T, Hu S, Narasimhan N I, Rivera V M, Clackson T, Turner C D, Haluska F G, Druker B J, Deininger M W N, Talpaz M. (2012) Ponatinib in refractory Philadelphia chromosome-positive leukemias. N Engl J Med 367: 2075-2088.

Daley G, van Etten R, Baltimore D. (1990) Induction of chronic myelogenous leukemia in mice by the P210bcr/abl gene of the Philadelphia chromosome. Science 247: 824-830.

Degos L, Castaigne S, Tilly H, Sigaux F, Daniel M T. Treatment of leukemia with low-dose ara-C: a study of 160 cases. Semin Oncol, 1985; 12(2 Suppl 3), 196-199.

de Klein A, van Kessel A G, Grosveld G, Bartram C R, Hagemeijer A, Bootsma D, Spurr N K, Heisterkamp N, Groffen J, Stephenson J R. (1982) A cellular oncogene is translocated to the Philadelphia chromosome in chronic myelocytic leukaemia. Nature 300: 765-767.

Druker B J. STI571 (Gleevec) as a paradigm for cancer therapy. (2002) Trends Mol Med 8: S14-18.

Druker B J. (2008) Translation of the Philadelphia chromosome into therapy for CML. Blood 112: 4808-4817.

Epner D, Koeffler H. (1990) Molecular genetic advances in chronic myelogenous leukemia. Ann Int Med 1: 3-6.

Fath I, Schweighoffer F, Rey I, Mutton M C, Boiziau J, Duchesne M, Tocque B. Cloning of a Grb2 isoform with apoptotic properties. (1994) Science 264: 971-974.

Fukushima T, Kawabata H, Sawaki T, Satoh T, Nakamura T, Iwao H, Nakajima A, Sakai T, Miki M, Fujita Y, Tanaka M, Kawanami T, Masaki Y, Okazaki T, Umehara H. Low-dose cytarabine plus aclarubicin for patients with previously untreated acute myeloid leukemia or high-risk myelodysplastic syndrome ineligible for standard-dose cytarabine plus anthracycline. Anticancer Res, 2012; 32, 1347-1354.

Gay B, Suarez S, Caravatti G, Furet P, Meyer T, Schoepfer J. Selective Grb2 SH2 inhibitors as anti-Ras therapy. Int J Cancer 83, 1999; 235-241.

Groffen J, Stephenson J R, Heisterkamp N, de Klein A, Bartram C R, Grosveld G. (1984) Philadelphia chromosomal breakpoints are clustered within a limited region, bcr, on chromosome 22. Cell 36: 93-99.

Gutierrez-Puente Y, Tari A M, Stephens C, Rosenblum M, Guerra R T, Lopez-Berestein G. Safety, pharmacokinetics, and tissue distribution of liposomal P-ethoxy antisense oligonucleotides targeted to Bcl-2. (1999) J Pharmacol Exp Ther 291: 865-869.

Heisterkamp N, Stephenson J R, Groffen J, Hansen P F, de Klein A, Bartram C R, Grosveld G. (1983) Localization of the c-abl oncogene adjacent to a translocation breakpoint in chronic myelocytic leukaemia. Nature 306: 239-242.

Heisterkamp N, Henster G, ten Hoeve J, Zovich D, Pattengale P, Groffen J. (1990) Acute leukaemia in bcr/abl transgenic mice. Nature 344: 251-253.

Kadia T M, Borthakur G, Ferrajoli A, et al. Phase II trial of cladribine and low-dose arac (LDAC) alternating with decitabine in older patients with acute myeloid leukemia (AML). Blood, 2013; 15, 5011.

Kloetzer W, Kurzrock R, Smith L, Talpaz M, Spiller M, Gutterman J, and Arlinghaus R. (1985) The human cellular abl gene product in the chronic myelogenous leukemia cell line K562 has an associated tyrosine protein kinase activity. Virology 140: 230-238.

Konopka J, Watanabe S, Witte O. (1984) An alteration of the human c-abl protein in K562 leukemia cells unmasks associated tyrosine kinase activity. Cell 37: 1035-1042.

Lim S-J, Lopez-Berestein G, Hung M-C, Lupu R, Tari A M. Grb2 downregulation leads to Akt inactivation in heregulin-stimulated and ErbB2-overexpressing breast cancer cells. Oncogene, 2000; 19, 6271-6276.

Menzin J, Lang K, Earle C C, Kerney D, Mallick R. The outcomes and costs of acute myeloid leukemia among the elderly. Arch Intern Med, 2002; 162(14), 1597-1603.

Moloney W C, Rosenthal D S. Treatment of early acute nonlymphatic leukemia with low dose cytosine arabinoside. Haematol Blood Transfus, 1981; 26, 59-62.

Mufti G J, Oscier D G, Hamblin T J, Bell A J. Low doses of cytarabine in the treatment of myelodysplastic syndrome and acute myeloid leukemia. N Engl J Med, 1983; 309 (26), 1653-1654.

Nowell P, Hungerford D. (1960) A minute chromosome in human chronic granulocytic leukemia. Science132: 1497.

Nowell P, Hungerford D A. (1960) Chromosome studies on normal and leukemic human leukocytes. J. Natl. Cancer Inst. 25: 85-109.

Pendergast A, Quilliam L, Cripe L, Bassing C, Dai Z, Li N, Batzer A, Rabun K, Der C, Schlessinger J, Gishizky M. (1993) BCR-ABL-induced oncogenesis is mediated by direct interaction with the SH2 domain of the GRB-2 adaptor protein. Cell 75: 175-185.

Puil L, Liu J, GishG, Mbamalu G, Bowtell D, Pelicci P, Arlinghaus R, Pawson T. (1994) Bcr-Abl oncoproteins bind directly to activators of the Ras signalling pathway. EMBO J 13: 764-773.

Rowley J D. (1973) Letter: A new consistent chromosomal abnormality in chronic myelogenous leukaemia identified by quinacrine fluorescence and Giemsa staining. Nature 243: 290-293.

Shtivelman E, Lifshitz B, Gale R P, Canaani E. (1985) Fused transcript of abl and bcr genes in chronic myelogenous leukaemia. Nature 315: 550-554.

Skorski T, Kanakaraj P, Ku D H, Nieborowska-Skorska M, Canaani E, Zon G, Perussia B, Calabretta B. (1994) Negative regulation of p120GAP GTPase promoting activity by p210bcr/abl: implication for Ras-dependent Philadelphia chromosome positive cell growth. J Exp Med 179: 1855-1865.

Skorski T, Kanakaraj P, Ku D-H, Nieborowska-Skorska M, Ratajczak M, Wen S-C, Zon G, Gewirtz A, Perussia B, Calabretta B. (1995) Phosphatidylinositol-3 kinase activity is regulated by BCR/ABL and is required for the growth of Philadelphia chromosome-positive cells. Blood 86: 726-736.

Stam K, Heisterkamp N, Grosveld G, de Klein A, Verma R S, Coleman M, Dosik H, Groffen J. (1985) Evidence of a new chimeric bcr/c-abl mRNA in patients with chronic myelocytic leukemia and the Philadelphia chromosome. N Engl J Med 313: 1429-1433.

Tani Ashizawa A, Cortes J. (2015) Liposomal delivery of nucleic acid-based anticancer therapeutics: BP-100-1.01. Expert Opin Drug Deliv 12: 1107-1120.

Tani A M, Gutiérrez-Puente Y, Stephens C, et. al. Liposome-incorporated Grb2 antisense oligodeoxynucleotide increases the survival of mice bearing bcr-abl-positive leukemia xenografts. (2007) Int J Oncol 31: 1243-1250.

Tani A M, Lopez-Berestein G. Cellular uptake of antisense oligonucleotides. Curr Opin Invest Drugs, 2001; 2, 1450-1453.

Tani A M, Lopez-Berestein G. (2001) GRB2: a pivotal protein in signal transduction. Semin Oncol 28: 142-147.

Tani A M, Stephens C, Rosenblum M, Lopez-Berestein G. Pharmacokinetics, tissue distribution, and safety of P-ethoxy oligonucleotides incorporated in liposomes. J Liposome Res, 1998; 8, 251-264.

Tani A M, Hung M-C, Li K, Lopez-Berestein G. Growth inhibition of breast cancer cells by Grb2 downregulation is correlated with inactivation of mitogen-activated protein kinase in EGFR, but not in ErbB2, cells. Oncogene, 1999; 18, 1325-1332.

Tani A M, Arlinghaus R, Lopez-Berestein G. Inhibition of Grb2 and Crk1 proteins results in growth inhibiton of Philadelphia chromosome positive leukemia cells. Biochem Biophys Res Commun, 1997; 235, 383-388.

Thall P F, Simon R M, Estey E H. (1995) Bayesian sequential monitoring designs for single-arm clinical trials with multiple outcomes. Statistics in medicine 14: 357-379.

Tilly H, Castaigne S, Bordessoule D, Casassus P, Le Prise P Y, Tertian G, Desablens B, Henry-Amar M, Degos L. Low-dose cytarabine versus intensive chemotherapy in the treatment of acute nonlymphocytic leukemia in the elderly. J Clin Oncol, 1990; 8(2), 272-279.

Vardiman J W, Thiele J, Arber D A, et. al. The 2008 revision of the World Health Organization (WHO) classification of myeloid neoplasms and acute leukemia: rationale and important changes. (2009) Blood 114: 937-951.

Williams E, Dunican D, Green P et al, Selective inhibition of growth factor-stimulated mitogenesis by a cell-permeable Grb2-binding peptide. J Biol Chem, 1997; 272, 22349-22354.

What is claimed is:

1. A method of treating a cancer in a patient in need thereof comprising administering to the patient an effective amount of a first pharmaceutical therapy comprising a nuclease-resistant polynucleotide that hybridizes to a Grb2 nucleic acid in the patient and a second pharmaceutical therapy comprising a Bcr-Abl tyrosine kinase inhibitor; wherein the Bcr-Abl tyrosine kinase inhibitor is dasatinib or nilotinib, wherein the first pharmaceutical therapy is administered prior to the administration of the second pharmaceutical therapy.

2. The method of claim 1, wherein the polynucleotide hybridizes to the translation initiation site of a Grb2 nucleic acid.

3. The method of claim 1, wherein the polynucleotide is an oligonucleotide having a length of 8-50 bases.

4. The method of claim 1, wherein the polynucleotide has a sequence according to SEQ ID NO: 1.

5. The method of claim 1, wherein the polynucleotide comprises P-ethoxy backbone linkages.

6. The method of claim 1, wherein the polynucleotide is encapsulated in a liposome.

7. The method of claim 1, wherein the first pharmaceutical therapy further comprises a neutral lipid.

8. The method of claim 1, wherein the first pharmaceutical therapy is administered systemically.

9. The method of claim 1, wherein the first pharmaceutical therapy is formulated for intraarterial or intravenous administration.

10. The method of claim 7, wherein the first pharmaceutical therapy is administered at a dosage of from about 60 mg/m$^2$ and to about 90 mg/m$^2$.

11. The method of claim 7, wherein the first pharmaceutical therapy is administered two to four times per week.

12. The method of claim 1, wherein the Bcr-Abl tyrosine kinase inhibitor is dasatinib.

13. The method of claim 12, wherein the dasatinib is administered at a dosage of about 140 mg.

14. The method of claim 12, wherein the dasatinib is administered once daily.

15. The method of claim 1, wherein the second pharmaceutical therapy is administered systemically.

16. The method of claim 15, wherein the second pharmaceutical therapy is administered orally, intraarterially, or intravenously.

17. The method of claim 1, wherein the first pharmaceutical therapy is administered at least one day prior to the administration of the second pharmaceutical therapy.

18. The method of claim 1, wherein the first pharmaceutical therapy and the second pharmaceutical therapy are administered by distinct routes.

19. The method of claim 1, wherein the patient is a human.

20. The method of claim 1, wherein the cancer is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma.

21. The method of claim 1, wherein the cancer is a blood cancer.

22. The method of claim 21, wherein the blood cancer is a chronic myelogenous leukemia (CIVIL), an acute myeloid leukemia (AML), or a myelodysplastic syndrome (MDS).

23. The method of claim 22, wherein the CML is an accelerated CML or a blast-phase CML.

24. The method of claim 22, wherein the CML or AML is Bcr-Abl positive CML or Bcr-Abl positive AML.

25. The method of claim 24, wherein the Bcr-Abl positive CIVIL or Bcr-Abl positive AML is positive for a T315I Bcr-Abl mutation.

26. The method of claim 22, wherein the CIVIL or AML is a Philadelphia chromosome-positive CML or Philadelphia chromosome-positive AML.

27. The method of claim 1, wherein the patient has previously failed treatment with imatinib.

28. A method of treating a cancer or myelodysplastic syndrome (MDS) in a patient in need thereof comprising administering to the patient an effective amount of a first pharmaceutical therapy comprising a nuclease-resistant polynucleotide that hybridizes to a Grb2 nucleic acid and a second pharmaceutical therapy comprising a cytidine analogue.

29. The method of claim 28, wherein the polynucleotide hybridizes to the translation initiation site of a Grb2 nucleic acid.

30. The method of claim 28, wherein the polynucleotide is an oligonucleotide having a length of 8-50 bases.

31. The method of claim 28, wherein the polynucleotide has a sequence according to SEQ ID NO: 1.

32. The method of claim 28, wherein the polynucleotide comprises P-ethoxy backbone linkages.

33. The method of claim 28, wherein the polynucleotide is encapsulated in a liposome.

34. The method of claim 28, wherein the first pharmaceutical therapy further comprises a neutral lipid.

35. The method of claim 28, wherein the first pharmaceutical therapy is administered systemically.

36. The method of claim 28, wherein the first pharmaceutical therapy is formulated for intraarterial or intravenous administration.

37. The method of claim 34, wherein the first pharmaceutical therapy is administered at a dosage of from about 60 mg/m$^2$ and to about 90 mg/m$^2$.

38. The method of claim 34, wherein the first pharmaceutical therapy is administered two to four times per week.

39. The method of claim 28, wherein the cytidine analogue is decitabine, cytarabine, or azacitidine.

40. The method of claim 39, wherein the cytidine analogue is decitabine.

41. The method of claim 39, wherein the cytidine analogue is cytarabine.

42. The method of claim 41, wherein the cytarabine is administered at a dosage of about 20 mg.

43. The method of claim 41, wherein the cytarabine is administered twice daily.

44. The method of claim 41, wherein the cytarabine is administered subcutaneously.

45. The method of claim 28, wherein the first pharmaceutical therapy is administered prior to the administration of the second pharmaceutical therapy.

46. The method of claim 28, wherein the first pharmaceutical therapy and the second pharmaceutical therapy are administered concurrently.

47. The method of claim 28, wherein the second pharmaceutical therapy is administered prior to the administration of the first pharmaceutical therapy.

48. The method of claim 28, wherein the first pharmaceutical therapy and the second pharmaceutical therapy are administered by distinct routes.

49. The method of claim 28, wherein the patient is a human.

50. The method of claim 28, wherein the cancer is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma.

51. The method of claim 50, wherein the cancer is a blood cancer.

52. The method of claim 51, wherein the blood cancer is a chronic myelogenous leukemia (CIVIL), an acute myeloid leukemia (AML), or a myelodysplastic syndrome (MDS).

53. The method of claim 52, wherein the CML is an accelerated CML or a blast-phase CML.

54. The method of claim 52, wherein the CML or AML is a Bcr-Abl positive CML or Bcr-Abl positive AML.

55. The method of claim 54, wherein the Bcr-Abl positive CIVIL or Bcr-Abl positive AML is positive for a T315I Bcr-Abl mutation.

56. The method of claim 52, wherein the CIVIL or AML is a Philadelphia chromosome-positive CML or Philadelphia chromosome-positive AML.

\* \* \* \* \*

UNITED STATES PATENT AND TRADEMARK OFFICE
CERTIFICATE OF CORRECTION

PATENT NO. : 10,927,379 B2
APPLICATION NO. : 16/333221
DATED : February 23, 2021
INVENTOR(S) : Ana Tari Ashizawa Page 1 of 1

It is certified that error appears in the above-identified patent and that said Letters Patent is hereby corrected as shown below:

In the Claims

In Claim 22, Column 69, Line 56, delete "(CIVIL)" and replace with --(CML)-- therefor.

In Claim 25, Column 69, Line 63, delete "(CIVIL)" and replace with --(CML)-- therefor.

In Claim 26, Column 69, Line 65, delete "(CIVIL)" and replace with --(CML)-- therefor.

In Claim 52, Column 71, Line 2, delete "(CIVIL)" and replace with --(CML)-- therefor.

In Claim 55, Column 71, Line 9, delete "(CIVIL)" and replace with --(CML)-- therefor.

In Claim 56, Column 71, Line 11, delete "(CIVIL)" and replace with --(CML)-- therefor.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*